United States Patent
Okuda et al.

(10) Patent No.: US 8,778,510 B2
(45) Date of Patent: Jul. 15, 2014

(54) PYRROMETHENE-BORON COMPLEX COMPOUNDS AND ORGANIC ELECTROLUMINESCENT ELEMENTS USING SAME

(75) Inventors: Fumio Okuda, Sodegaura (JP); Kiyoshi Ikeda, Sodegaura (JP); Takayasu Sado, Sodegaura (JP); Takahiko Ochi, Sodegaura (JP); Yoshimitsu Tanabe, Sodegaura (JP); Bunji Sawano, Yao (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 302 days.

(21) Appl. No.: 13/138,501

(22) PCT Filed: Feb. 25, 2010

(86) PCT No.: PCT/JP2010/001266
§ 371 (c)(1),
(2), (4) Date: Oct. 31, 2011

(87) PCT Pub. No.: WO2010/098098
PCT Pub. Date: Sep. 2, 2010

(65) Prior Publication Data
US 2012/0037890 A1    Feb. 16, 2012

(30) Foreign Application Priority Data
Feb. 27, 2009 (JP) .................. 2009-046466

(51) Int. Cl.
*H01L 51/54* (2006.01)
*C07F 5/04* (2006.01)

(52) U.S. Cl.
USPC .......... 428/690; 428/917; 313/504; 313/506; 548/405; 257/40

(58) Field of Classification Search
None
See application file for complete search history.

(56) References Cited

FOREIGN PATENT DOCUMENTS

| | | | |
|---|---|---|---|
| JP | 3129200 | | 5/1997 |
| JP | 2005-053900 | | 3/2005 |
| JP | 3853038 | | 12/2006 |
| JP | 2007-039588 | * | 2/2007 |
| JP | 4000893 | | 10/2007 |
| JP | 2007-039588 | | 9/2008 |
| WO | WO-2006/087459 A2 | | 8/2006 |
| WO | WO-2007/105529 A1 | | 9/2007 |
| WO | WO-2008/047744 A1 | | 4/2008 |
| WO | WO-2009/084548 A1 | | 7/2009 |

OTHER PUBLICATIONS

Translation for JP 2007-039588 (publication date Feb. 2007).*
Journal of the American Chemical Society, (2007), 129(15), pp. 4747-4761.*
Angew. Chem. Int. Ed. (2006), vol. 45, pp. 961-964.*
Z. Anorg. Allg. Chem. (2000), vol. 626, pp. 588-596.*
International Search Report in PCT/JP2010/001266 dated Apr. 20, 2010.

* cited by examiner

*Primary Examiner* — Dawn Garrett
(74) *Attorney, Agent, or Firm* — Foley & Lardner LLP

(57) ABSTRACT

A pyrromethene-boron complex compound represented by the following formula (1);

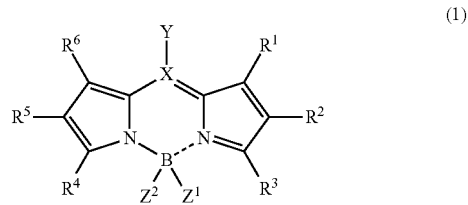

wherein $Z^1$ and $Z^2$ are independently a hydrogen atom, a substituted or unsubstituted aryl group, a substituted or unsubstituted alkoxy group or a substituted or unsubstituted aryloxy group, at least one of $Z^1$ and $Z^2$ is an alkoxy group substituted with a fluorine atom or an aryloxy group substituted with a fluorine atom or a fluoroalkyl group, and $Z^1$ and $Z^2$ may form a ring.

15 Claims, 18 Drawing Sheets

PYRROMETHENE-BORON COMPLEX COMPOUNDS AND ORGANIC ELECTROLUMINESCENT ELEMENTS USING SAME

CROSS-REFERENCE TO RELATED APPLICATIONS

This application is a National Stage application of PCT/JP2010/001266, filed Feb. 25, 2010, which claims priority from Japanese application JP 2009-046466, filed Feb. 27, 2009.

TECHNICAL FIELD

The invention relates to a pyrromethene-boron complex compound and an organic electroluminescence device using the same.

BACKGROUND ART

An organic electroluminescence device (hereinafter referred to as an "organic EL device") utilizing an organic substance has a promising feature as an inexpensive, large-area full-color solid light-emitting display element, and many developments have been made on this type of organic EL device. Normally, an organic EL device is formed of an emitting layer and a pair of opposing electrodes holding the emitting layer therebetween.

When an electric field is applied between the both electrodes, electrons are injected from the cathode and holes are injected from the anode, these electrons are then recombined with the holes in the emitting layer, thereby to cause an excited state, and energy is discharged as light when the excited state is returned to the ground state.

Conventional organic EL devices have a higher driving voltage than an inorganic light-emitting diode. The luminance and luminous efficiency thereof are also low, and their properties tend to lower significantly. For these reasons, conventional organic EL devices have not been put in a practical use. However, as a result of studies made on organic materials constituting an organic EL device, the above-mentioned problems have been gradually improved in recently-developed organic EL devices.

As an organic material constituting an organic EL device, a compound having a pyrromethene skeleton has been studied, for example (Patent Documents 1 to 5, for example). However, further improvement in luminous efficiency or the like has been demanded.

RELATED ART DOCUMENTS

Patent Documents

[Patent Document 1] WO2008/047744
[Patent Document 2] JP-A-2005-53900
[Patent Document 3] Japanese Patent No. 4000893
[Patent Document 4] Japanese Patent No. 3853038
[Patent Document 5] Japanese Patent No. 3129200

DISCLOSURE OF THE INVENTION

The invention is aimed at providing a pyrromethene-boron complex compound which enables an organic EL device having a high luminous efficiency, improved color purity and a prolonged luminous life.

The invention is aimed at providing a pyrromethene-boron complex compound which hardly causes concentration quenching even if the doping concentration is increased when used as a dopant.

The invention is also aimed at providing a pyrromethene-boron complex compound which has a high volatility, can be deposited at a lower temperature, and is hardly thermally-decomposed even if heated for a long period of time.

According to the invention, the following pyrromethene-boron complex compound or the like can be provided.

1. A pyrromethene-boron complex compound represented by the following formula (1):

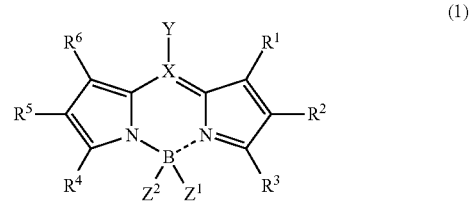

(1)

wherein $R^1$ to $R^6$ and Y are independently a hydrogen atom, a substituted or unsubstituted alkyl group, a substituted or unsubstituted cycloalkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, a substituted or unsubstituted heterocyclic group, a halogen atom, a haloalkyl group, a carboxyl group, an ester group, a carbamoyl group, an amino group, a nitro group, a cyano group, a silyl group or a siloxanyl group, adjacent substituents of $R^1$ to $R^6$ may form a substituted or unsubstituted fused aromatic ring or a substituted or unsubstituted aliphatic ring, X is a carbon atom or a nitrogen atom, and when X is a nitrogen atom, Y is not present, $Z^1$ and $Z^2$ are independently a hydrogen atom, a substituted or unsubstituted aryl group, a substituted or unsubstituted alkoxy group or a substituted or unsubstituted aryloxy group, at least one of $Z^1$ and $Z^2$ is an alkoxy group substituted with a fluorine atom or an aryloxy group substituted with a fluorine atom or a fluoroalkyl group, and $Z^1$ and $Z^2$ may form a ring.

2. The pyrromethene-boron complex compound according to 1, which is represented by the following formula (2):

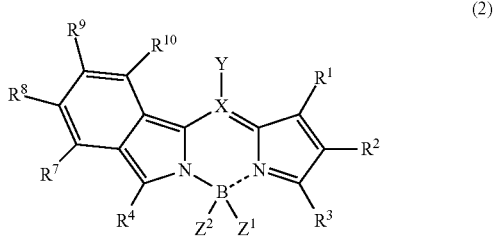

(2)

wherein $R^1$ to $R^4$, X, Y and $Z^1$ and $Z^2$ are the same as those in the formula (1), $R^7$ to $R^{10}$ are independently a hydrogen atom, a substituted or unsubstituted alkyl group, a substituted or unsubstituted cycloalkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, a substituted or unsubstituted heterocyclic group, a halogen atom, a haloalkyl group, a carboxyl group, an ester group, a carbamoyl group, an amino group, a nitro group, a cyano group, a silyl group or a siloxanyl group, and adjacent substituents of $R^1$ to $R^4$ and $R^7$ to $R^{10}$ may form a substituted or unsubstituted fused aromatic ring or a substituted or unsubstituted aliphatic ring.

3. The pyrromethene-boron complex compound according to 1 or 2, wherein in the formula (1) or (2), X is a carbon atom, and Y is a hydrogen atom.

4. The pyrromethene-boron complex compound according to 3, wherein $R^1$, $R^3$, $R^4$ and $R^8$ in the formula (1), or $R^1$, $R^3$ and $R^4$ in the formula (2) are independently a substituted or unsubstituted aryl group.

5. The pyrromethene-boron complex compound according to any of 1 to 4, wherein in the formula (1) or (2), at least one of $Z^1$ and $Z^2$ is an alkoxy group substituted with a fluorine atom.

6. The pyrromethene-boron complex compound according to any of 1 to 5, which is a dopant for an organic electroluminescence device.

7. An organic electroluminescence device comprising:
an anode, a cathode, and
one or a plurality of organic thin film layers between the anode and the cathode, the organic thin film layers comprising at least an emitting layer,
wherein at least one of the organic thin film layers comprises the pyrromethene-boron complex compound according to any of 1 to 6.

8. The organic electroluminescence device according to 7, wherein the emitting layer comprises the pyrromethene-boron complex compound.

9. The organic electroluminescence device according to 8, wherein the emitting layer further comprises a naphthacene derivative represented by the following formula (3):

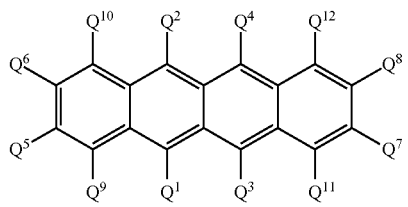

(3)

wherein $Q^1$ to $Q^{12}$ are independently a hydrogen atom, a substituted or unsubstituted alkyl group having 1 to 20 carbon atoms, a substituted or unsubstituted aryl group having 6 to 20 carbon atoms that form a ring (hereinafter referred to as "ring carbon atoms"), an amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 atoms that form a ring (hereinafter referred to as "ring atoms").

10. The organic electroluminescence device according to 9, wherein at least one of $Q^1$, $Q^2$, $Q^3$ and $Q^4$ of the naphthacene derivative represented by the formula (3) is an aryl group.

11. The organic electroluminescence device according to 9 or 10, wherein the naphthacene derivative represented by the formula (3) is a naphthacene derivative represented by the following formula (4):

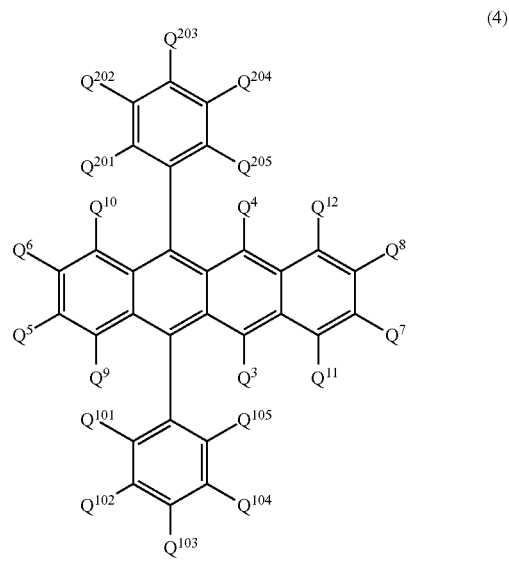

(4)

wherein $Q^3$ to $Q^{12}$ are the same as those in the formula (3), $Q^{101}$ to $Q^{105}$ and $Q^{201}$ to $Q^{205}$ are independently a hydrogen atom, a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms, and adjacent substituents of $Q^{101}$ to $Q^{105}$ and $Q^{201}$ to $Q^{205}$ may form a ring.

12. The organic electroluminescence device according to 11, wherein at least one of $Q^{101}$, $Q^{105}$, $Q^{201}$ and $Q^{205}$ of the naphthacene derivative represented by the formula (4) is a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms.

According to the invention, a pyrromethene-boron complex compound which enables an organic EL device having a high luminous efficiency, improved color purity and a prolonged luminous life can be provided.

According to the invention, a pyrromethene-boron complex compound which hardly suffers concentration quenching even if the doping concentration is increased when used as a dopant can be provided.

According to the invention, a pyrromethene-boron complex compound which has a high volatility, can be deposited at a lower temperature, and is hardly thermally-decomposed even if heated for a long period of time can be provided.

MODE FOR CARRYING OUT THE INVENTION

Figure 1:
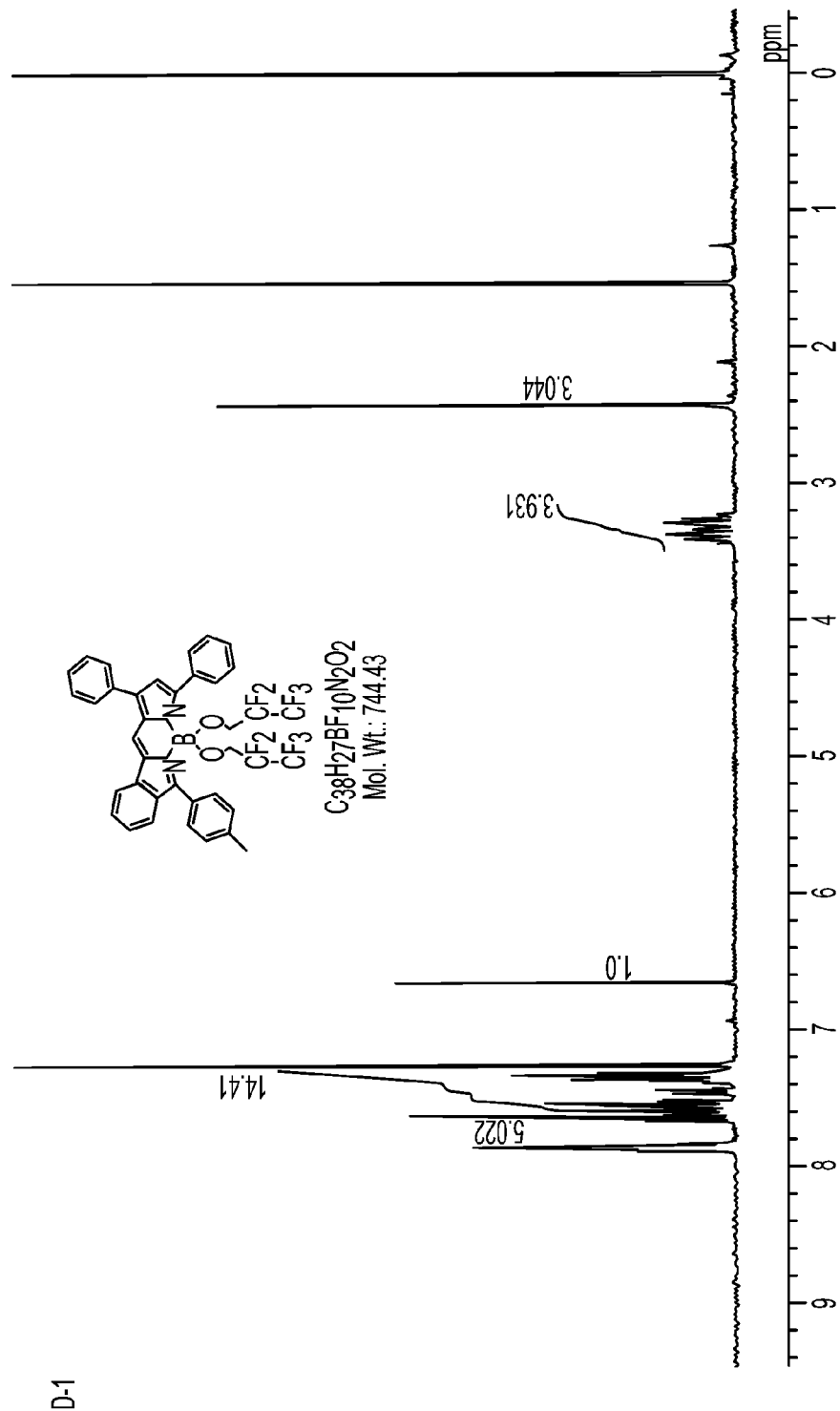
FIG. 1 is an H-NMR spectrum of the compound D-1 synthesized in Synthesis Example 1.

The pyrromethene-boron complex compound of the invention is a compound represented by the following formula (1):

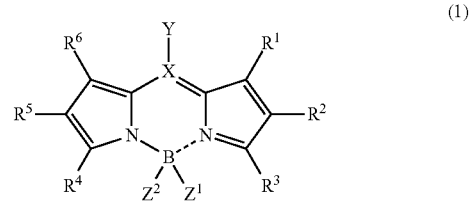

(1)

wherein $R^1$ to $R^6$ and Y are independently a hydrogen atom, a substituted or unsubstituted alkyl group, a substituted or unsubstituted cycloalkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, a substituted or unsubstituted heterocyclic group, a halogen atom, a haloalkyl group, a carboxyl group, an ester group, a carbamoyl group, an amino group, a nitro group, a cyano group, a silyl group or a siloxanyl group, adjacent substituents of $R^1$ to $R^6$ may form a substituted or unsubstituted fused aromatic ring or a substituted or unsubstituted aliphatic ring, X is a carbon atom or a nitrogen atom, and when X is a nitrogen atom, Y is not present, $Z^1$ and $Z^2$ are independently a hydrogen atom, a substituted or unsubstituted aryl group, a substituted or unsubstituted alkoxy group or a substituted or unsubstituted aryloxy group, at least one of $Z^1$ and $Z^2$ is an alkoxy group substituted with a fluorine atom or an aryloxy group substituted with a fluorine atom or a fluoroalkyl group, and $Z^1$ and $Z^2$ may form a ring.

The pyrromethene-boron complex compound represented by the formula (1) is preferably a pyrromethene-boron complex compound represented by the following formula (2).

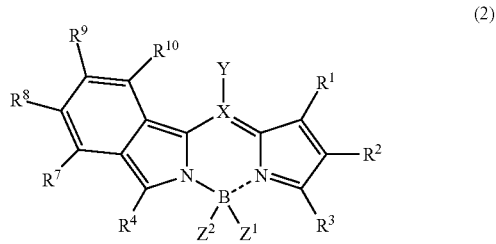

(2)

wherein $R^1$ to $R^4$, X, Y and $Z^1$ and $Z^2$ are the same as those in the formula (1), $R^1$ to $R^{10}$ are independently a hydrogen atom, a substituted or unsubstituted alkyl group, a substituted or unsubstituted cycloalkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, a substituted or unsubstituted heterocyclic group, a halogen atom, a haloalkyl group, a carboxyl group, an ester group, a carbamoyl group, an amino group, a nitro group, a cyano group, a silyl group or a siloxanyl group, and adjacent substituents of $R^1$ to $R^4$ and $R^1$ to $R^{10}$ may form a substituted or unsubstituted fused aromatic ring or a substituted or unsubstituted aliphatic ring.

In the formula (1) or (2), it is preferred that X be carbon and Y be hydrogen.

It is preferred that $R^1$, $R^3$, $R^4$ and $R^6$ in the formula (1) or $R^1$, $R^3$ and $R^4$ in the formula (2) be independently a substituted or unsubstituted aryl group.

It is preferred that at least one of $Z^1$ and $Z^2$ in the formula (1) or (2) be an alkoxy group substituted with fluorine.

As the substituted or unsubstituted alkyl group represented by $R^1$ to $R^{10}$ and Y, an alkyl group having 1 to 20 carbon atoms and a fluorine-substituted alkyl group having 1 to 20 carbon atoms can be given. Specific examples thereof include methyl, ethyl, t-butyl, propyl, isopropyl, n-butyl, s-butyl, isobutyl, n-pentyl, n-hexyl, n-heptyl, n-octyl, 2-cyclopentylethyl, 2-cyclohexylethyl, 4-cyclohexylbutyl, trifluoromethyl, 3,3,3-trifluoropropyl, 3,3,4,4,4-pentafluorobutyl, 2-trifluoromethyl-3,3,3-trifluoropropyl and 3,3,4,4,5,5,5-hexafluoropentyl.

As the substituted or unsubstituted cycloalkyl group represented by $R^1$ to $R^{10}$ and Y, a cycloalkyl group having 1 to 20 carbon atoms can be given. Specific examples thereof include cyclobutyl, cyclopentyl, cyclohexyl, cycloheptyl and cyclooctyl.

As the substituted or unsubstituted aryl group represented by $R^1$ to $R^{10}$, Y, $Z^1$ and $Z^2$, an aryl group having 6 to 30 carbon atoms can be given. Specific examples thereof include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 3-naphthacenyl, 1-pyrenyl, 2-pyrenyl, 4-pyrenyl, biphenyl-2-yl, biphenyl-3-yl, biphenyl-4-yl, p-terphenyl-4-yl, p-terphenyl-3-yl, p-terphenyl-2-yl group, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenyl-4-yl, 4"-t-butyl-p-terphenyl-4-yl, 9,9-dimethylfluorene-1-yl, 9,9-dimethylfluorene-2-yl, 9,9-dimethylfluorene-3-yl, 9,9-dimethylfluorene-4-yl, 2-methoxyphenyl, 2,4,6-trimethylphenyl, 4-methoxyphenyl, 4-fluorophenyl, 4-phenoxyphenyl, 2,6-dimethoxyphenyl, 2-trifluoromethylphenyl and 2,4-dimethylphenyl.

As the substituted or unsubstituted alkoxy group represented by $R^1$ to $R^{10}$, Y, $Z^1$ and $Z^2$, an alkoxy group having 1 to 20 carbon atoms in total can be given. Specific examples thereof include methoxy, ethoxy, n-propoxy, isopropoxy, n-butoxy, isobutoxy, sec-butoxy, n-pentyloxy, n-hexyloxy, n-heptyloxy and n-octyloxy.

As the substituted or unsubstituted alkylthio group represented by $R^1$ to $R^{10}$ and Y, an alkylthio group having 1 to 20 carbon atoms in total can be given. Specific examples thereof include methylthio, ethylthio, 1-propylthio, 2-propylthio, 1-butylthio, 2-butylthio, sec-butylthio, tert-butylthio, n-pentylthio, n-hexylthio, n-octylthio, n-decylthio, n-dodecylthio, 2-ethylhexylthio, 3,7-dimethyloctylthio, cyclopropylthio, cyclopentylthio, cyclohexylthio, 1-adamantylthio, 2-adamantylthio, norbornylthio and trifluoromethylthio.

As the substituted or unsubstituted aryloxy group represented by $R^1$ to $R^{10}$, Y, $Z^1$ and $Z^2$, an aryloxy group having 6 to 30 carbon atoms can be given.
Specific examples thereof include phenoxy, methylphenoxy, dimethylphenoxy, ethylphenoxy, trimethylphenoxy, propylphenoxy, tetramethylphenoxy, diethylphenoxy, butylphenoxy, 1-naphthyloxy, oxyindanyl and oxyindenyl.

As the substituted or unsubstituted arylthio group represented by $R^1$ to $R^{10}$ and Y, an arylthio group having 6 to 30 carbon atoms in total can be given. Specific examples thereof include phenylthio, benzylthio, methylphenylthio, dimethylphenylthio, ethylphenylthio, trimethylphenylthio, propylphenylthio, tetramethylphenylthio, diethylphenylthio, butylphenylthio, naphthylthio, indenylthio and indanylthio.

As the substituted or unsubstituted alkenyl group represented by $R^1$ to $R^{10}$ and Y, ethenyl, propenyl, butenyl, pentenyl, pentadienyl, hexenyl, hexadienyl, heptenyl, octenyl, octadienyl, 2-ethylhexenyl, decenyl, or the like can be given, for example.

As the substituted or unsubstituted aralkyl group represented by $R^1$ to $R^{10}$ and Y, benzyl, phenylethyl, phenylpropyl, phenylbutyl, indenylmethyl, indanylmethyl, naphthylmethyl, or the like can be given, for example.

As the substituted or unsubstituted heterocyclic group represented by $R^1$ to $R^{10}$ and Y, residues such as imidazole, benzimidazole, pyrrole, furan, thiophene, benzothiophene, oxadiazoline, indoline, carbazole, pyridine, quinoline, isoquinoline, benzoquinone, pyralozine, imidazolidine, piperidine, dibenzofuran, benzofuran and dibenzothiophene can be given, for example.

Specific examples of the halogen atom represented by $R^1$ to $R^{10}$ and Y include fluorine, chlorine, bromine and iodine. In view of stability of the compound, fluorine is preferable.

As the silyl group represented by $R^1$ to $R^{10}$ and Y, a trialkylsilyl group having 3 to 18 carbon atoms in total, a trialkoxysilyl group having 3 to 18 carbon atoms in total, and a triarylsilyl group having 18 to 30 carbon atoms in total can be given. Specific examples thereof include trimethylsilyl, trimethoxysilyl, triethylsilyl, triethoxysilyl, chlorodimethylsilyl, tri-iso-propylsilyl and tri-iso-propoxysilyl.

If the above-mentioned groups have a substituent, as the substituent, the substituted or unsubstituted alkyl group, the substituted or unsubstituted cycloalkyl group, the substituted or unsubstituted alkoxy group, the substituted or unsubstituted aralkyl group, the substituted or unsubstituted aryloxy group, the substituted or unsubstituted arylthio group, the substituted or unsubstituted silyl group, the carboxyl group, the halogen atom, the cyano group, the nitro group or the hydroxyl group as mentioned above can be given.

As the fluorine-substituted alkoxy group represented by $Z^1$ and $Z^2$, 2,2,2-trifluoroethoxy, 2,2-difluoroethoxy, 2,2,3,3,3-pentafluoro-1-propoxy, 2,2,3,3-tetrafluoro-1-propoxy, 1,1,1,3,3,3-hexafluoro-2-propoxy, 2,2,3,3,4,4,4-heptafluoro-1-butyloxy, 2,2,3,3,4,4-hexafluoro-1-butyloxy, nonafluoro-tert-butyloxy, 2,2,3,3,4,4,5,5,5-nonafluoropentanoxy, 2,2,3,3,4,4,5,5,6,6,6-undecafluorohexanoxy, 2,3-bis(trifluoromethyl)-2,3-butanedioxy, 1,1,2,2-tetra(trifluoromethyl) ethyleneglycoxy, 4,4,5,5,6,6,6-heptafluorohexane-1,2-dioxy, 4,4,5,5,6,6,7,7,8,8,9,9,9-tridecafluorononane-1,2-dioxy, or the like can be given, for example.

As the aryloxy which is substituted by a fluorine atom or a fluoroalkyl group represented by $Z^1$ and $Z^2$, pentafluorophenoxy, 3,4,5-trifluorophenoxy, 4-trifluoromethylphenoxy, 3,5-bistrifluoromethylphenoxy group, 3-fluoro-4-trifluoromethylphenoxy group, 2,3,5,6-tetrafluoro-4-trifluoromethylphenoxy, 4-fluorocatecholate, 4-(trifluoromethyl)catecholate, 3,5-(bistrifluoromethyl)catecholate, or the like can be given, for example.

Specific examples of the pyrromethene-boron complex compound of the invention are given below.

In the following specific examples, the coordinate bond of the pyrromethene-boron complex compound is not shown.

[I-1]
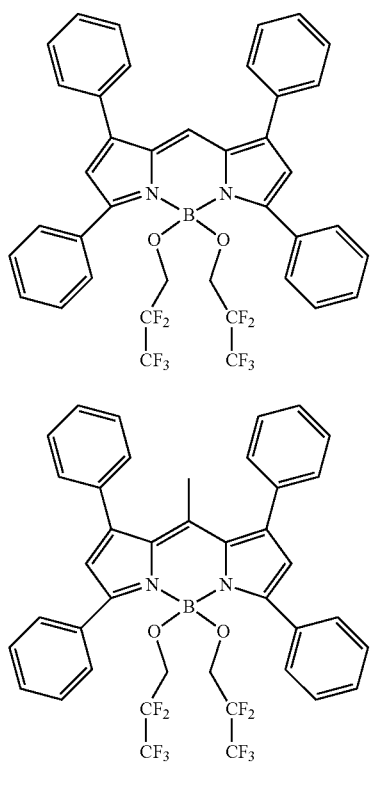
[I-2]
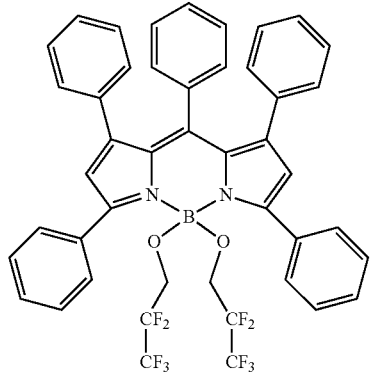
[I-3]
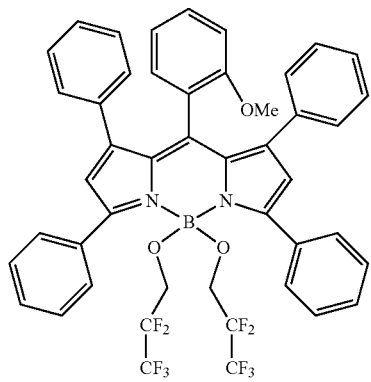
[I-4]
[I-5]
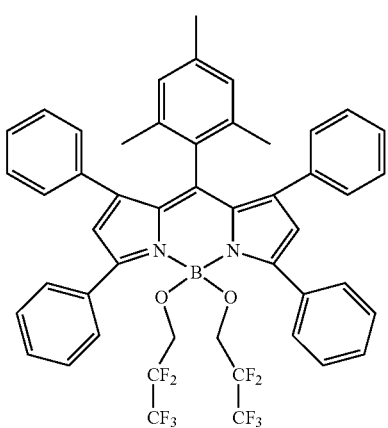
[I-6]
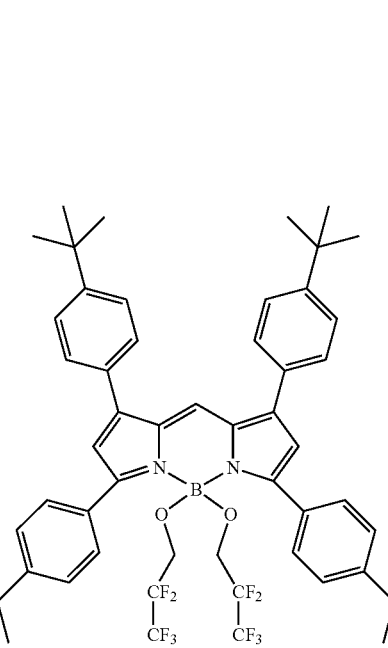
[I-7]
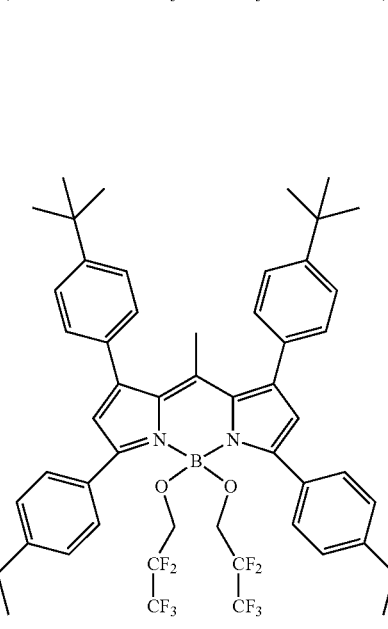

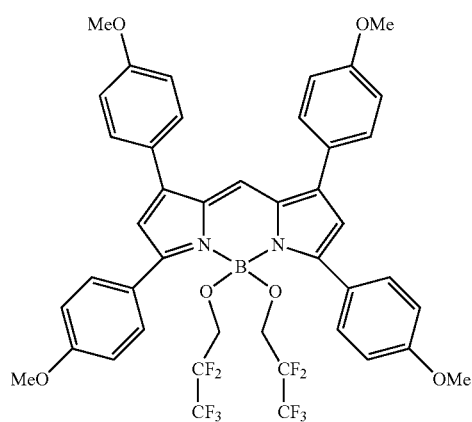
[I-8]
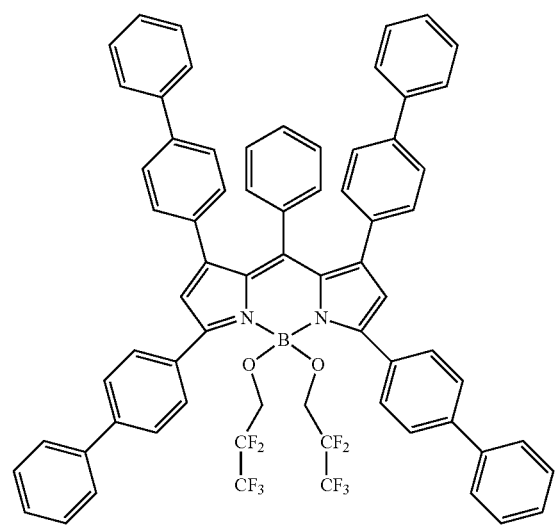
[I-11]
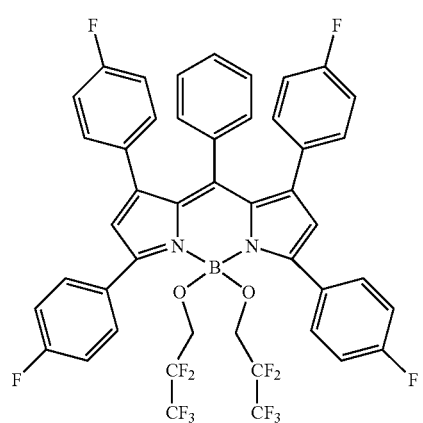
[I-9]
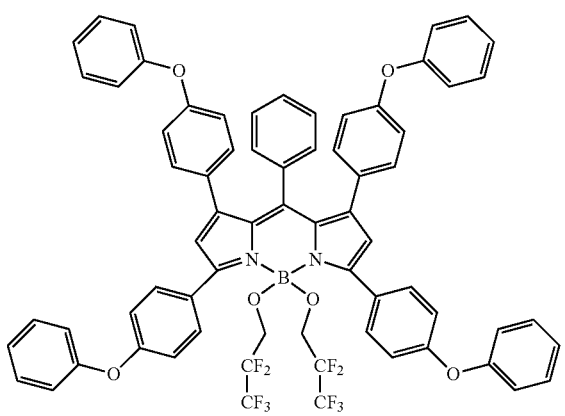
[I-12]
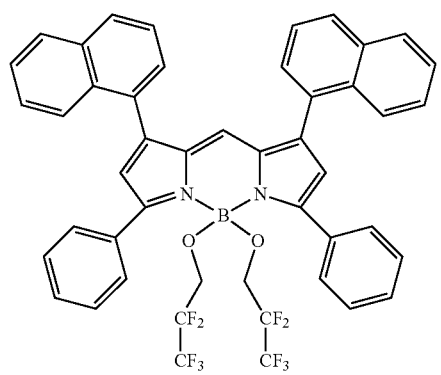
[I-10]
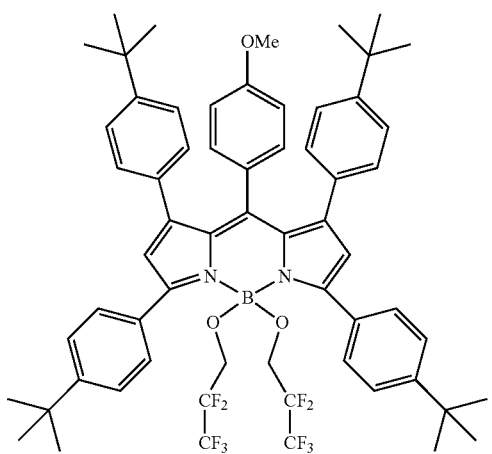
[I-13]

[I-14]
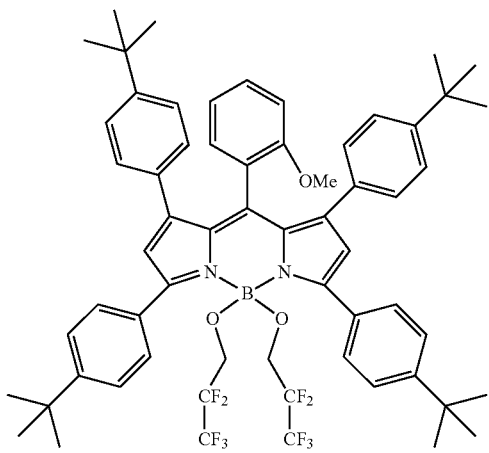
[I-15]
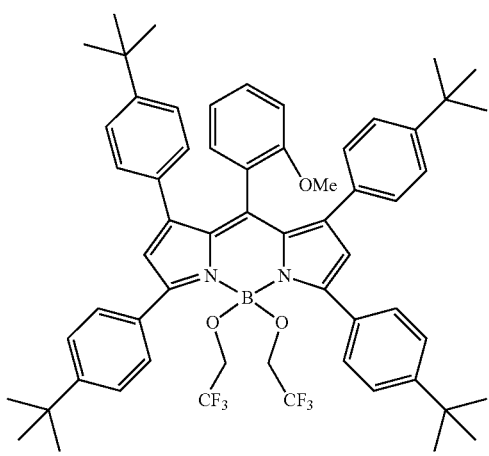
[I-16]
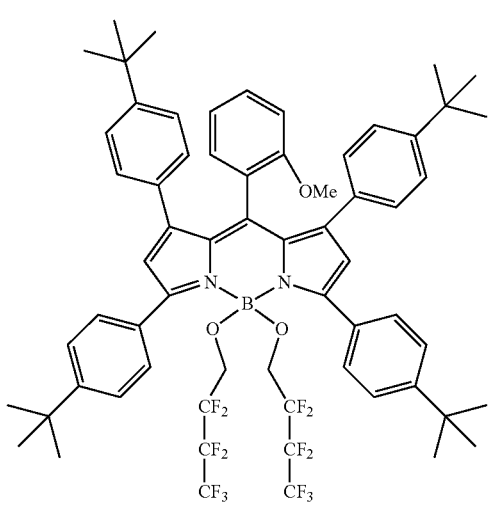
[I-17]
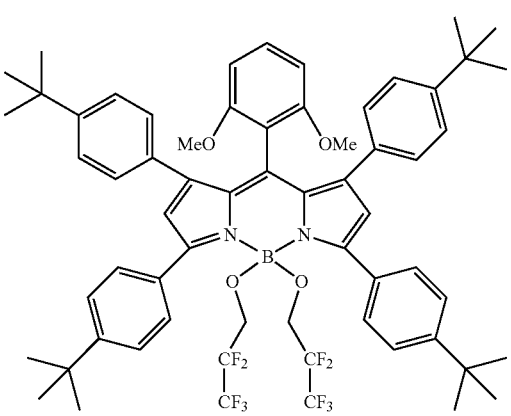
[I-18]
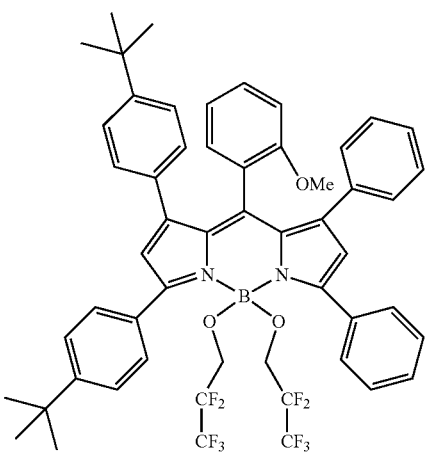
[I-19]
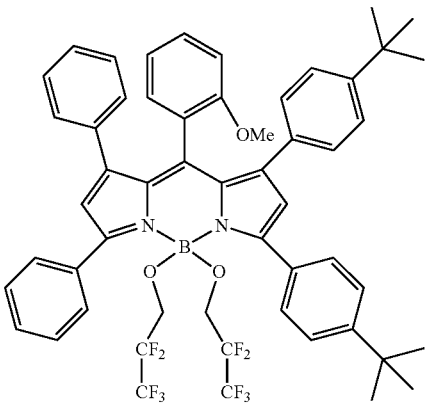

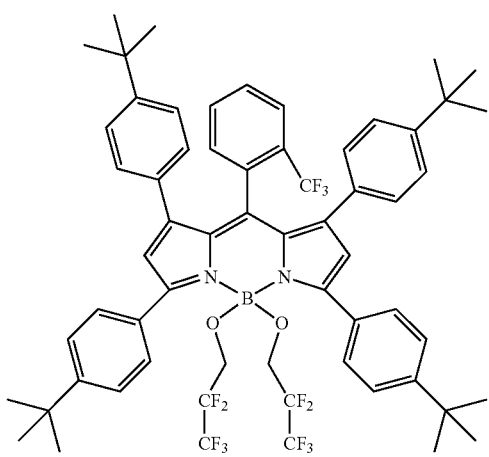
[I-20]
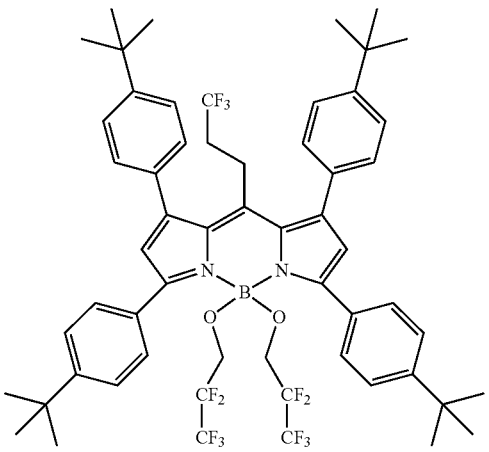
[I-23]
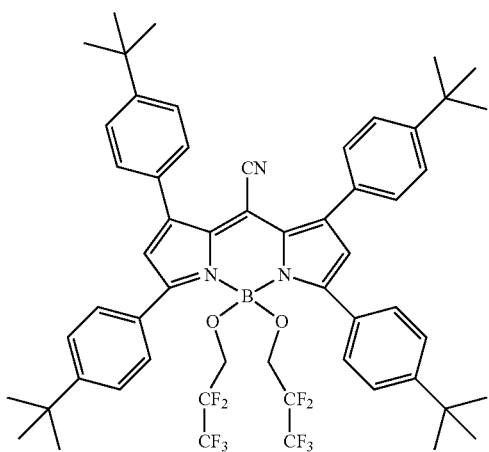
[I-21]
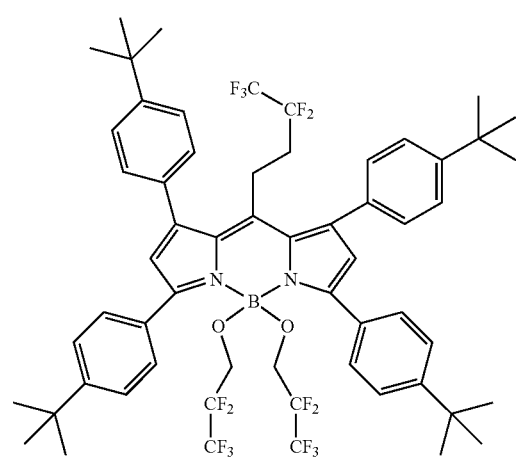
[I-24]
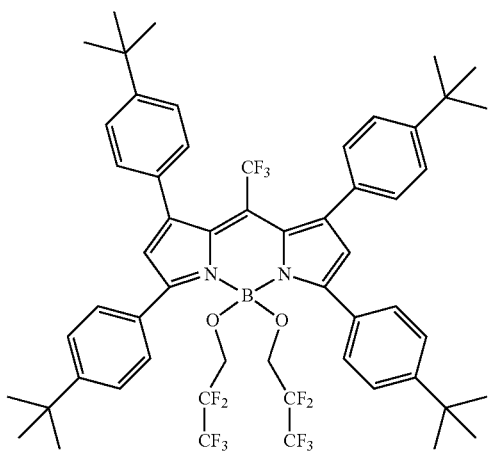
[I-22]
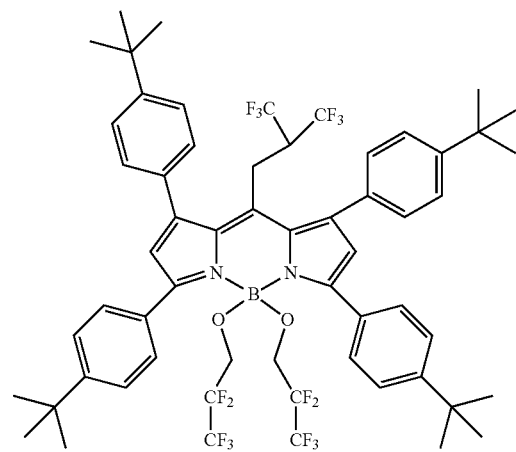
[I-25]

[I-26]
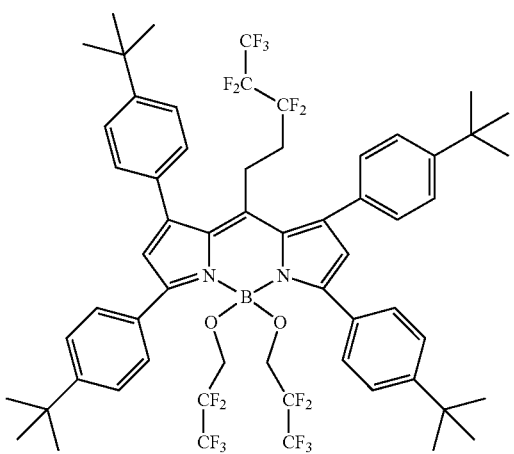
[I-29]
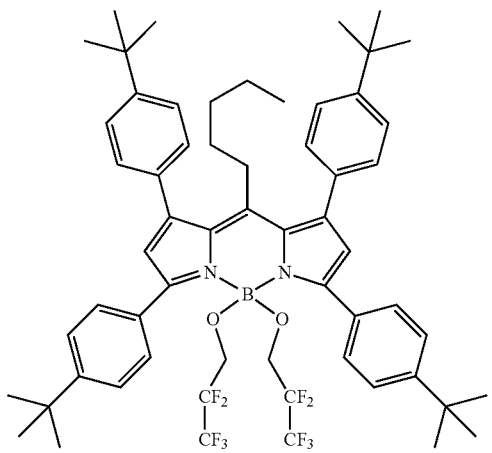
[I-27]
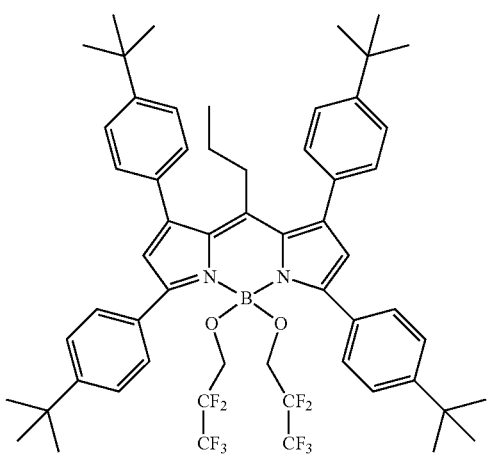
[I-30]
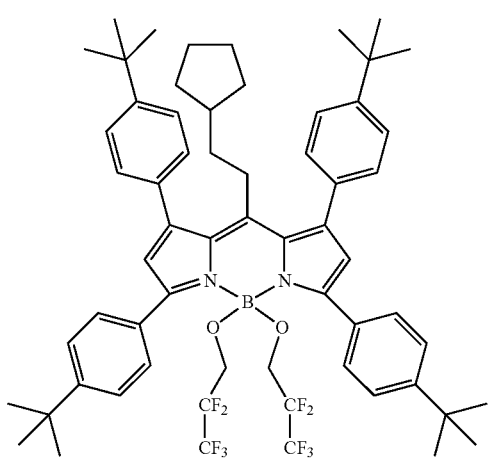
[I-28]
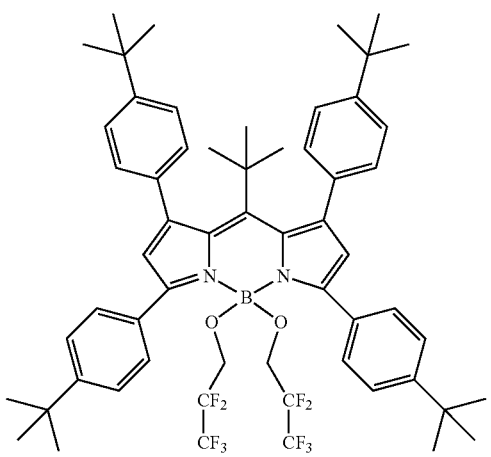
[I-31]
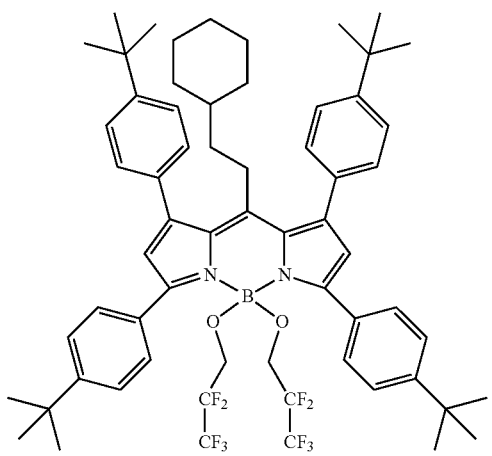

[I-32]
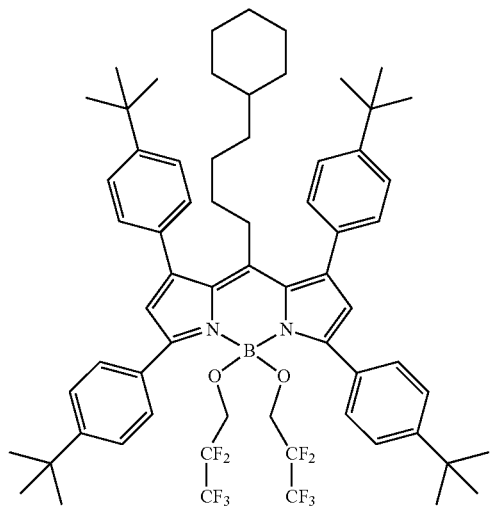
[I-33]
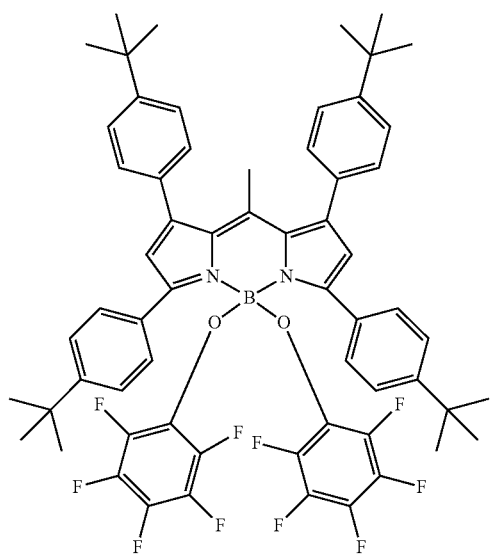
[I-34]
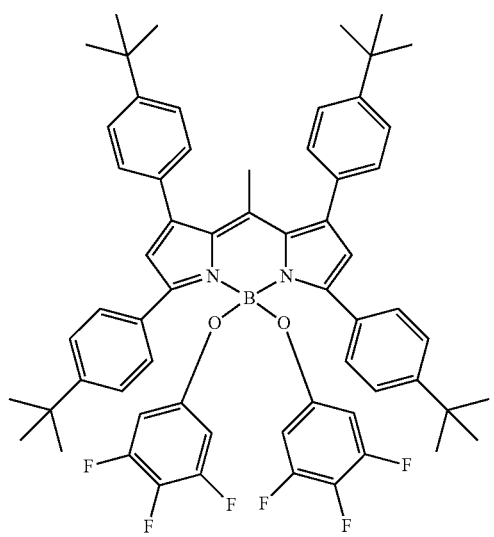
[I-35]
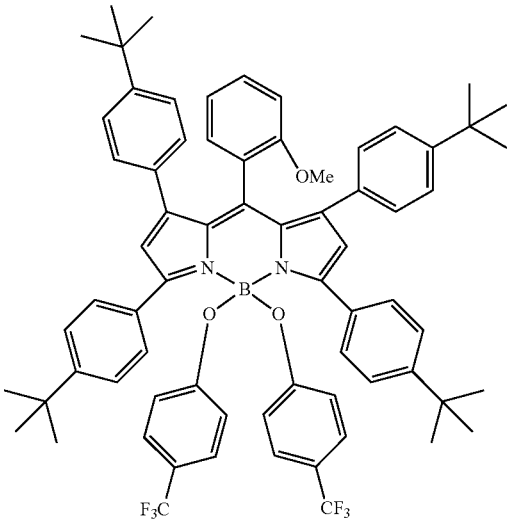
[I-36]
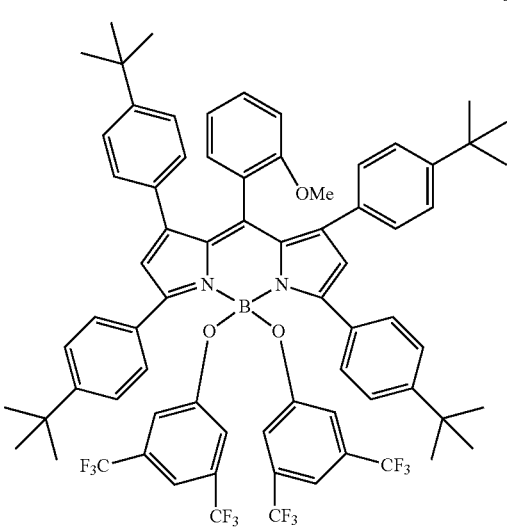
[I-37]
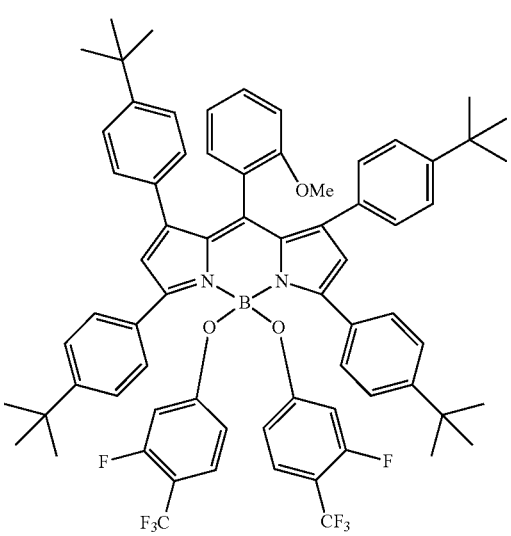

[I-38]
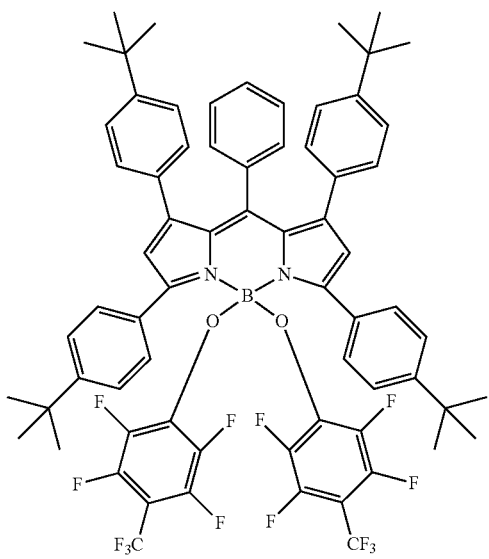
[I-40]
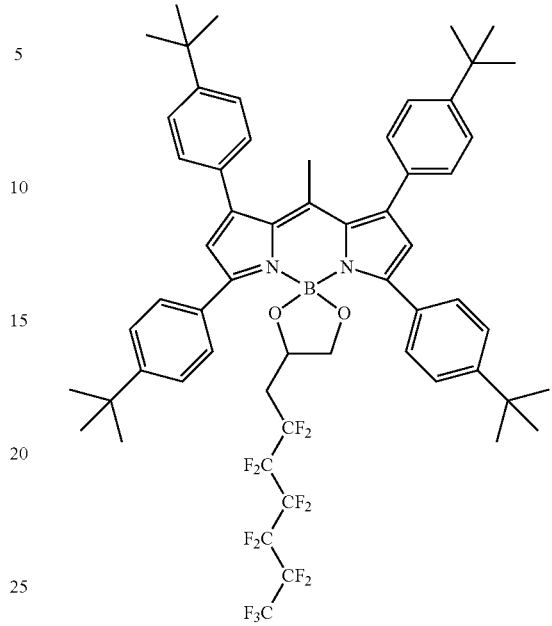
[I-39]
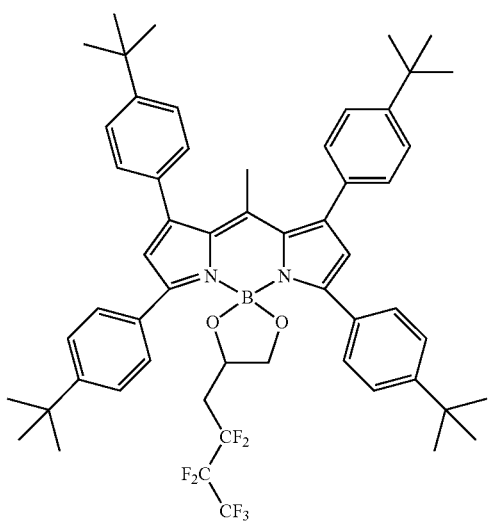
[I-41]
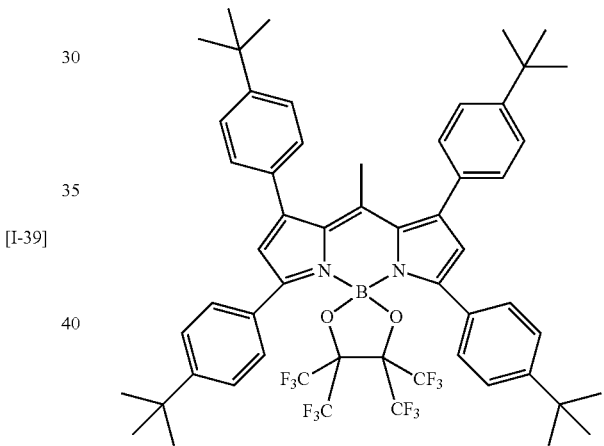
[I-42]
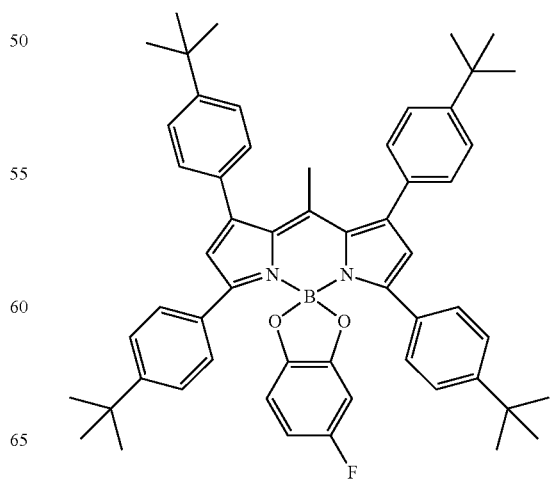

[I-43]
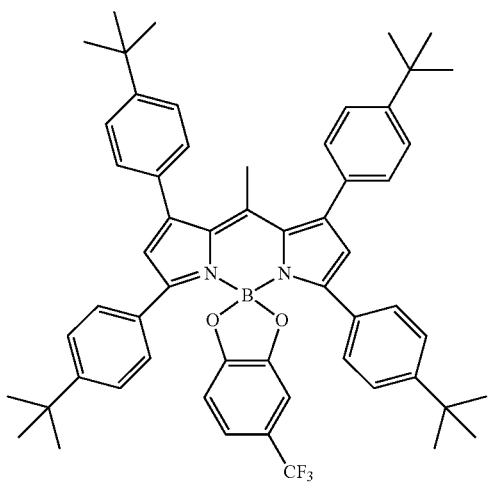
[I-44]
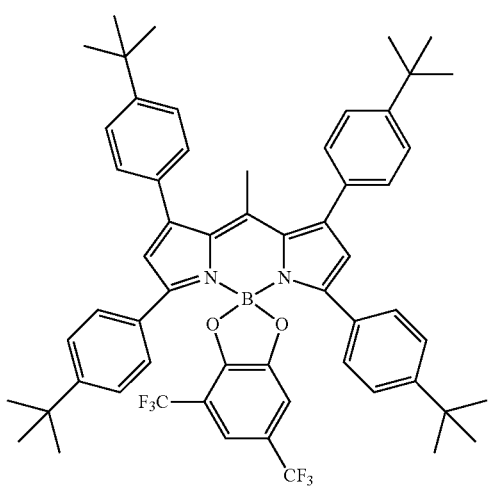
[I-45]
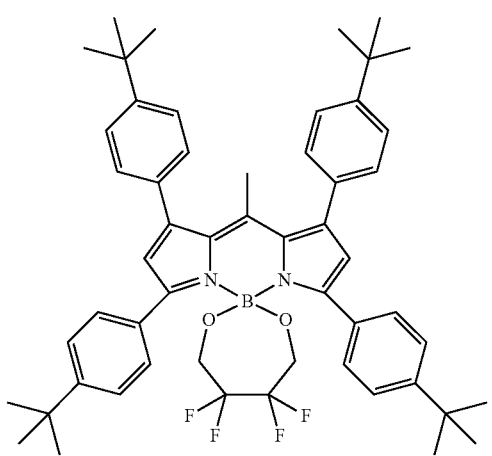
[I-46]
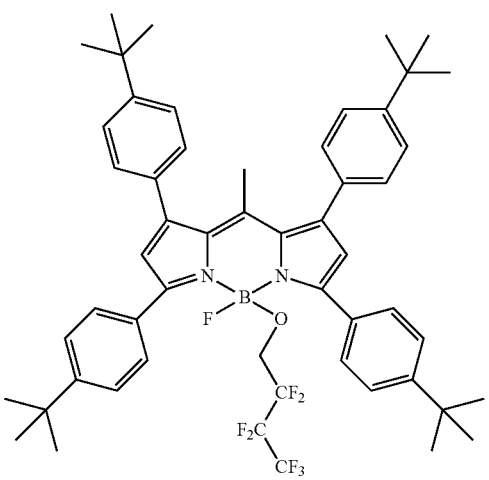
[I-47]
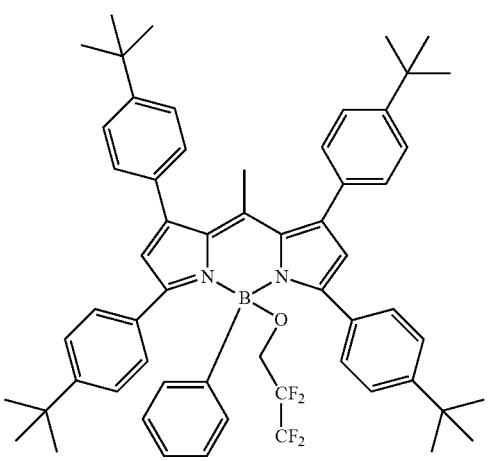
[I-48]
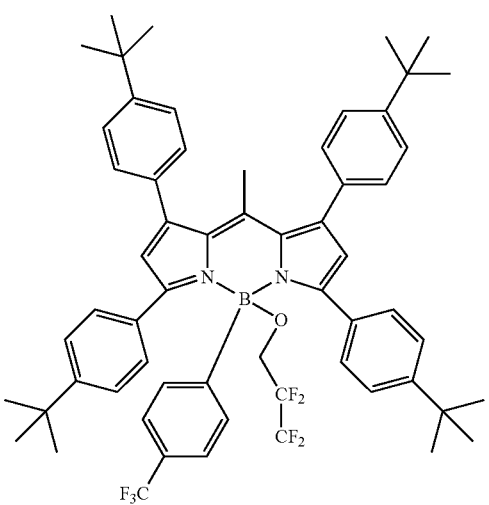

[I-49]
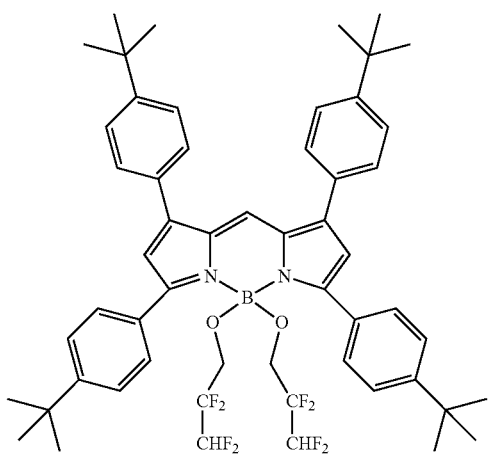
[I-52]
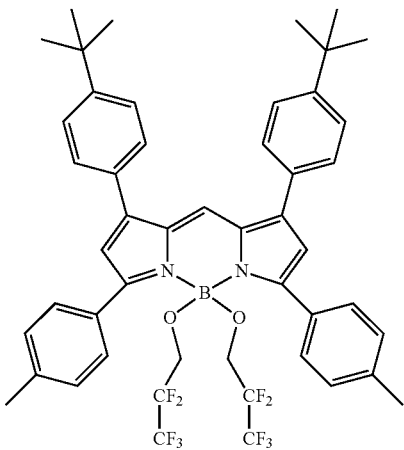
[I-50]
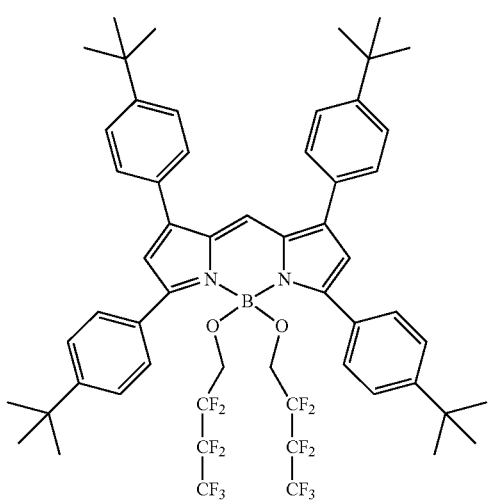
[I-53]
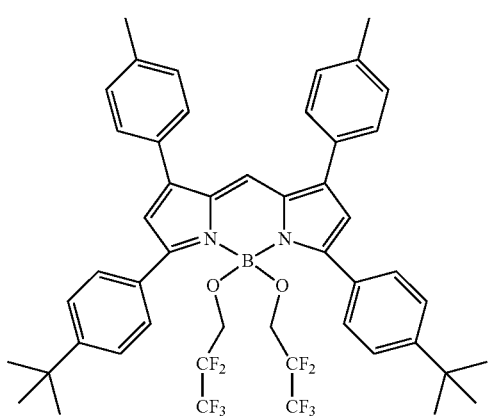
[I-51]
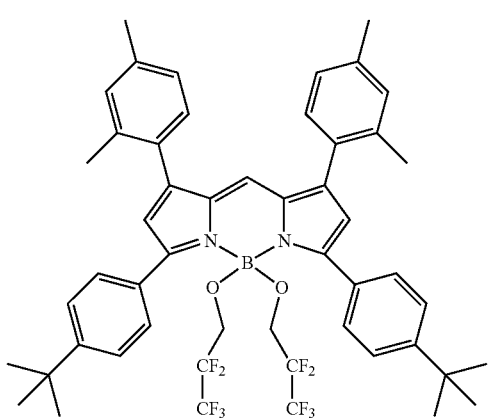
[I-54]
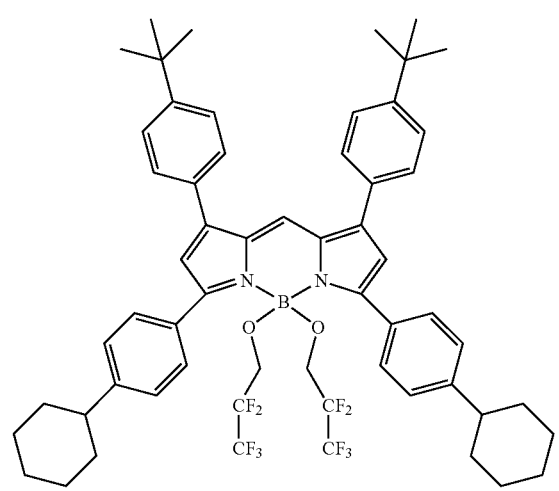

-continued
[I-55]
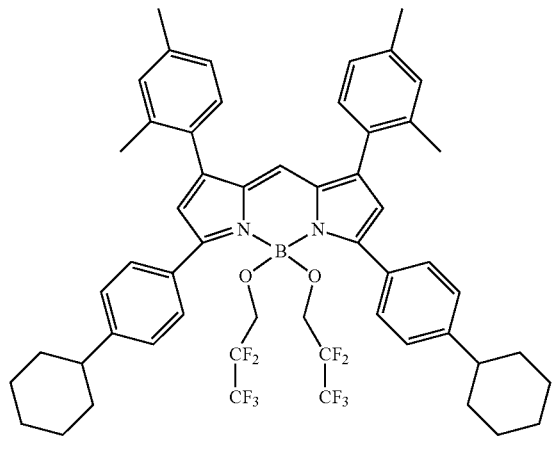
[I-56]
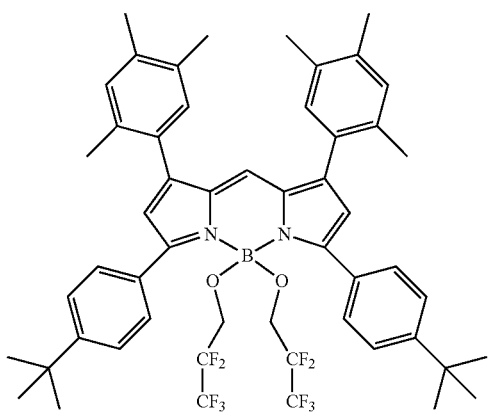
[I-57]
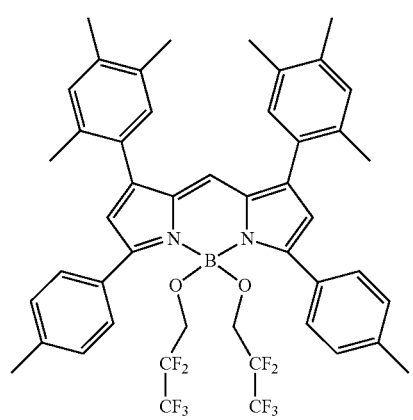
-continued
[I-58]
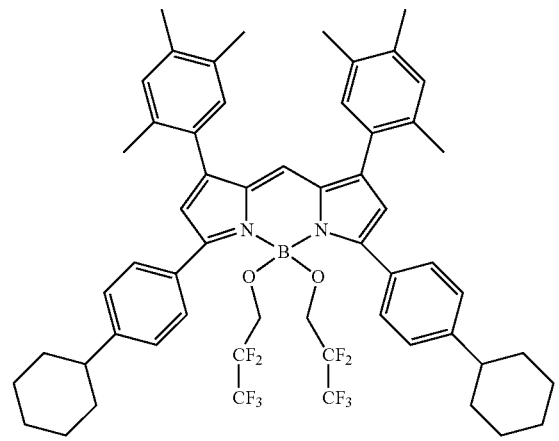
[I-59]
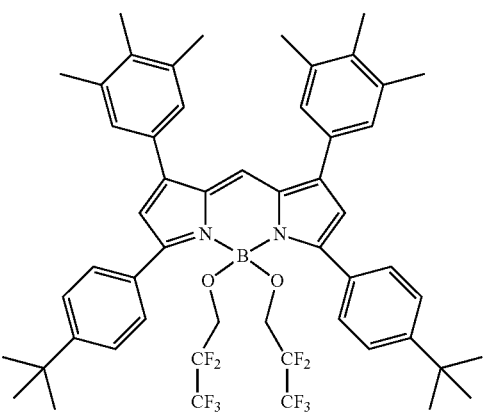
[I-60]
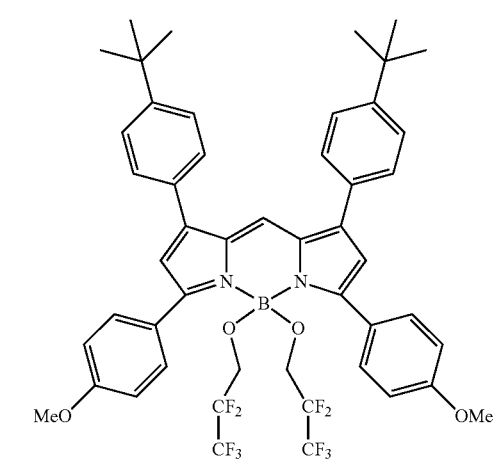

[I-61]
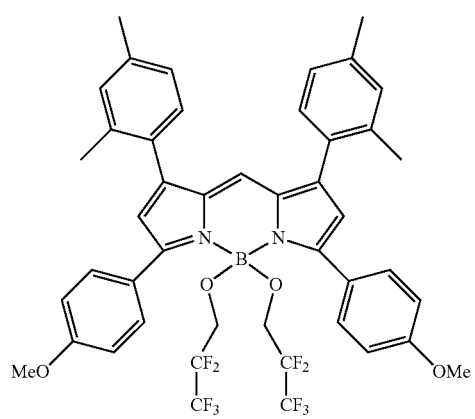
[I-62]
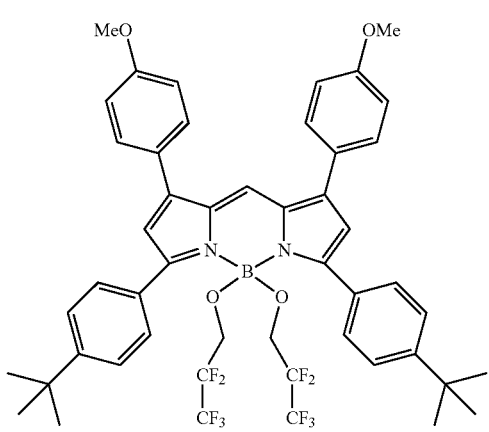
[I-63]
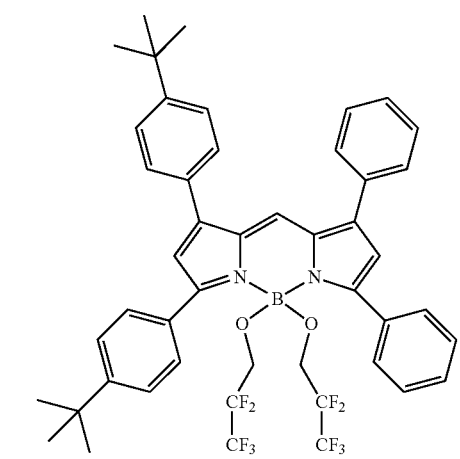
[I-64]
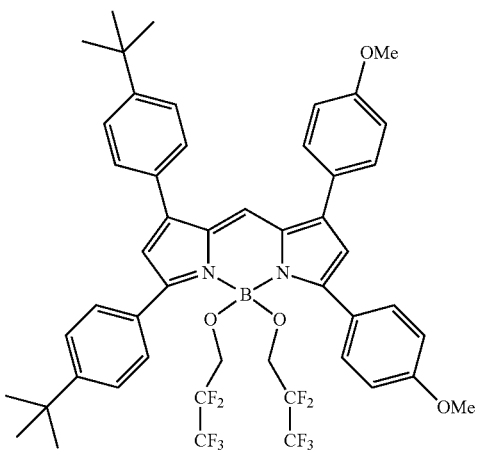
[II-1]
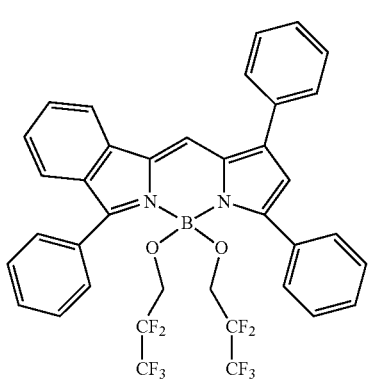
[II-2]
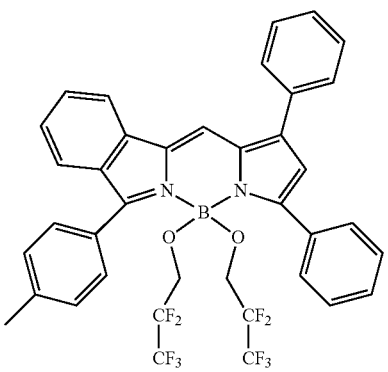
[II-3]
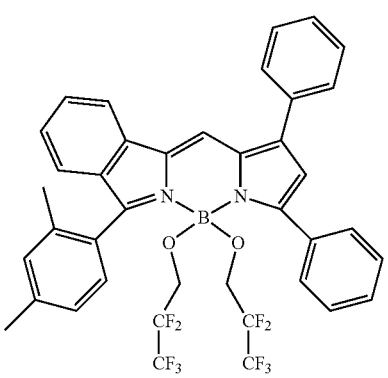

[II-4]
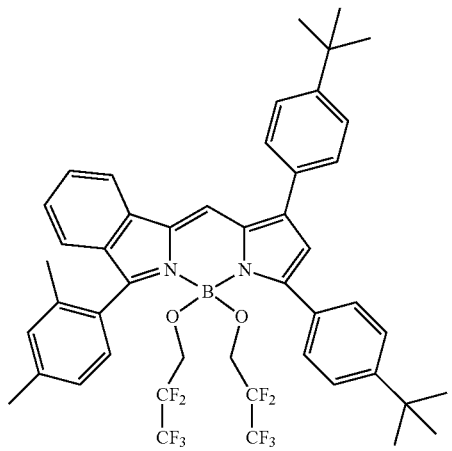
[II-5]
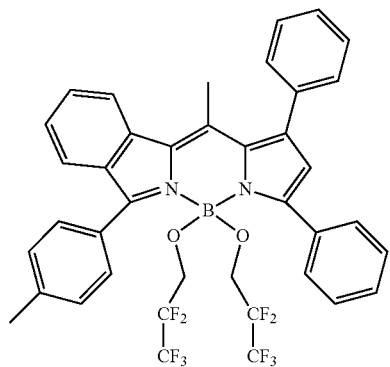
[II-6]
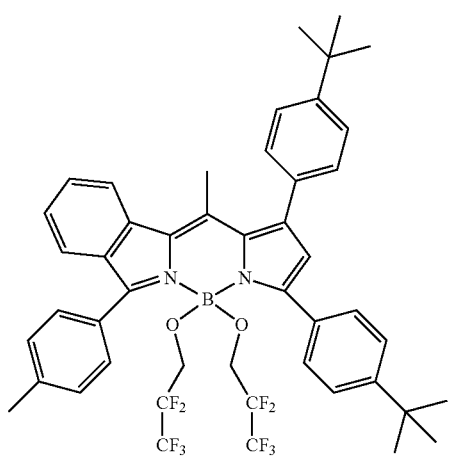
[II-7]
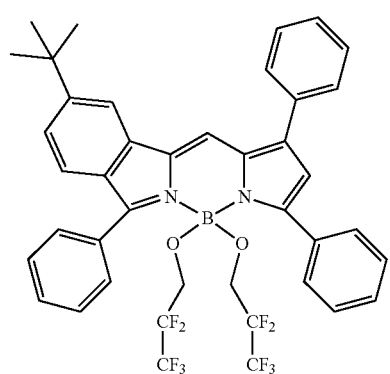
[II-8]
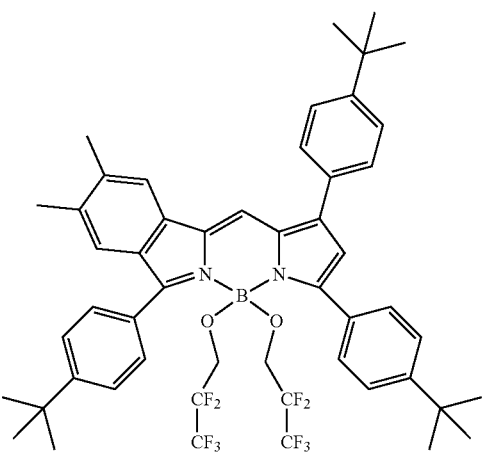
[II-9]
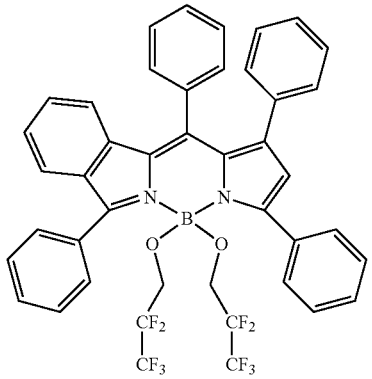
[II-10]
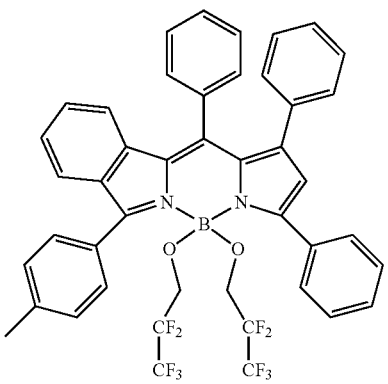

[II-11]
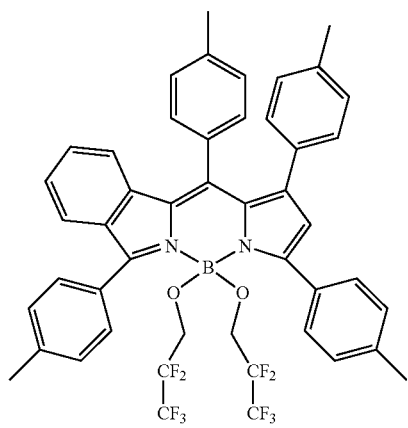
[II-14]
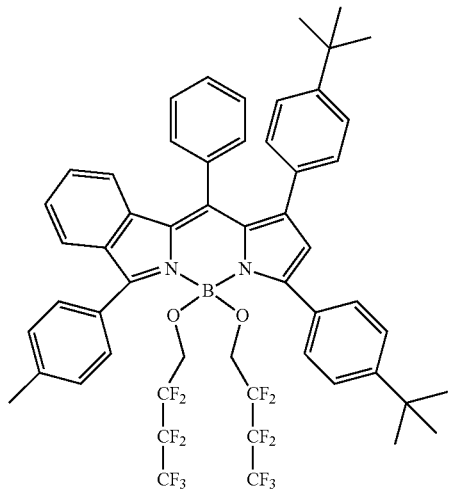
[II-12]
[II-15]
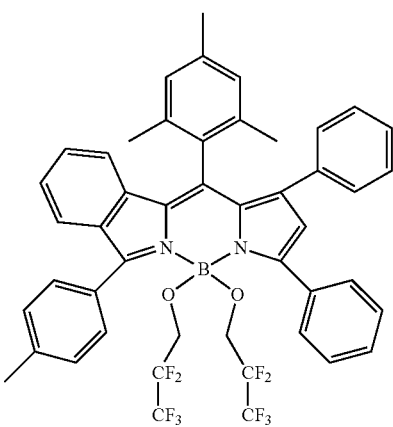
[II-13]
[II-16]
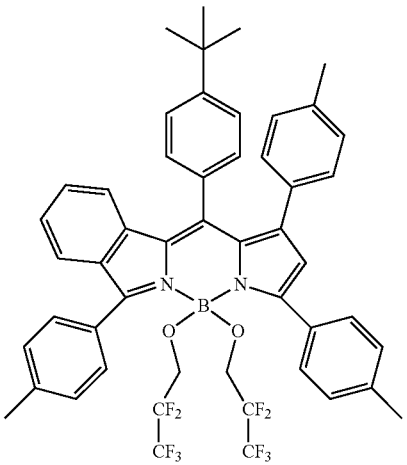

[II-17]
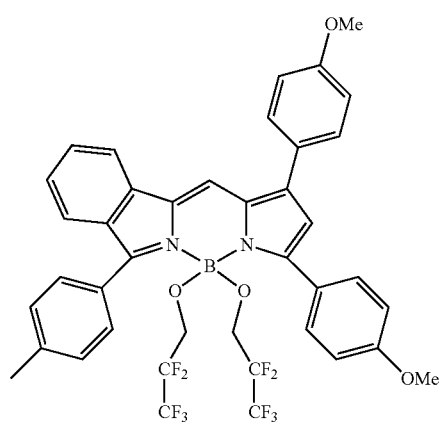
[II-18]
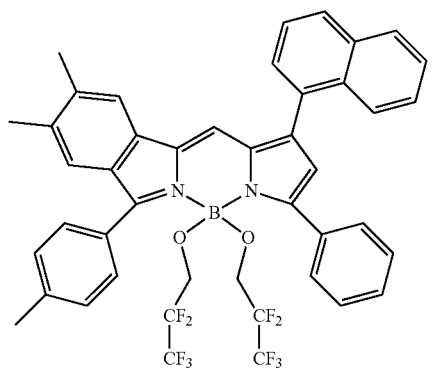
[II-19]
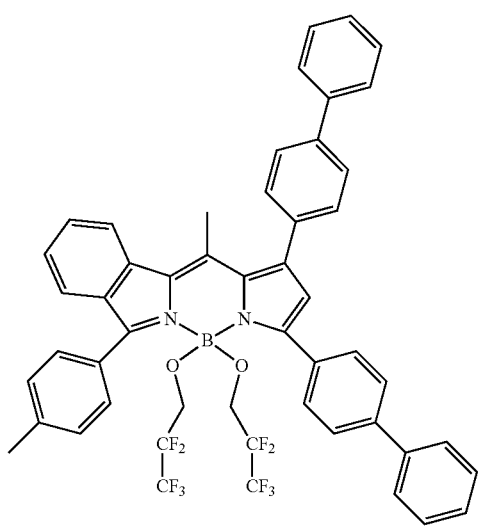
[II-20]
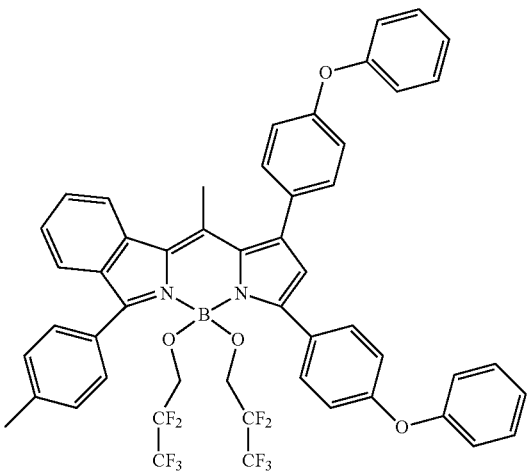
[II-21]
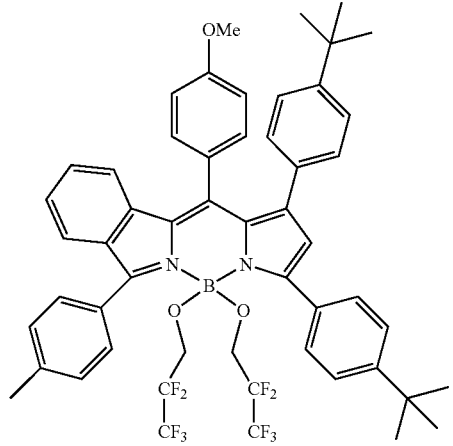
[II-22]
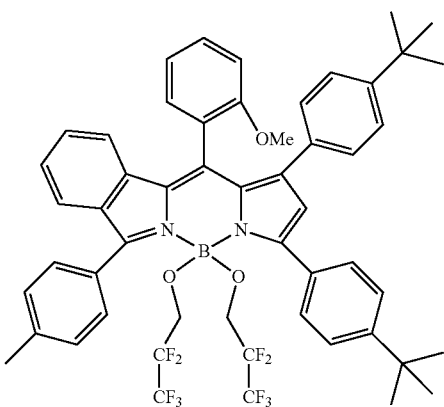

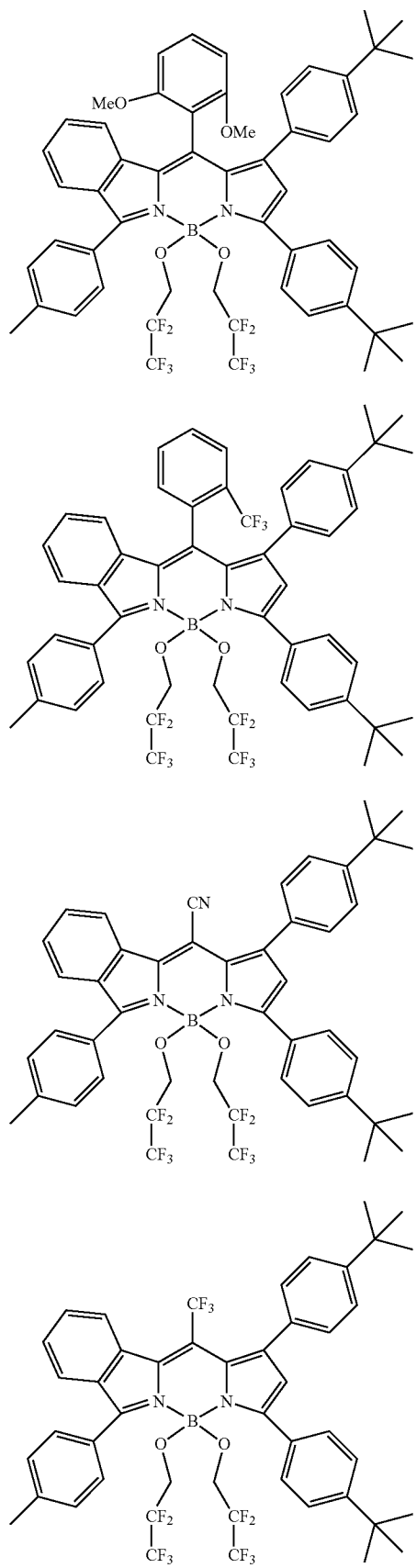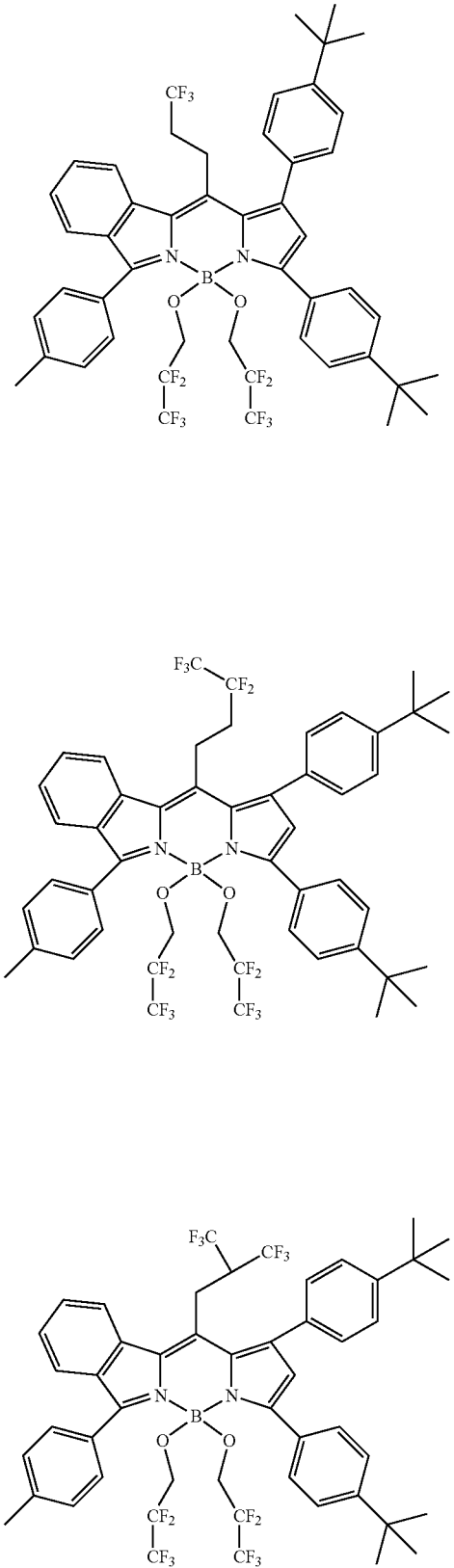

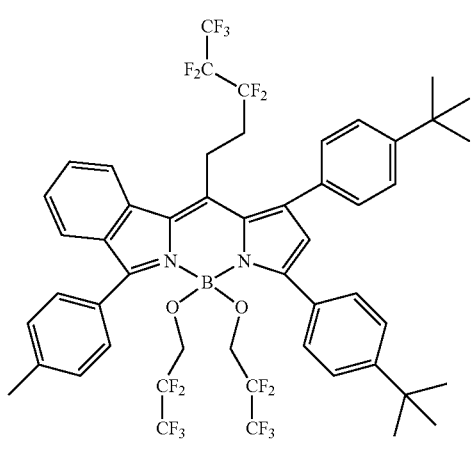
[II-30]
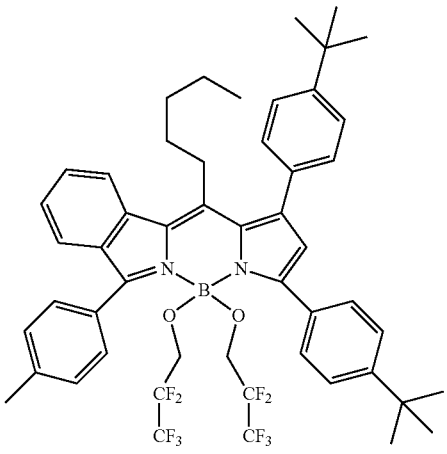
[II-33]
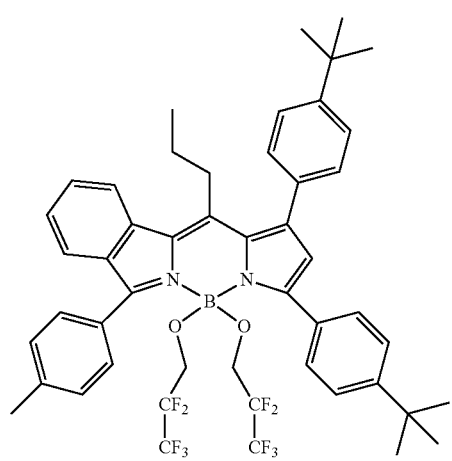
[II-31]
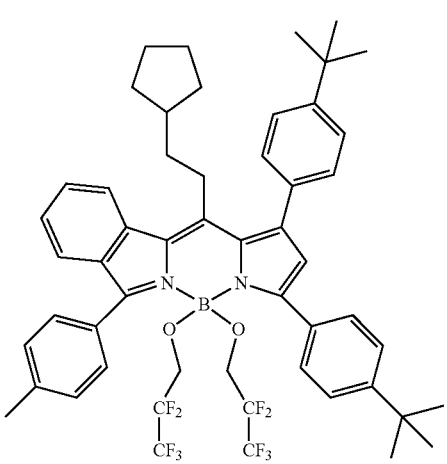
[II-34]
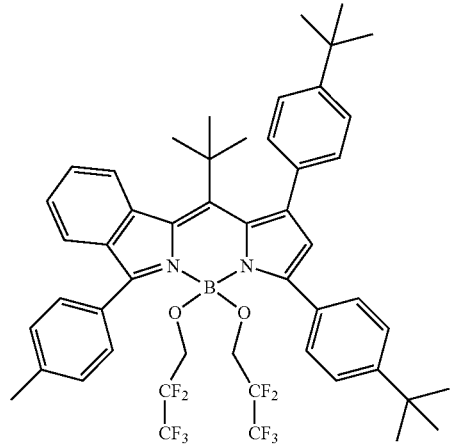
[II-32]
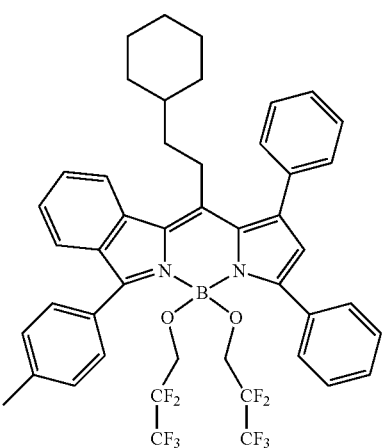
[II-35]

[II-36]
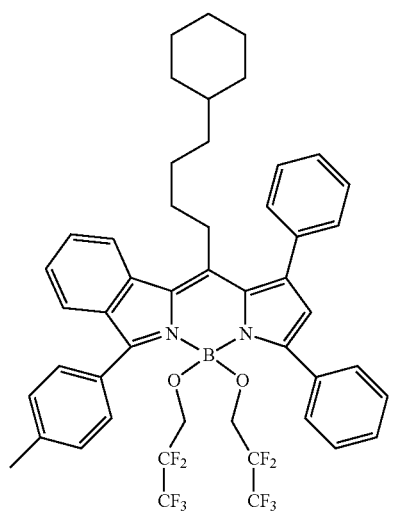
[II-37]
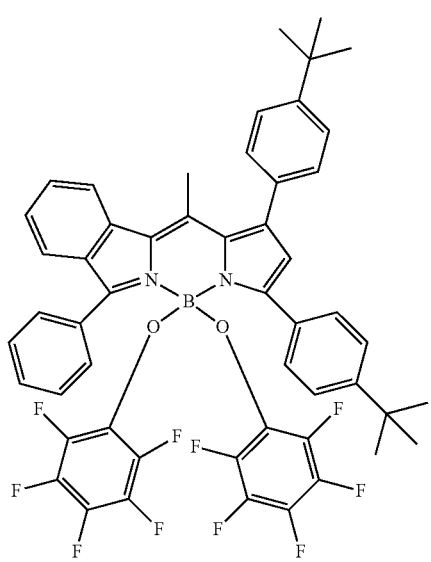
[II-38]
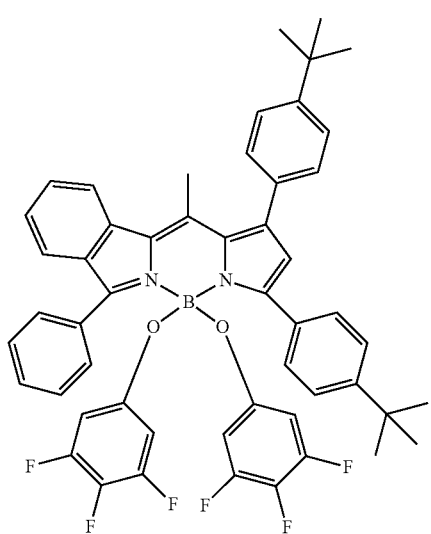
[II-39]
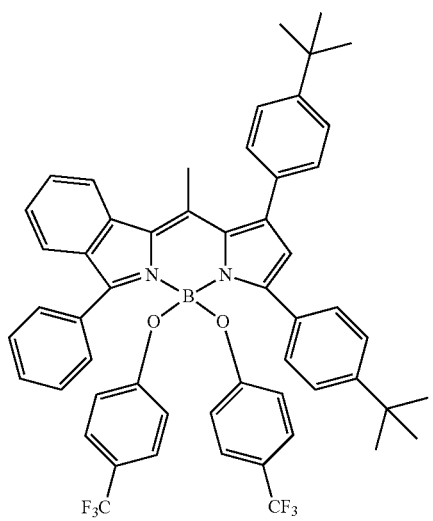
[II-40]
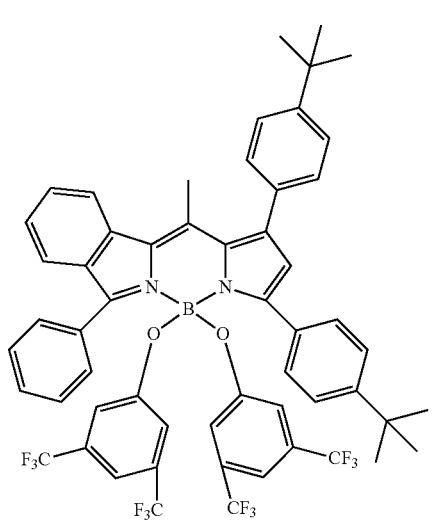
[II-41]
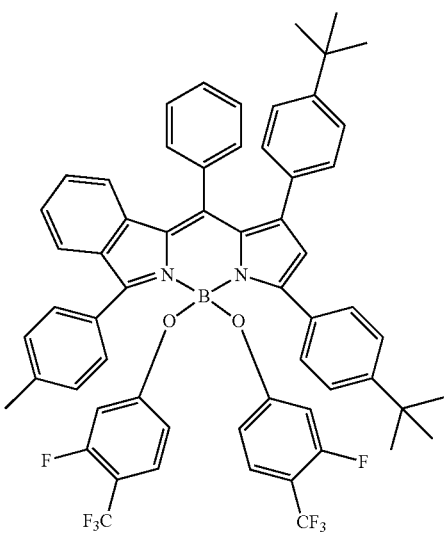

[II-42]
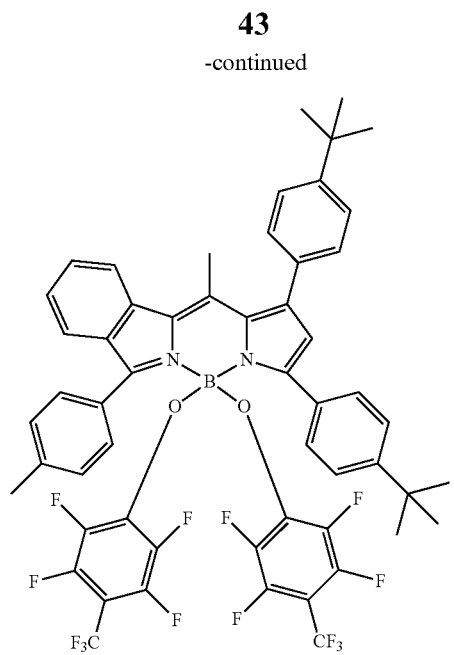
[II-43]
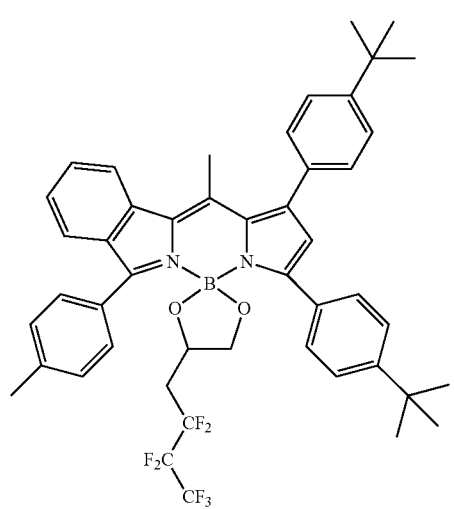
[II-44]
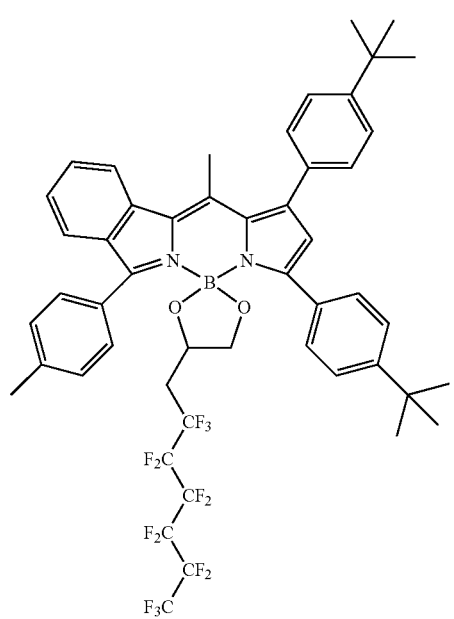
[II-45]
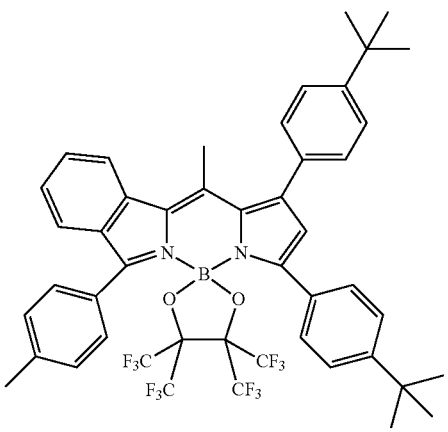
[II-46]
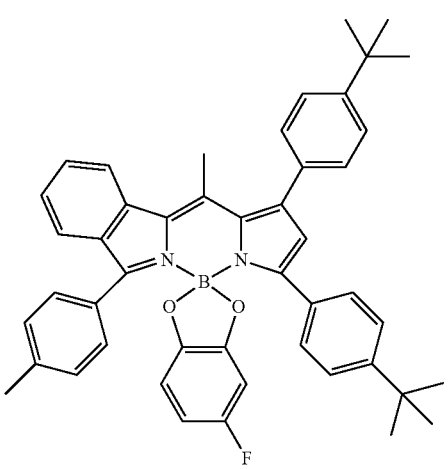
[II-47]
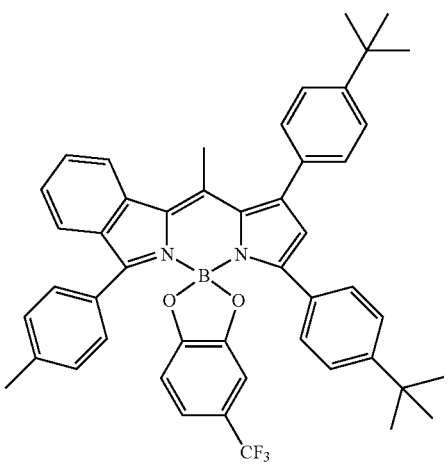

[II-48]
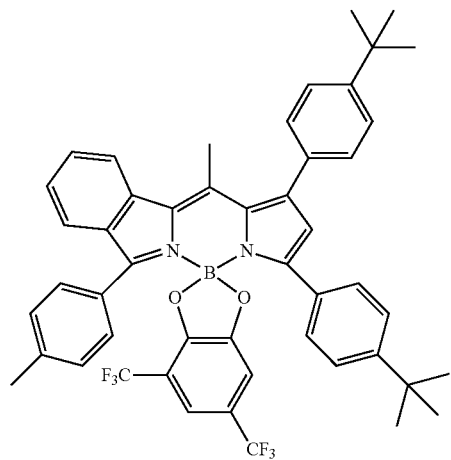
[II-49]
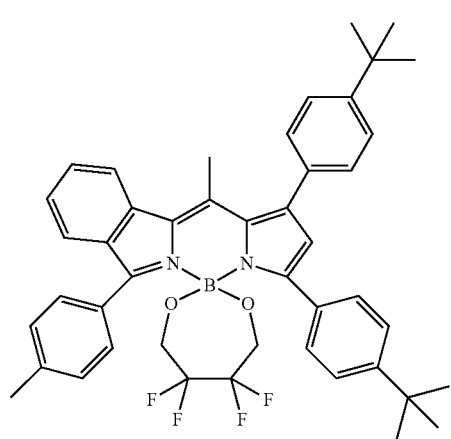
[II-50]
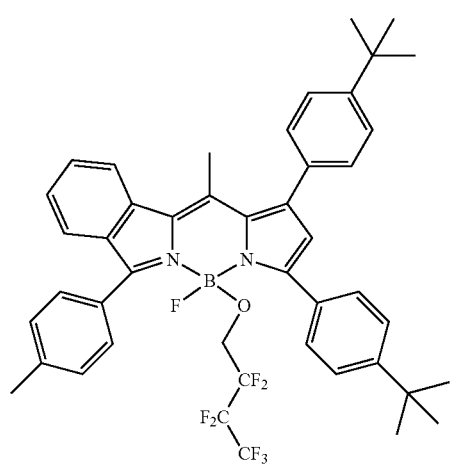
[II-52]
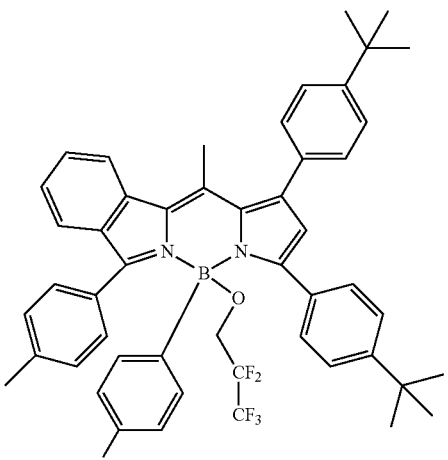
[II-53]
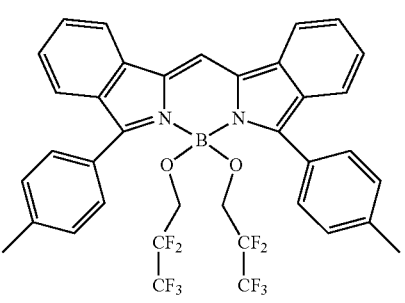
[II-54]
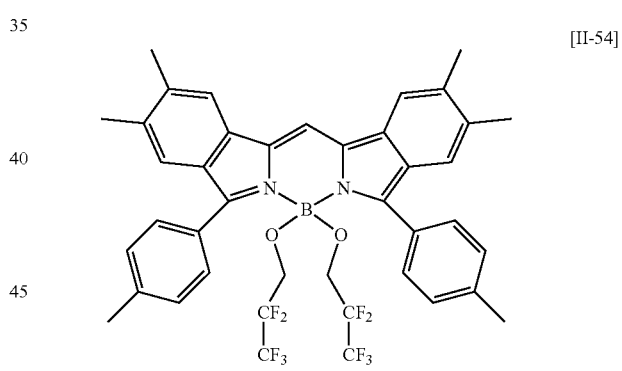
[II-55]
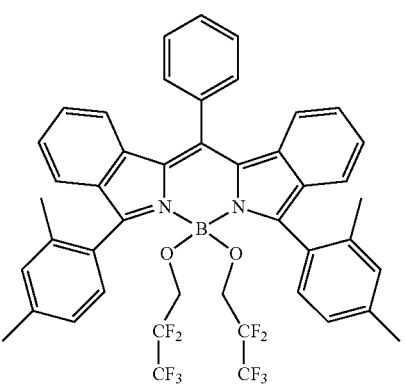

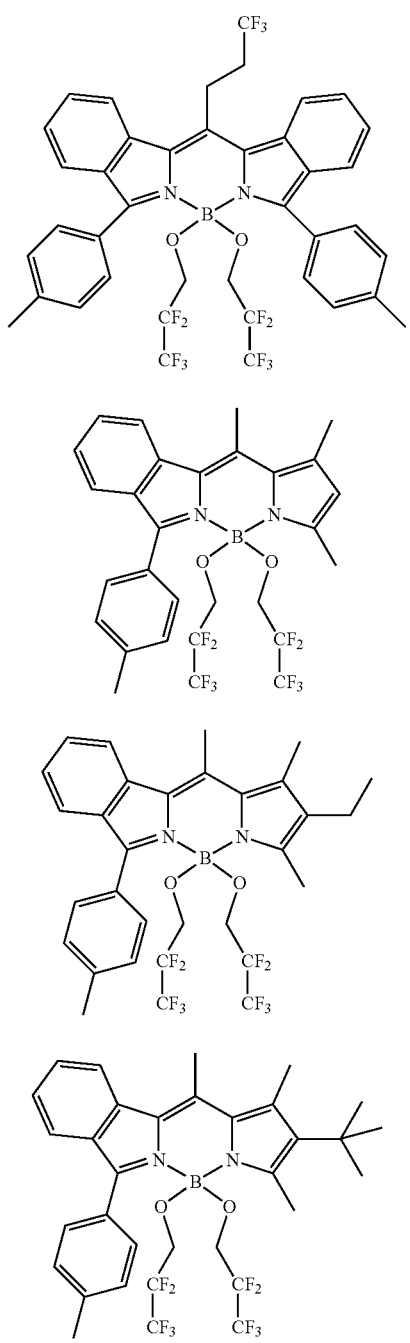

[II-56]

[II-57]

[II-58]

[II-59]

[II-60]

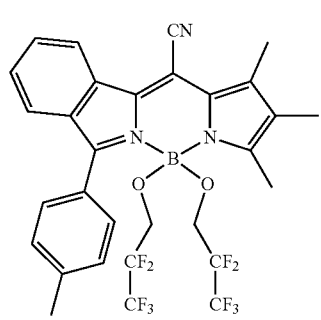

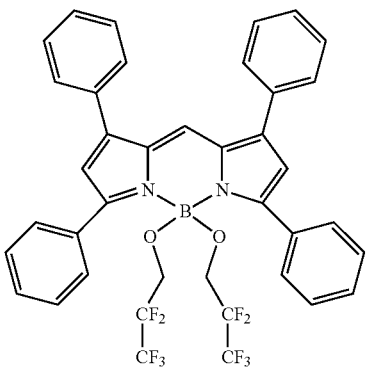

[III-1]

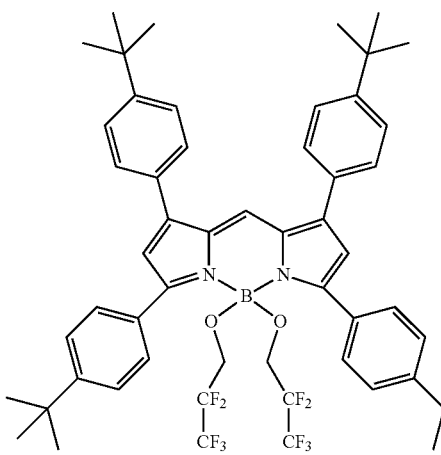

[III-2]

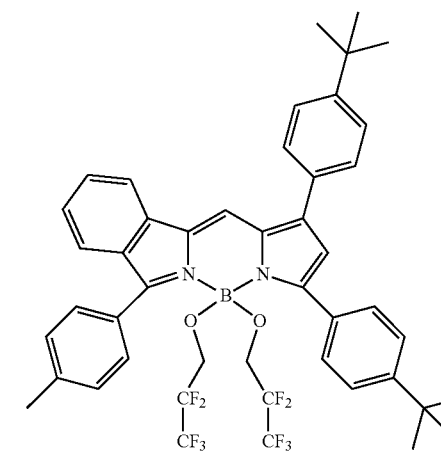

[III-3]

The method for producing the pyrromethene-boron complex compound of the invention represented by the formula (1) or (2) (hereinafter often simply referred to as the pyrromethene-boron complex compound of the invention) is not particularly restricted. The pyrromethene-boron complex compound of the invention can be produced by a known method.

The pyrromethene-boron complex compound of the invention can be produced by methods (A) and (B) in which substituents on boron of a known pyrromethene-boron complex are changed; method (C) in which boron into which a substituent has been incorporated in advance is coordinated in a pyrromethene ligand; and (D) combination of methods (A) and (B), and method (C).

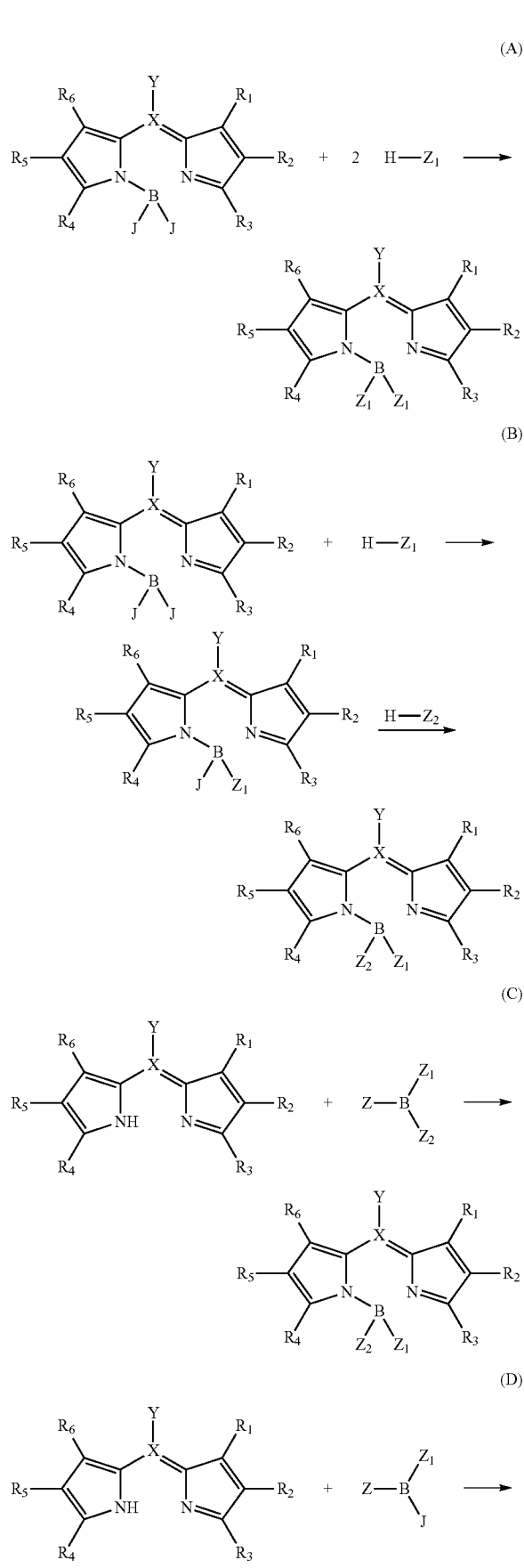

In the above-mentioned synthesis routes (A) to (D), J indicates a halogen atom.

The halogen atom shown by J is preferably chlorine, bromine or fluorine.

In the above-mentioned synthesis routes (A) to (D), various additives may be used in order to allow the reaction to be proceeded easily.

As the additive, a Lewis acid catalyst such as aluminum chloride, a basic catalyst such as triethylamine and diisopropylethylamine, alkaline metal salts or alkaline earth metal salts of the substituent Z or the like are appropriately used.

No particular restrictions are imposed on the reaction solvent used in the above-mentioned synthesis routes (A) to (D) insofar as it is a solvent which can dissolve the reaction raw material compounds and does not hinder the reaction. Specific examples of the solvent include chlorine-based hydrocarbon solvents such as methylene chloride and 1,2-dichloroethane; ether-based solvents such as diethyl ether, tetrahydrofuran, dimethoxyfuran and 1,4-dioxane; and aromatic hydrocarbon solvents such as benzene, toluene and xylene. As for the reaction temperature, an appropriate reaction temperature can be selected from room temperature to the boiling point of a solvent used according to the solubility or reactivity of the reaction raw material compound.

The pyrromethene-boron complex compound of the invention is preferably used as a material for an organic EL device, more preferably as a dopant in the emitting layer. By using the pyrromethene-boron complex compound of the invention, a red-emitting organic EL device which has a high luminous efficiency and a long life can be obtained.

When the pyrromethene-boron complex compound of the invention is used as a dopant, the pyrromethene-boron complex compound of the invention can realize an organic EL device which hardly suffers from concentration quenching even if the doping concentration is high.

In the organic EL device of the invention which comprises one or a plurality of organic thin film o layers containing at least an emitting layer between a pair of electrodes, at least one of the organic thin film layers comprises the pyrromethene-boron complex compound according to the invention.

The above-mentioned organic thin film layer may contain one kind of the pyrromethene-boron complex compound of the invention or may contain two or more kinds of the pyrromethene-boron complex compound of the invention in combination.

In the organic EL device of the invention, the emitting layer preferably comprises the pyrromethene-boron complex compound of the invention. The pyrromethene-boron complex compound of the invention may be used as a host material of the emitting layer, but it is preferably used as a dopant of the emitting layer.

The pyrromethene-boron complex compound of the invention has a small doping concentration dependency on the luminous efficiency or the shape of the spectrum. The doping concentration of the pyrromethene-boron complex compound of the invention is preferably 20 wt % or less, more preferably 5 wt % or less.

When the pyrromethene-boron complex compound of the invention is used in the emitting layer, the emitting layer further comprises a naphthacene derivative represented by the following formula (3). The naphthacene derivative represented by the following formula (3) can function as a host material.

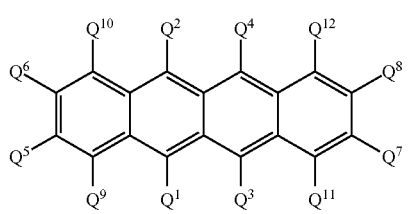
(3)

wherein $Q^1$ to $Q^{12}$ are independently a hydrogen atom, a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms.

In the naphthacene derivative represented by the above formula (3), it is preferred that at least one of $Q^1$, $Q^2$, $Q^3$ and $Q^4$ be an aryl group.

The naphthacene derivative represented by the above formula (3) is preferably a naphthacene derivative represented by the following formula (4):

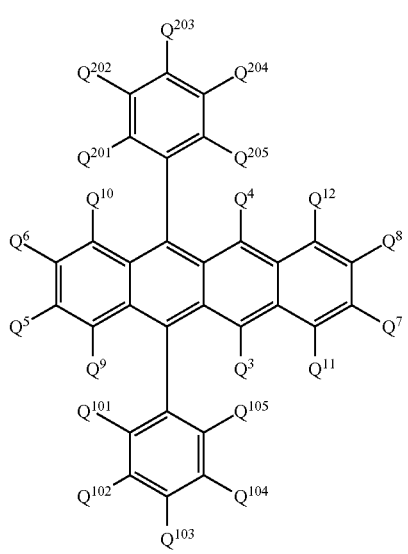
(4)

wherein $Q^3$ to $Q^{12}$ are the same as those in the formula (3), $Q^{101}$ to $Q^{105}$ and $Q^{201}$ to $Q^{205}$ are independently a hydrogen atom, a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms, and adjacent substituents of $Q^{101}$ to $Q^{105}$ and $Q^{201}$ to $Q^{205}$ may form a ring.

In the naphthacene derivative represented by the above formula (4), it is preferred that at least one of $Q^{101}$, $Q^{105}$, $Q^{201}$ and $Q^{205}$ be a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms.

Specific examples of the naphthacene derivative represented by the formula (3) or (4) (hereinafter often referred to as the naphthacene derivative of the invention) are given below.

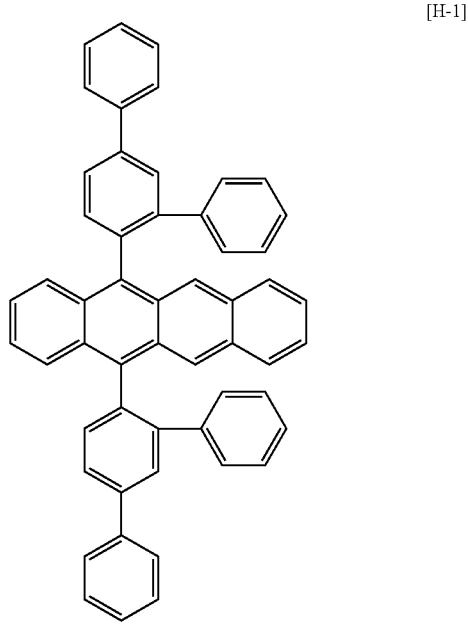
[H-1]

[H-2]

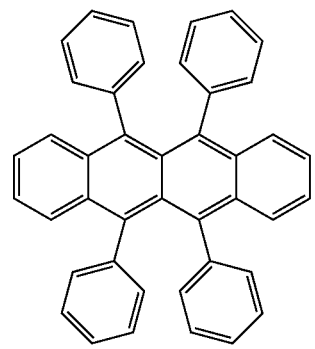

[H-3]

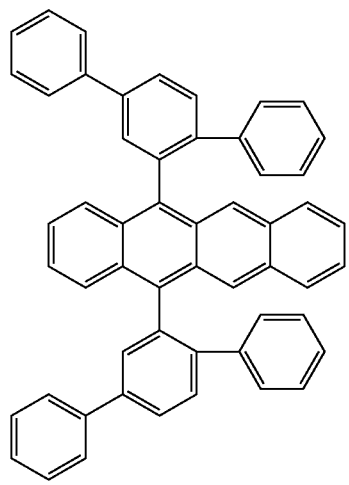

[H-4]

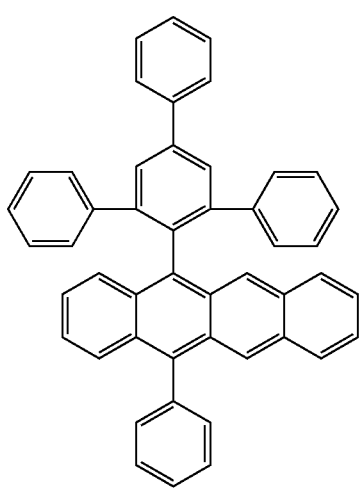

[H-5]

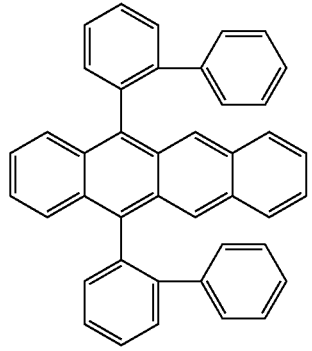

As the organic EL device of the invention in which the organic thin film layer is composed of plural layers, one in which an anode, a hole-injecting layer, an emitting layer and a cathode are sequentially stacked (anode/hole-injecting layer/emitting layer/cathode), one in which an anode, an emitting layer, an electron-injecting layer and a cathode are sequentially stacked (anode/emitting layer/electron-injecting layer/cathode), one in which an anode, a hole-injecting layer, an emitting layer, electron-injecting layer and a cathode are sequentially stacked (anode/hole-injecting layer/emitting layer/electron-injecting layer/cathode) or the like can be given.

If necessary, to the above-mentioned plural layers, in addition to the pyrromethene-boron complex compound of the invention, a further known emitting material, a dopant, a hole-injecting material or an electron-injecting material can be used.

By allowing the organic thin film layer to be composed of plural layers, the organic EL device can be prevented from a lowering of luminance or lifetime due to quenching. Further, depending of the kind of the dopant used, luminance or luminous efficiency can be improved or red or blue emission can be obtained.

The hole-injecting layer, the emitting layer and the electron-injecting layer, which are the organic thin film layers, may respectively be formed of two or more layers.

If the hole-injecting layer is formed of two or more layers, a layer which injects holes from an electrode is referred to as a hole-injecting layer, and a layer which receives holes from the hole-injecting layer and transports the holes to the emitting layer is referred to as a hole-transporting layer. Similarly, if the electron-injecting layer is formed of two or more layers, a layer which injects electrons from an electrode is referred to as an electron-injection layer and a layer which receives electrons from an electron-injecting layer and transports the electrons to the emitting layer is referred to as an electron-transporting layer.

Each of these layers is selected and used according to each of the factors, i.e. the energy level, heat resistance, adhesiveness to the organic layer or the metal electrode or the like.

Examples of the host material or the dopant which can be used in the emitting layer together with the pyrromethene-boron complex compound of the invention except for the naphthacene derivative of the invention include fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, 1,4-bis(9'-ethynylanthracenyl)benzene, and the derivatives thereof, organic metal complexes such as tris(8-quinolinolate)aluminum, bis-(2-methyl-8-quinolinolate)-4-(phenylphenolinate)aluminum, triarylamine derivatives, styrylamine derivatives, stilbene derivatives, coumarin derivatives, pyrane derivatives, oxazoline derivatives, benzothiazole derivatives, benzoxazole derivatives, benzimidazole derivatives, pyrazine derivatives, cinnamate derivatives, diketo-pyrrolo-pyrrole derivatives, acridone derivatives and quinacridone derivatives or the like.

As the hole-injecting material, a compound which can transport holes, exhibits hole-injecting effects from the anode and excellent hole-injection effect for the emitting layer or the emitting material, prevents excitons generated in the emitting layer from moving to the electron-injecting layer or the electron-injecting material, and has an excellent capability of forming a thin film is preferable.

Specific examples thereof include, though not limited thereto, phthalocyanine derivatives, naphthalocyanine derivatives, porphyline derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine-type triphenylamine, styrylamine-type triphenylamine, diamine-type triphenylamine, derivatives thereof, and polymer materials such as polyvinyl carbazole, polysilane and conductive polymers.

It is also possible to sensitize the hole-injecting material by adding an electron-accepting substance.

The hole-injecting materials usable in the organic EL device of the invention are preferably aromatic tertiary amine derivatives and phthalocyanine derivatives.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or a polymer having these aromatic tertiary amine skeleton.

Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, Cl2SiPc, (HO)AlPc, (HO)GaPc, VOPc, TiOPc, MoOPc and GaPc-O—GaPc.

In the organic EL device of the invention, it is preferred that a layer containing these aromatic tertiary amine derivatives and/or phthalocyanine derivatives, for example, the above-mentioned hole-transporting layer and/or the hole-injecting layer, be formed between the emitting layer and the anode.

The electron-injecting material is preferably a compound which can transport electrons, exhibits electron-injecting effects from the cathode and excellent electron-injection effects for the emitting layer or the emitting material, prevents excitons generated in the emitting layer from moving to the hole-injecting layer, and has an excellent capability of forming a thin film.

Specific examples of the electron-injecting material include fluorenone, anthraquinodimethane, diphenoquinone, thiopyran dioxide, oxazole, oxadiazole, triazole, imidazole, perylene tetracarboxylic acid, fluorenylidenemethane, anthraquinodimethane, anthrone and the derivatives thereof.

In addition, it is also possible to sensitize the electron-injecting material by adding an electron-donating material.

The electron-injecting material used in the organic EL device of the invention is preferably a metal complex compound and a nitrogen-containing five-membered ring derivative.

Examples of the metal complex compound include 8-hydroxyquinolinate lithium, bis(8-hydroxyquinolinate)zinc, bis(8-hydroxyquinolinate)copper, bis(8-hydroxyquinolinate) manganese, tris(8-hydroxyquinolinate)aluminum, tris(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate) zinc, bis(2-methyl-8-quinolinate)chlorogallium, bis(2-methyl-8-quinolinate)(o-crezolate)gallium, bis(2-methyl-8-quinolinate)(1-naphtholate)aluminum and bis(2-methyl-8-quinolinate)(2-naphtholate)gallium.

As the above-mentioned nitrogen-containing five-membered ring derivative, oxazole, thiazole, oxadiazole, thiadiazole and triazole derivatives can be preferably given. Specific examples thereof include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4''-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4''-biphenyl)-1,3,4-thiaziazole, 2,5-bis(1-naphthyl)-1,3,4-thiaziazole, 1,4-bis[2-(5-phenylthiazolyl)]benzene, 2-(4'-tert-butylphenyl)-5-(4''-biphenyl)-1,3,4-triazole, 2,5-bis(1-naphthyl)-1,3,4-triazole and 1,4-bis[2-(5-phenyltriazolyl)]benzene.

In the organic EL device of the invention, the emitting layer may contain, in addition to the above-mentioned pyrromethene-boron complex compound represented by the formula (1), at least one of an emitting material, a dopant, a hole-injecting material, and an electronic-injecting material in the same layer. Moreover, for improving stability of the organic EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable.

As the above-mentioned conductive material, carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole can be given.

As the conductive material used in the cathode, a conductive material having a work function of smaller than 4 eV is suitable.

As the above-mentioned conductive material, magnesium, calcium, tin, lead, titanium, yttrium, lithium, ruthenium, manganese, aluminum, and lithium fluoride or the like, and alloys thereof can be given.

Examples of the alloys include magnesium/silver alloys, magnesium/indium alloys and lithium/aluminum alloys. The amount ratio of the alloy is controlled by the temperature of the deposition source, atmosphere, vacuum degree or the like, and an appropriate ratio is selected.

If necessary, the anode and the cathode each may be a stacked body composed of two or more layers.

In the organic EL device of the invention, in order to allow it to emit light efficiently, it is preferred that at least one of the surfaces of the device be fully transparent in the emission wavelength region of the device. In addition, it is preferred that the substrate also be transparent.

As for the electrode, it suffices that a transparent electrode be set such that predetermined transparency can be ensured by a method such as deposition or sputtering by using the above-mentioned conductive materials. It is preferred that the electrode on the emitting surface have a light transmittance of 10% or more.

Although no specific restrictions are imposed on the substrate as long as it has mechanical and thermal strength and transparency, a glass substrate and a transparent resin film can be given.

Examples of the transparent resin film include polyethylene, an ethylene-vinyl acetate copolymer, an ethylene-vinyl alcohol copolymer, polypropylene, polystyrene, polymethylmethacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide and polypropylene.

Each layer of the organic EL device of the invention can be formed by a dry film-forming method such as vacuum vapor deposition, sputtering, plasma ion plating, ion plating or the like or a wet film-forming method such as spin coating, dipping, flow coating or the like.

In particular, in the case of the pyrromethene-boron complex compound of the invention, since it has a high volatility and can be deposited at a lower temperature, it hardly suffers thermal decomposition even heated for a long period of time.

In the case of the wet film-forming method, a thin film is formed by using a solution formed by dissolving or dispersing materials forming each layer in various solvents, for example.

No specific restrictions are imposed on the above-mentioned solvents insofar as it is a solvent which can dissolve or disperse a solute preferably. For example, alkanes such as n-decane, cyclohexane, ethyl cyclohexane, decaline, and bicyclohexane; aromatic hydrocarbons such as toluene, xylene, methycylene, cyclohexylbenzene and tetralin; halogenated aromatic hydrocarbons such as chlorobenzene, dichlorobenzene and trichlorobenzene; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylanisole, and diphenyl ether; aromatic esters such as phenyl acetate, phenyl propionate, methyl benzoate, ethyl benzoate, ethyl benzoate, propyl benzoate and n-butyl benzoate; alicyclic ketones such as cyclohexanone, cyclooctanone and fenchone; alicyclic alcohols such as cyclohexanol and cyclooctanol; aliphatic ketones such as methyl ethyl ketone and dibutyl ketone; aliphatic alcohols such as butanol and hexanol; and aliphatic ethers such as ethylene glycol dimethyl ether, ethylene glycol diethylether and propylene glycol 1-monomethyl ether acetate (PGMEA), can be given.

Although the film thickness is not particularly limited, it is required to adjust the film thickness to an appropriate value. The suitable film thickness is normally 5 nm to 10 μm, with a range of 10 nm to 0.2 μm being preferable. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied.

In any of the organic thin film layers, an appropriate resin or an appropriate additive may be used in order to improve film-forming properties and to prevent generation of pinholes in the film or for other purposes.

Usable resins include insulative resins such as polystyrene, polycarbonate, polyarylate, polyester, polyamide, polyurethane, polysulfone, polymethyl methacrylate, polymethyl acrylate, cellulose or the like and copolymers thereof, photoconductive resins such as poly-N-vinylcarbazole and polysilane and conductive resins such as polythiophene and polypyrrole. As examples of the additive, antioxidants, UV absorbers, plasticizers or the like can be given.

EXAMPLES

The invention will be explained in more detail with reference to Examples given below.

The structural formulas of dopants D-1 to D-15 used in Examples and Comparative Examples, comparative compounds C-1 to C-15 which are intermediates of the dopants D-1 to D-15, host compounds H-1 to H-5, hole-injecting materials HI, hole-transporting material HT and electron-transporting material ET are shown below.

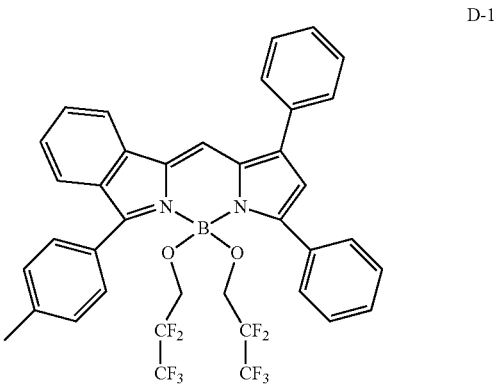

D-1

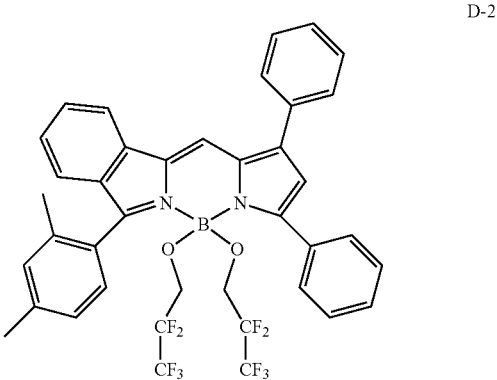

D-2

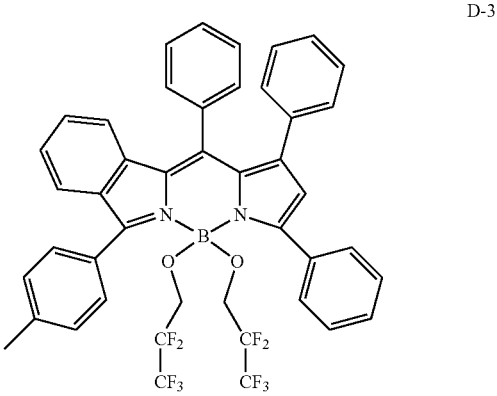

D-3

D-4
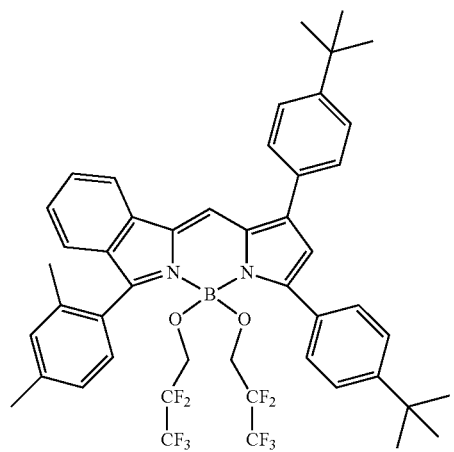
D-5
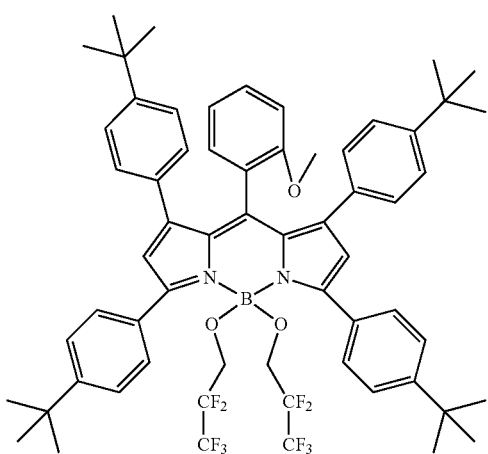
D-6
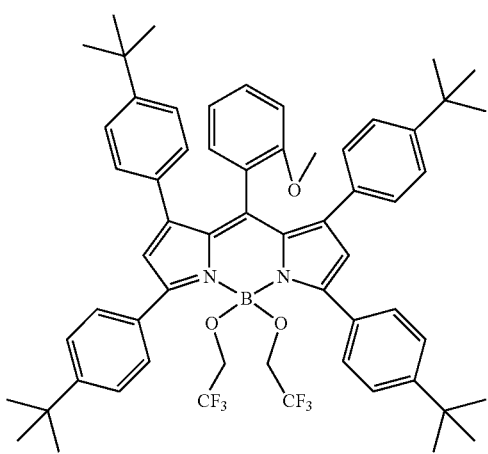
D-7
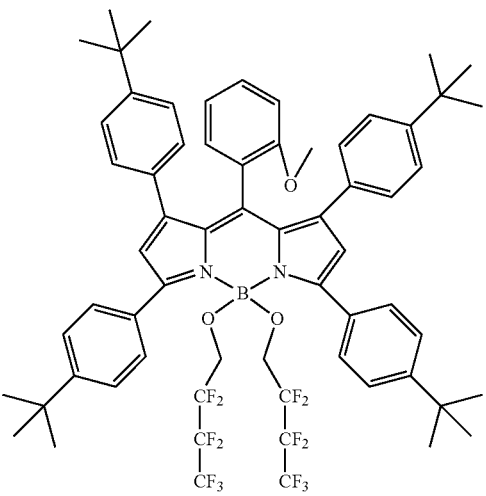
D-8
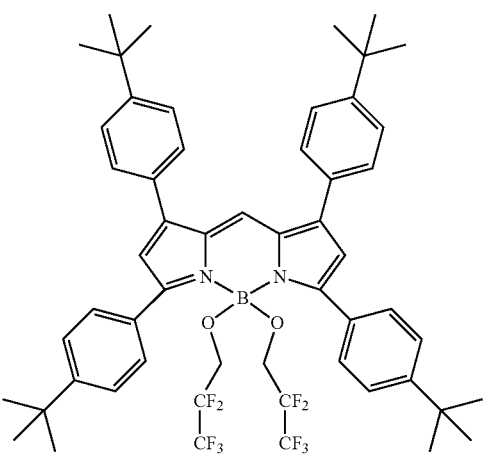
D-9
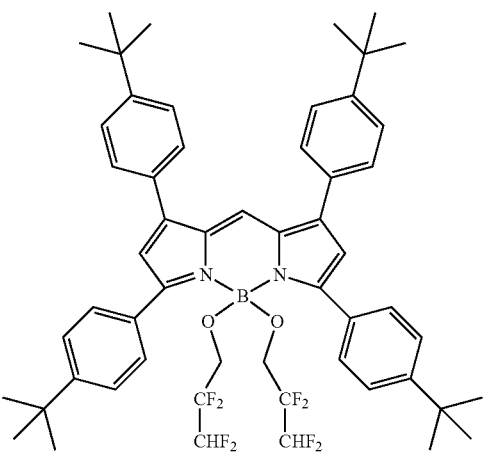

D-10
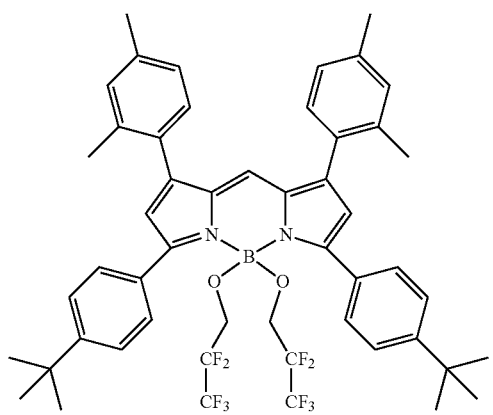
D-11
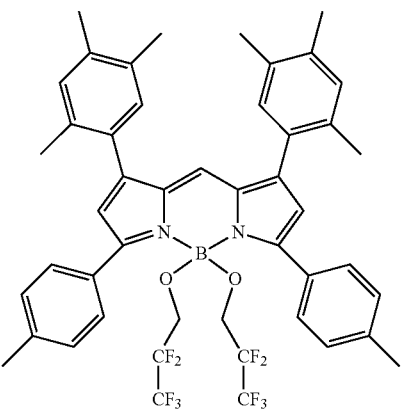
D-12
D-13
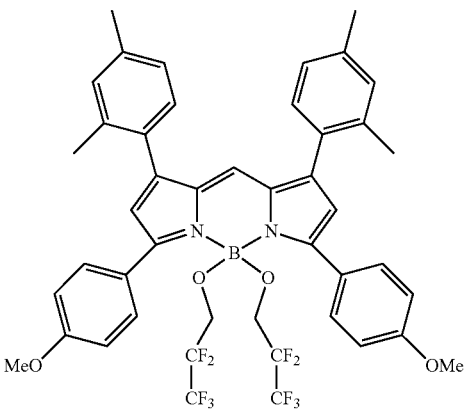
D-14
D-15
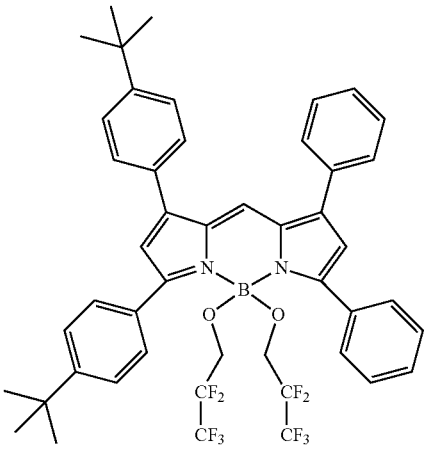
C-1
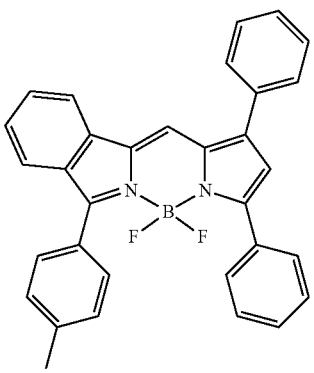

C-2
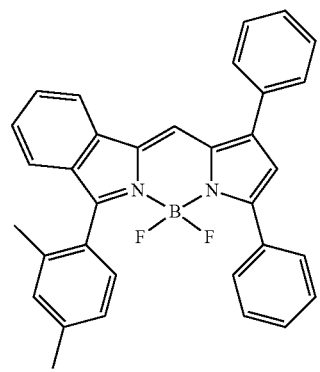
C-5
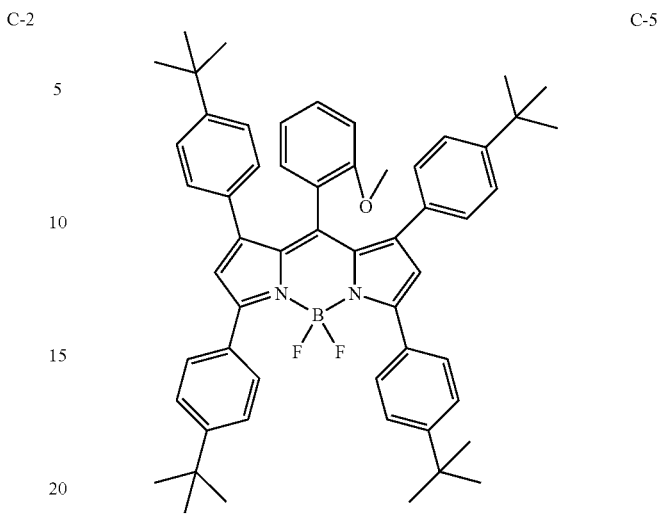
C-3
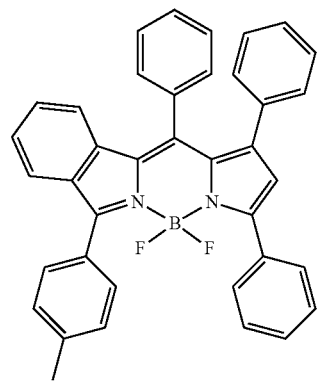
C-8
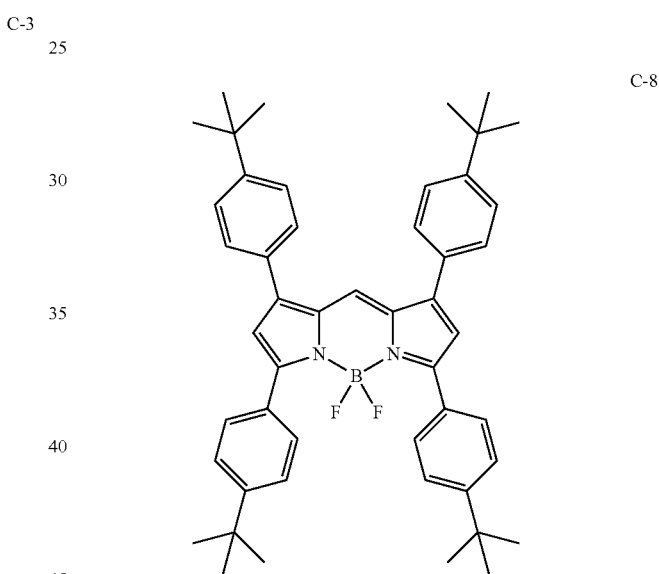
C-4
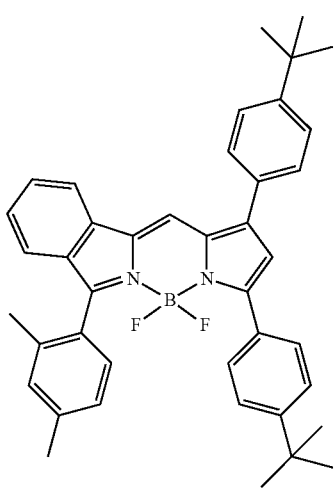
C-10
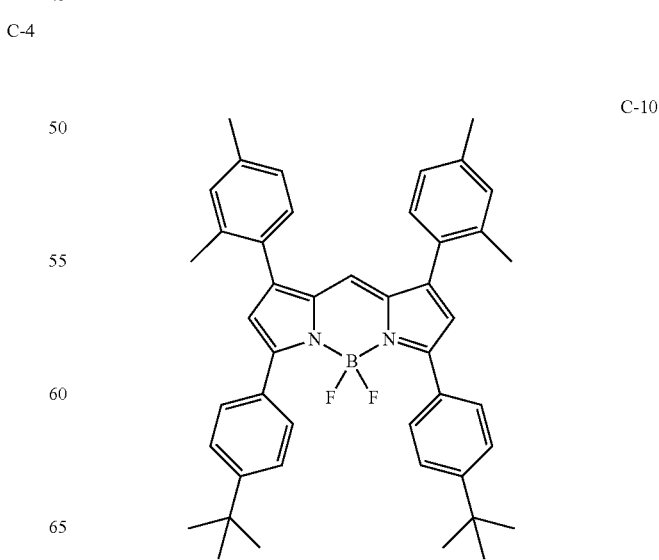

-continued
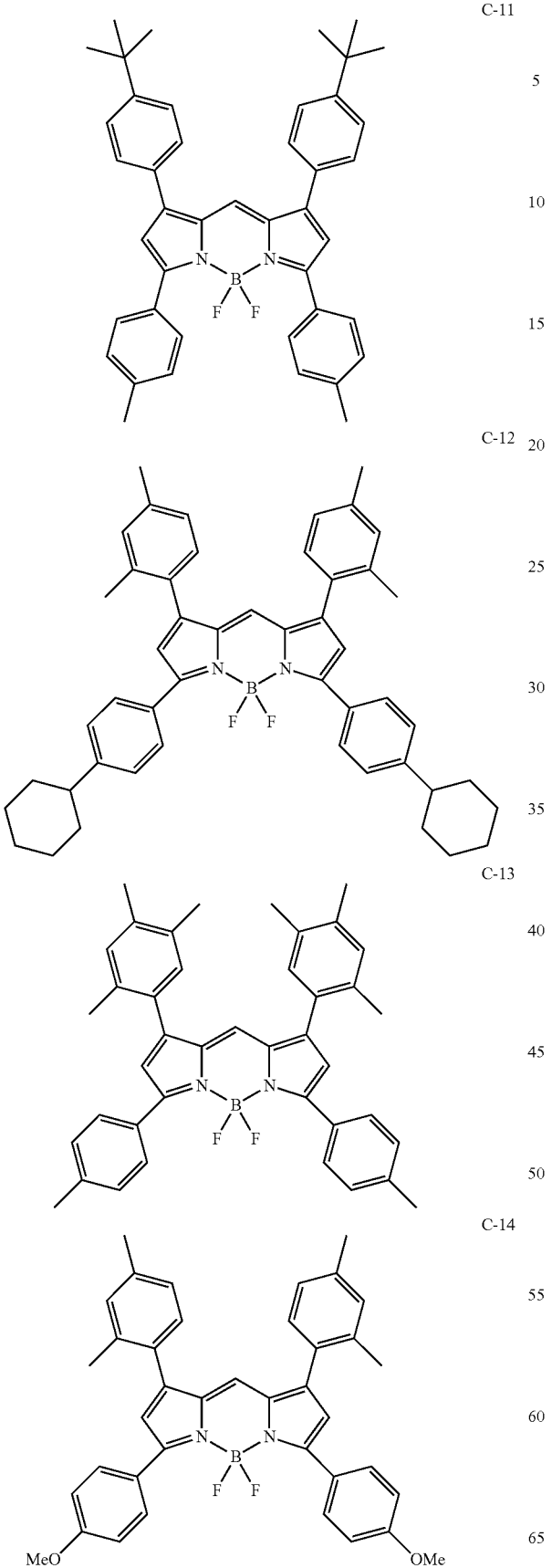
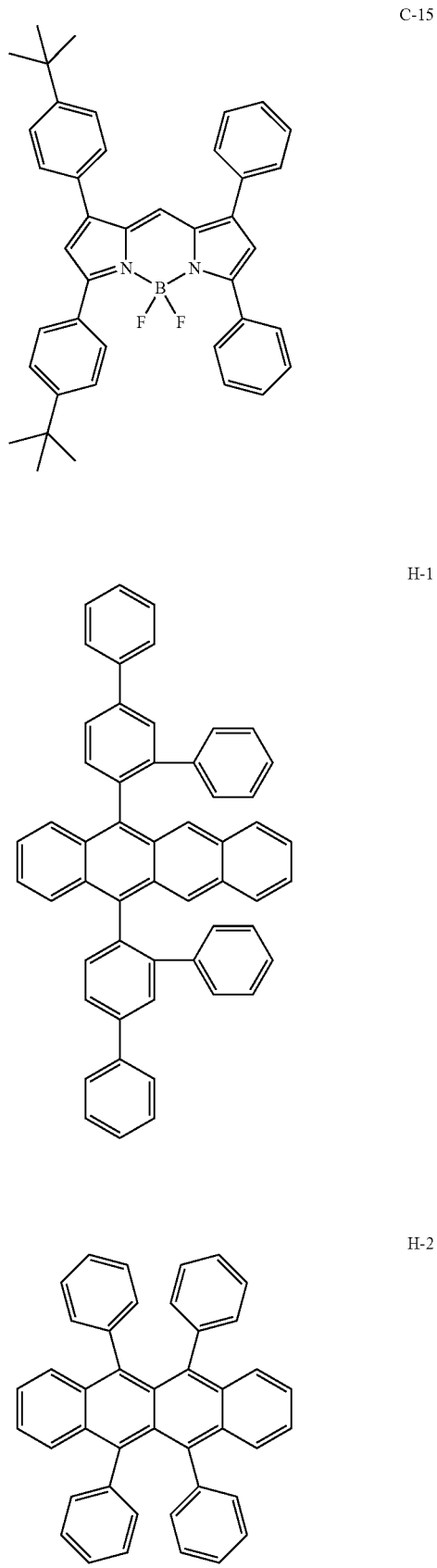

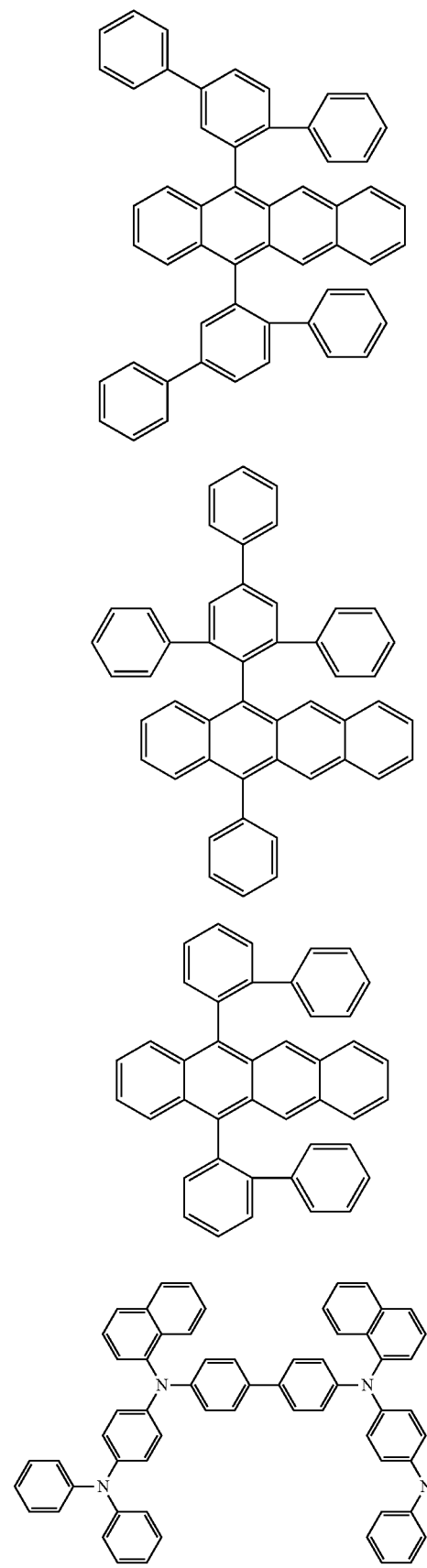

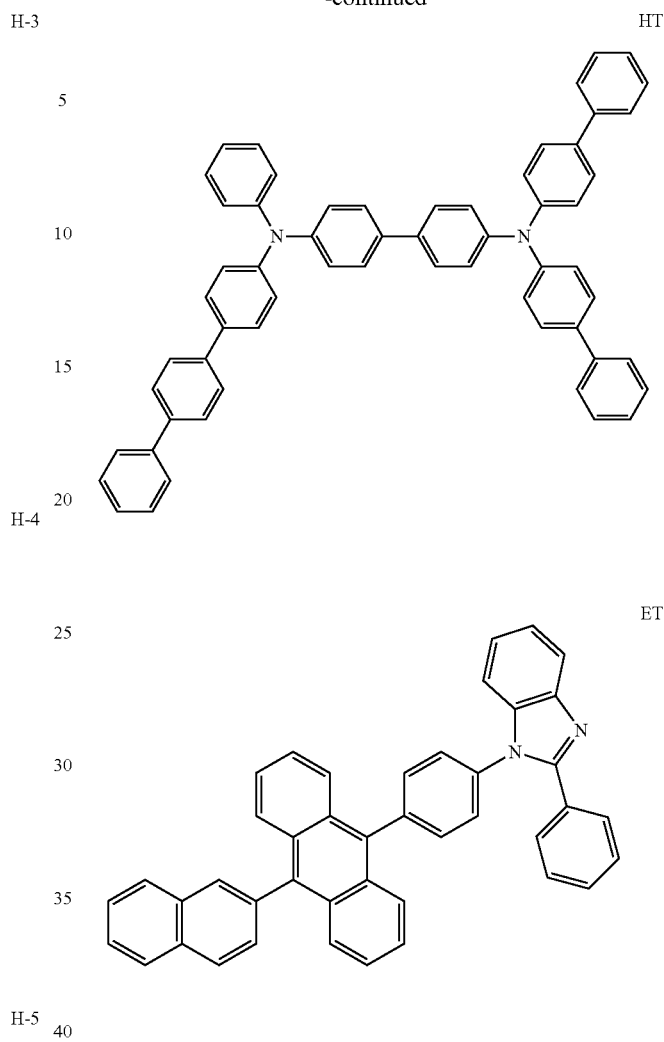

Synthesis Example 1

Synthesis of Compound D-1

15 g (100 mmol) of 2,2,3,3,3-pentafluoropropanol was diluted with 20 mL of 1,2-dimethoxyethane. 0.46 g (20 mmol) of metallic sodium was added in small quantities thereto to cause a reaction, whereby a solution of sodium salt was prepared.

0.97 g (2.0 mmol) of compound C-1 synthesized by a known method was dissolved in 60 mL of 1,2-dimethoxyethane, and the solution of a sodium salt prepared above was gradually added to the to resulting solution at room temperature. Then, while increasing the temperature gradually, the mixture was reacted by heating under reflux for 12 hours. After cooling the mixture to room temperature, the solvent was distilled away under reduced pressure. A residue was dissolved by adding 50 mL of methylene chloride. After washing with water, drying and concentrating, the solvent was distilled away under reduced pressure again. The residue was purified by means of silica-gel chromatography to obtain 0.80 g of reddish violet powder. From the H-NMR spectrum (FIG. 1) and a FD-MS spectrum (molecular ion m/Z=744), the reddish violet powder obtained was confirmed to be compound D-1.

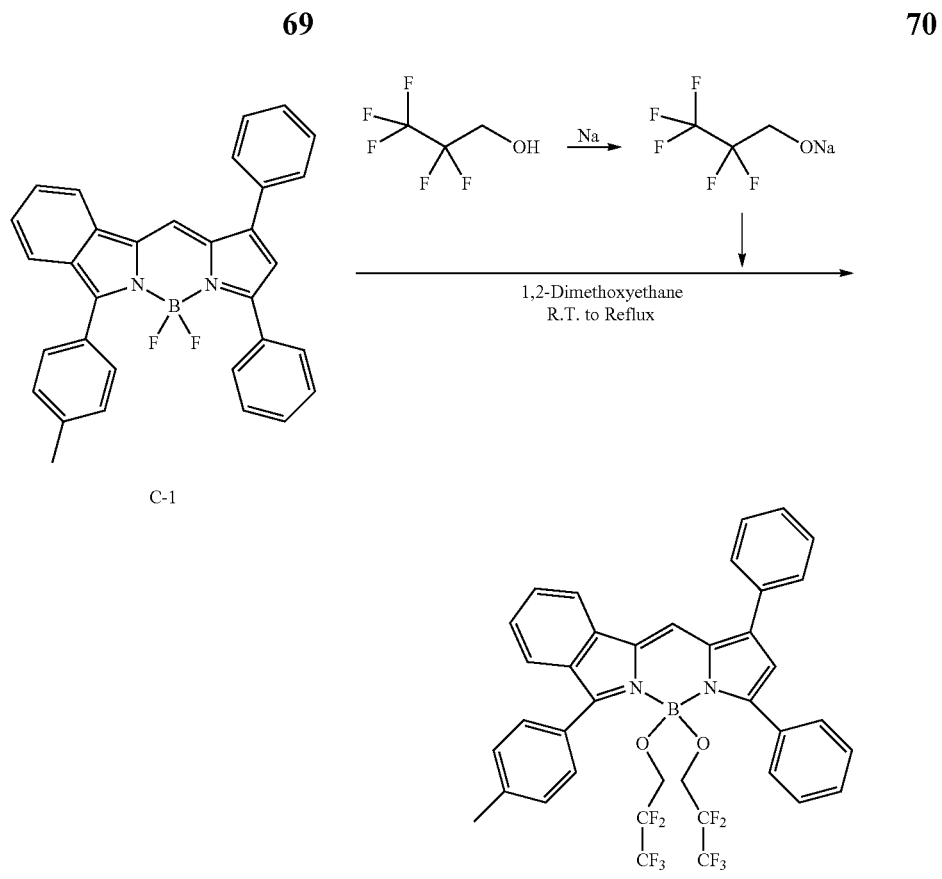

C-1

D-1

Synthesis Example 2

Synthesis of Compound D-2

Compound D-2 was synthesized in the same manner as in Synthesis Example 1, except that compound C-2 synthesized by a known method was used instead of compound C-1.

Figure 2:
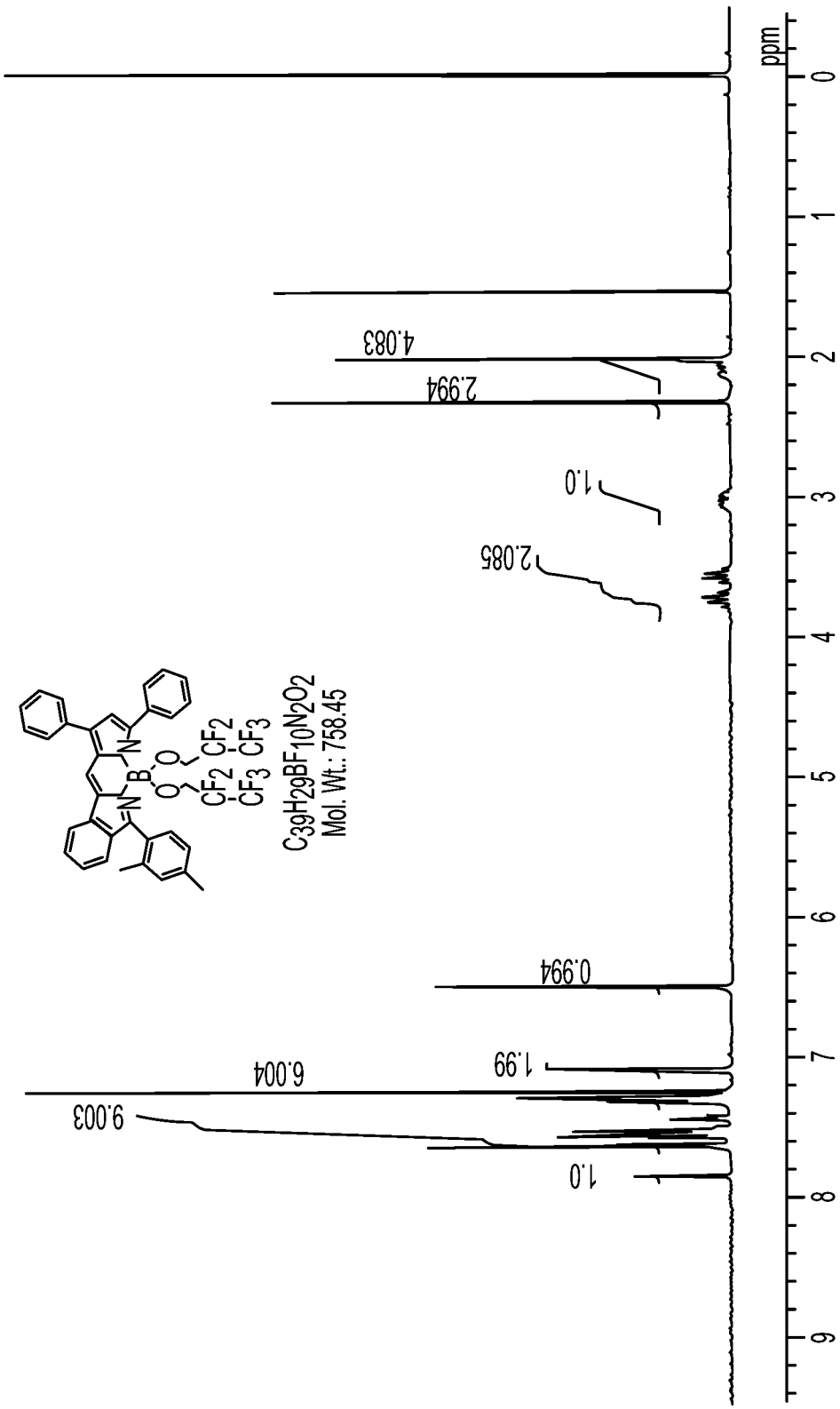
FIG. 2 is an H-NMR spectrum of the compound D-2 synthesized in Synthesis Example 2.

The structure of compound D-2 obtained was confirmed by the H-NMR spectrum (FIG. 2) and the FD-MS spectrum (molecular ion m/Z=758).

Synthesis Example 3

Synthesis of Compound D-3

Compound D-3 was synthesized in the same manner as in Synthesis Example 1, except that compound C-3 synthesized by a known method was used instead of compound C-1.

Figure 3:
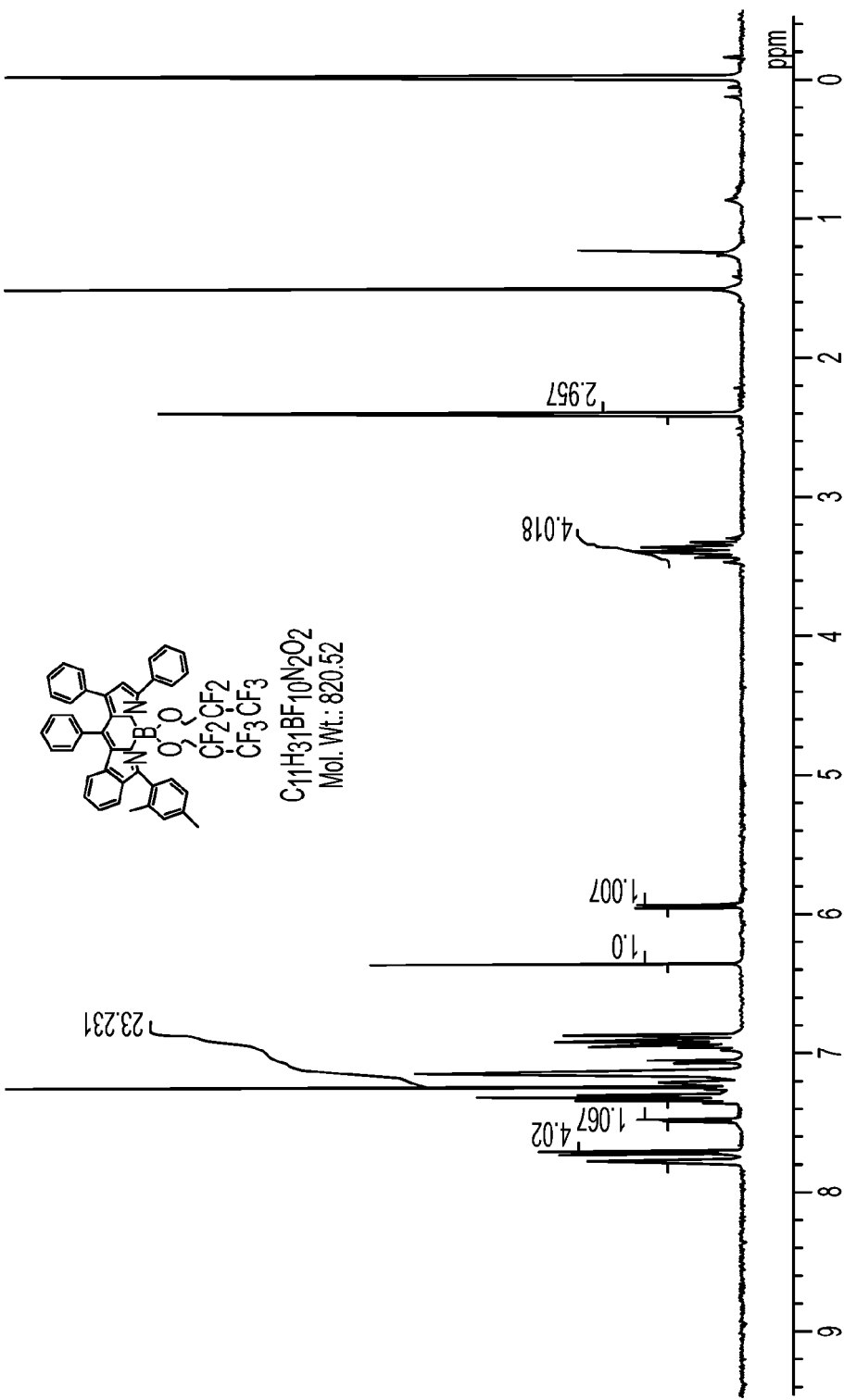
FIG. 3 is an H-NMR spectrum of the compound D-3 synthesized in Synthesis Example 3.

The structure of compound D-3 obtained was confirmed by the H-NMR spectrum (FIG. 3) and the FD-MS spectrum (molecular ion m/Z=820).

Synthesis Example 4

Synthesis of Compound D-4

Compound D-4 was synthesized in the same manner as in Synthesis Example 1, except that compound C-4 synthesized by a known method was used instead of compound C-1.

Figure 4:
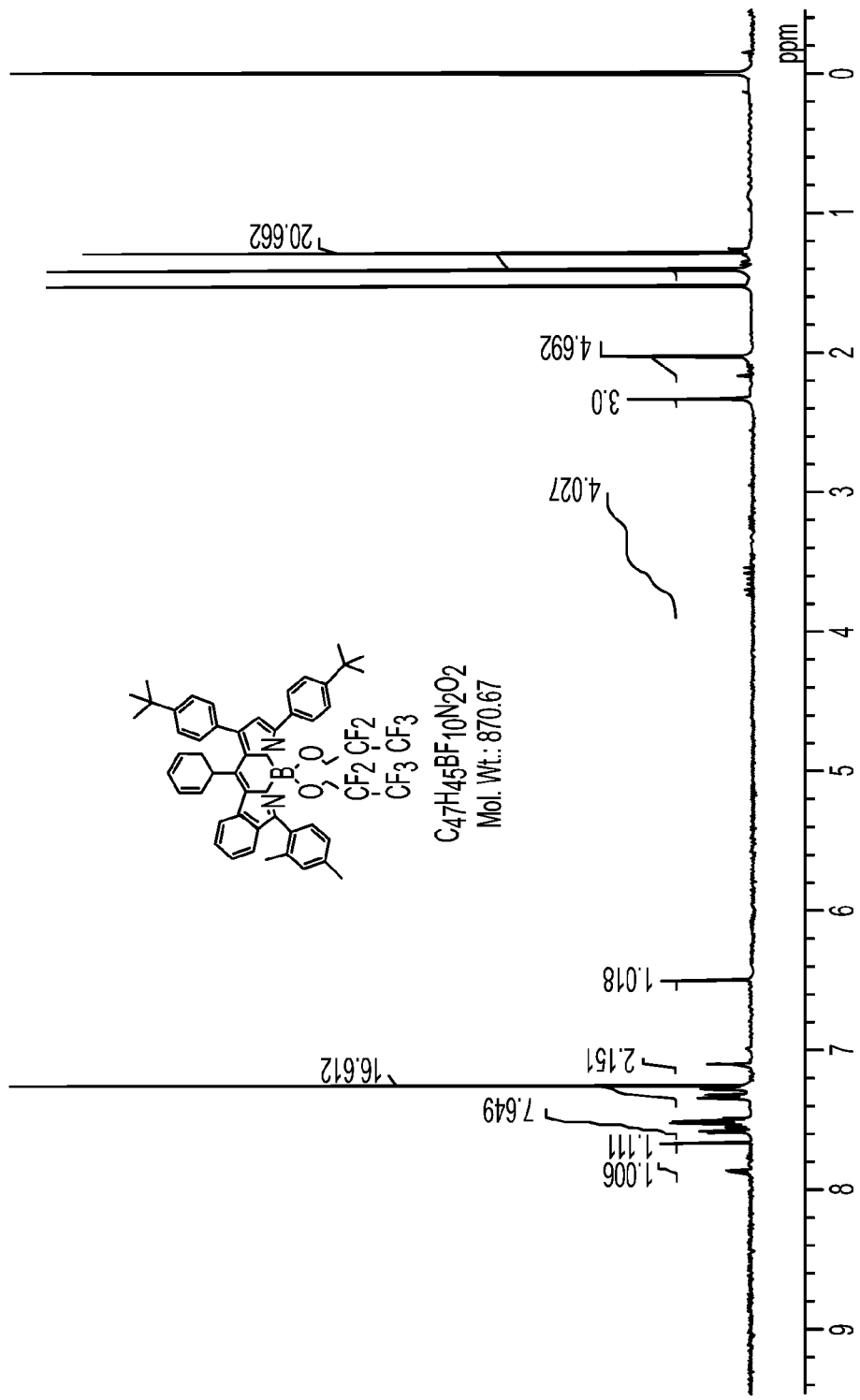
FIG. 4 is an H-NMR spectrum of the compound D-4 synthesized in Synthesis Example 4.

The structure of the compound D-4 obtained was confirmed by the H-NMR spectrum (FIG. 4) and the FD-MS spectrum (molecular ion m/Z=870).

Synthesis Example 5

Synthesis of Compound D-5

Figure 5:
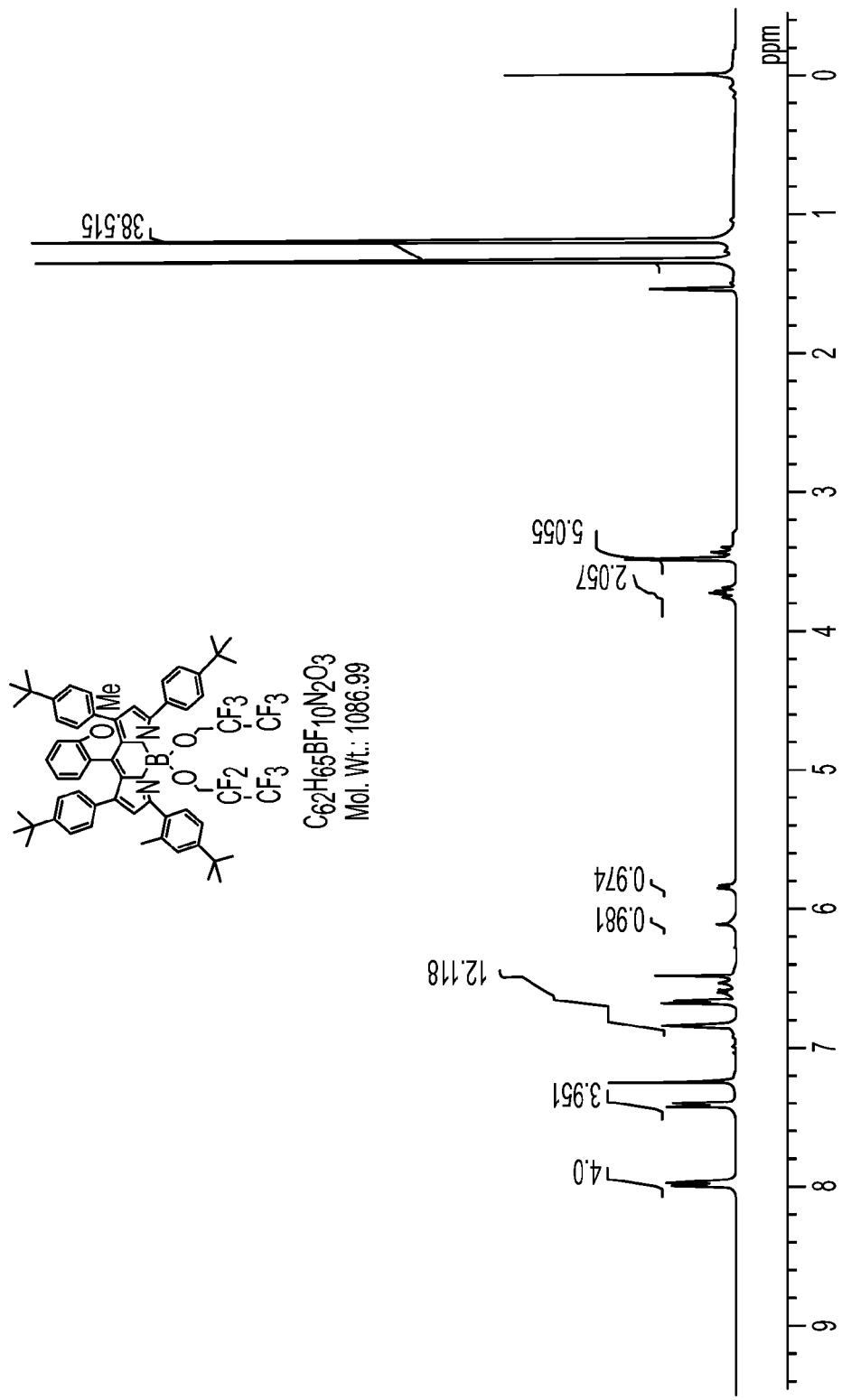
FIG. 5 is an H-NMR spectrum of the compound D-5 synthesized in Synthesis Example 5.

1.24 g (1.5 mmol) of compound C-5 synthesized by a known method and 9 g (60 mmol) of 2,2,3,3,3-pentafluoropropanol were dissolved in 60 mL of 1,2-dimethoxyethane. To this solution, 20 mL of a 1.6M hexane solution of n-butyllithium was gradually added at room temperature, and the resulting mixture was allowed to react at room temperature for further 5 hours. The solvent was distilled away under reduced pressure. The residue was dissolved by adding 50 mL of methylene chloride. After washing with water, drying and concentrating, the solvent was distilled away under reduced pressure again. The residue was purified by means of silica-gel chromatography to obtain 0.93 g of reddish violet powder. By the H-NMR spectrum (FIG. 5) and the FD-MS spectrum (molecular ion m/Z=1086), the reddish violet powder obtained was confirmed to be compound D-5.

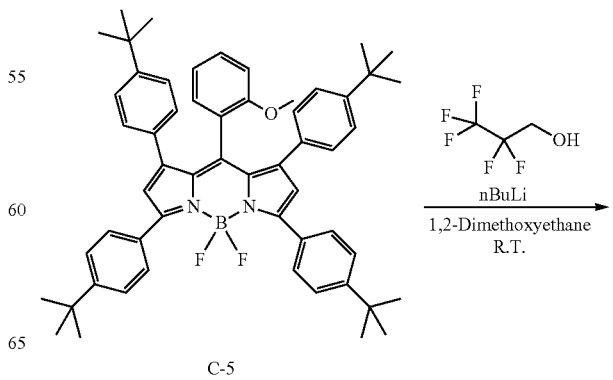

C-5

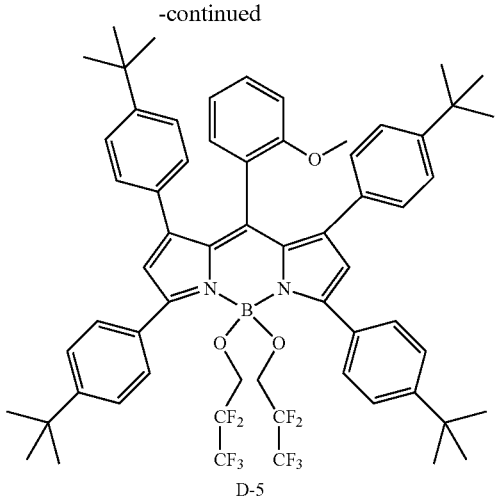

D-5

Synthesis Example 6

Synthesis of Compound D-6

Compound D-6 was synthesized in the same manner as in Synthesis Example 5, except that 2,2,2-trifluoroethanol was used instead of 2,2,3,3,3-pentafluoropropanol.

Figure 6:
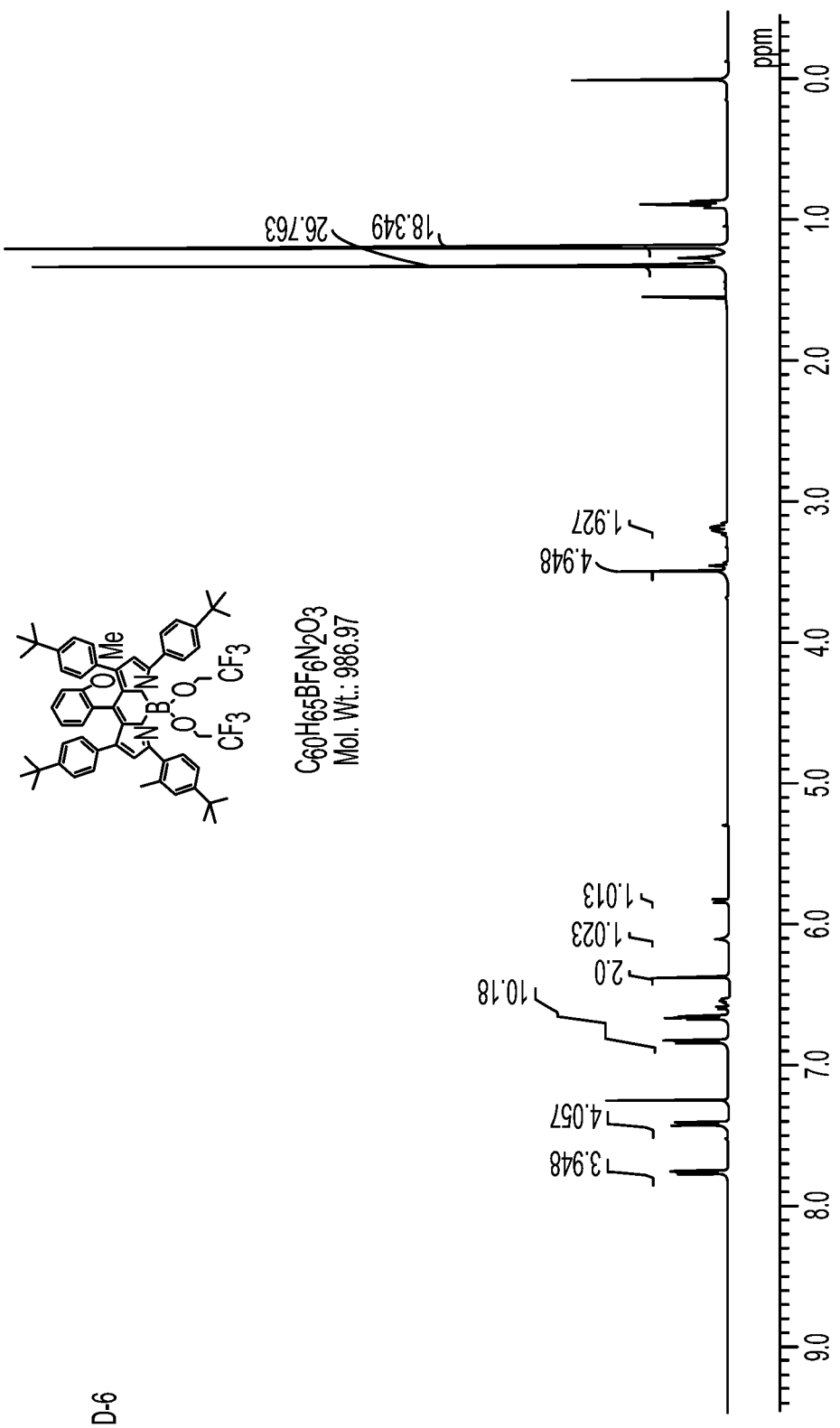
FIG. 6 is an H-NMR spectrum of the compound D-8 synthesized in Synthesis Example 6.

The structure of compound D-6 obtained was confirmed by the H-NMR spectrum (FIG. 6) and the FD-MS spectrum (molecular ion m/Z=986).

Synthesis Example 7

Synthesis of Compound D-7

Compound D-7 was synthesized in the same manner as in Synthesis Example 5, except that 2,2,3,3,4,4,4-heptafluorobutanol was used instead of 2,2,3,3,3-pentafluoropropanol.

Figure 7:
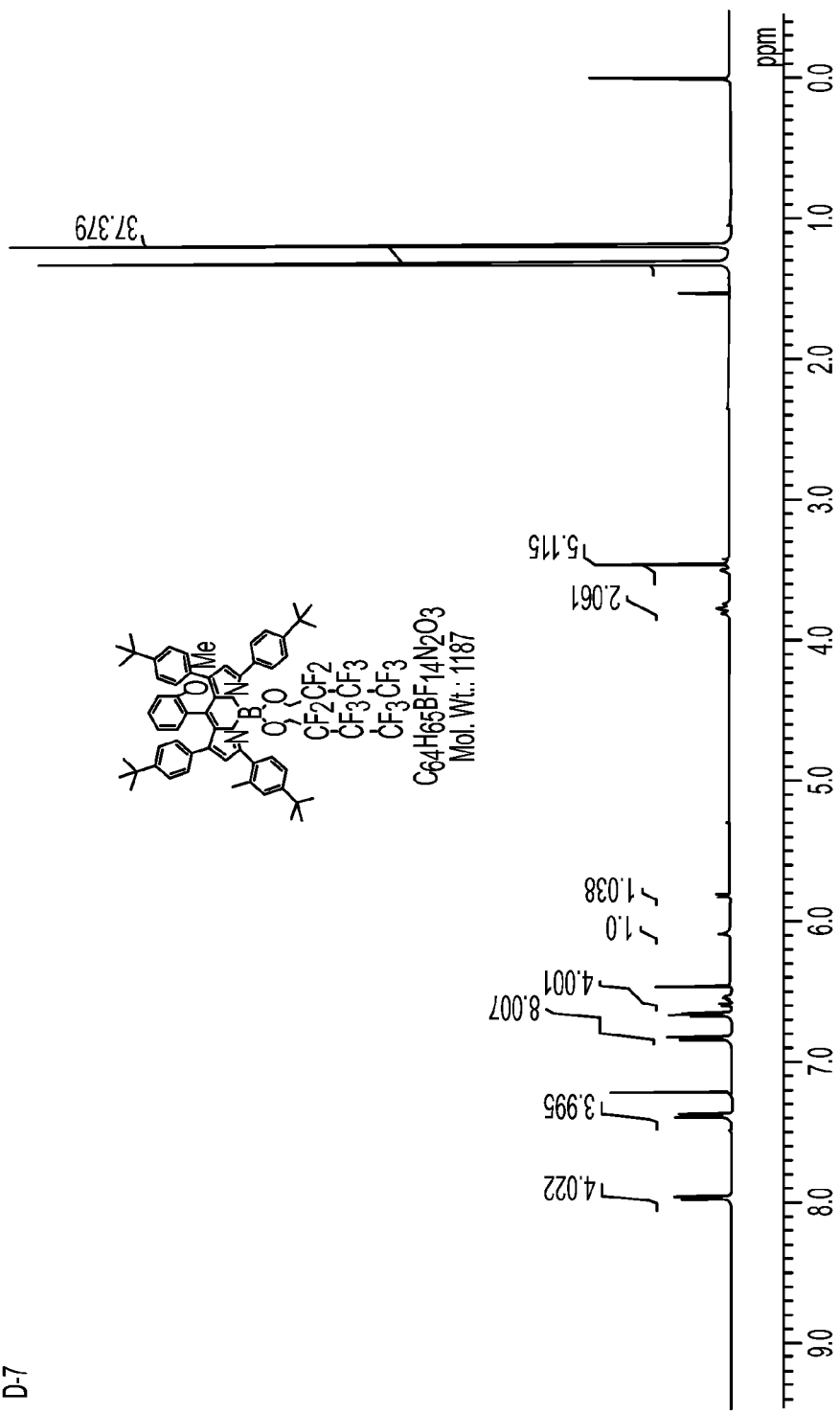
FIG. 7 is an H-NMR spectrum of the compound D-7 synthesized in Synthesis Example 7.

The structure of the compound D-7 obtained was confirmed by the H-NMR spectrum (FIG. 7) and the FD-MS spectrum (molecular ion m/Z=1187).

Synthesis Example 8

Synthesis of Compound D-8

5.0 g (15 mmol) of 2,4-bis(4-tert-butylphenyl)pyrrole (A-8) and 5.4 g (15 mmol) of 2-formyl-3,5-bis(4-tert-butylphenyl)pyrrole (B-8) were dissolved in 150 mL of methanol. To the resulting solution, 3 mL of a 48% aqueous hydrogen bromide solution was added and the mixture was stirred at 50 to 55° C. for 3 hours.

After 500 mL of toluene and 500 mL of hot water were added to the reaction solution and the mixture was stirred, a toluene phase was isolated and washed with 200 mL of a 1% aqueous sodium hydrogen carbonate solution and 200 mL of hot water in sequence. Then, the toluene phase was concentrated under reduced pressure. 50 mL of methanol was added to the residue, and the mixture was stirred for 30 minutes under reflux. After cooling to room temperature, the resulting solids were filtered, washed twice with 20 mL of methanol and dried to obtain a pyrromethene intermediate C-8 (yield: 9.8 g).

Next, in a nitrogen atmosphere, the pyrromethen intermediate C-8 (3.36 g, 5 mmol) was dissolved in 250 mL of toluene. To the resulting solution, a 1 mmol/L solution of trichlorobron in dichlomethane (20 mL, 20 mmol) was added with stirring. The mixture was stirred for one hour at room temperature. After heating to 70° C. and stirring for 2 hours, the solution was cooled to room temperature. Triethylamine (7.57 g, 75 mmol) was added dropwise, followed by further stirring for 30 minutes. At room temperature, a 10 mL toluene solution of 11.25 g (75 mmol) of 2,2,3,3,3-pentafluoropropanol was added, and the mixture was stirred for one hour.

250 mL of hot water was added to the solution and a toluene phase was isolated. Further, the toluene phase was washed twice with 250 mL of hot water and concentrated under reduced pressure by means of an evaporator. After the residue was purified by means of silica-gel chromatography (elution solvent: toluene/hexane=1/1), the fraction obtained was concentrated in an evaporator. 50 mL of methanol was added to the resultant, and the mixture was stirred for 30 minutes under reflux. After cooling to room temperature, filtration, washing twice with 20 mL of methanol and drying were conducted to obtain 3.4 g of reddish violet powder.

Figure 8:
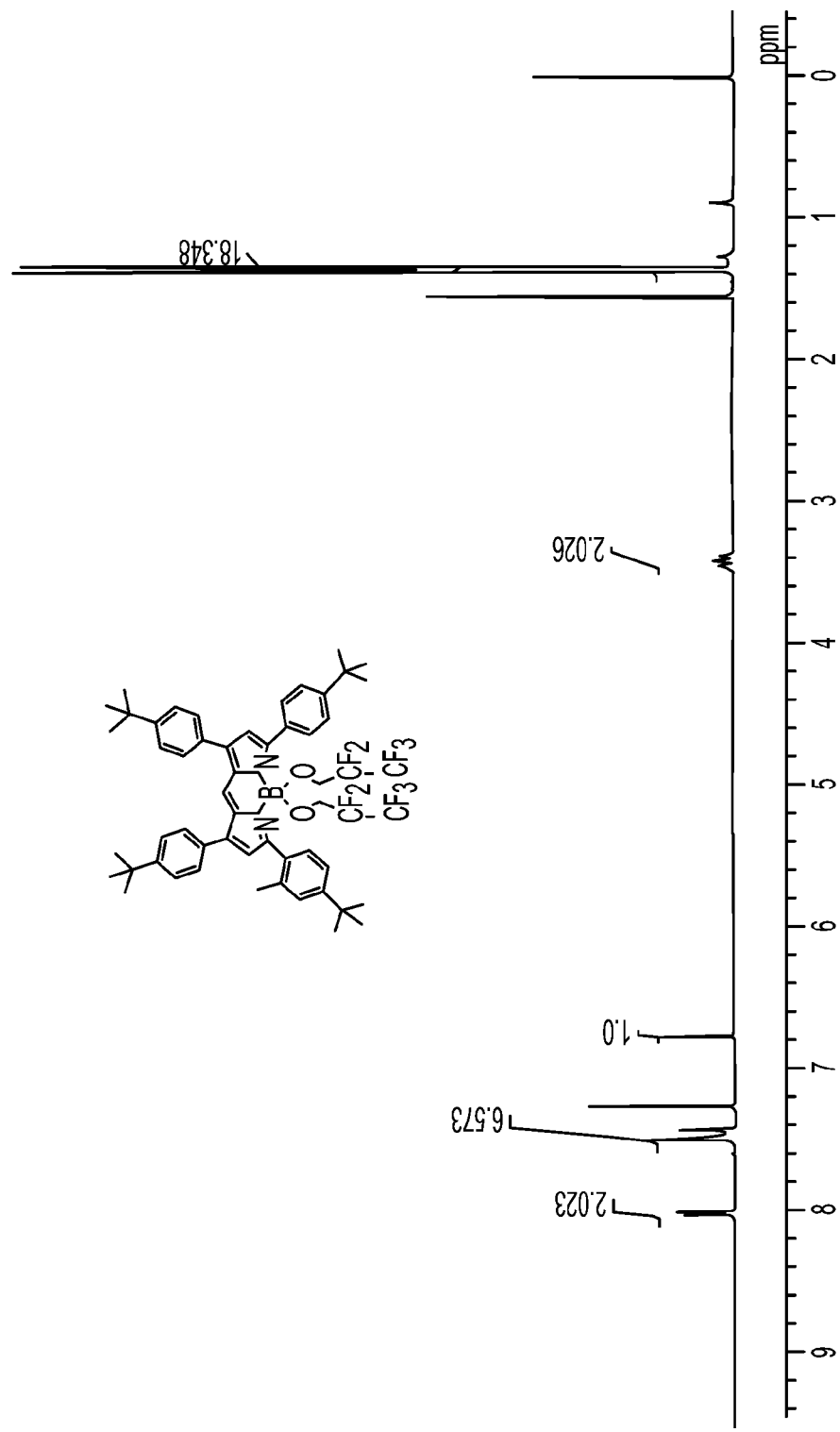
FIG. 8 is an H-NMR spectrum of the compound D-8 synthesized in Synthesis Example 8.

By the H-NMR spectrum (FIG. 8) and the FD-MS spectrum (molecular ion m/Z=980), the reddish violet powder obtained was confirmed to be compound D-8.

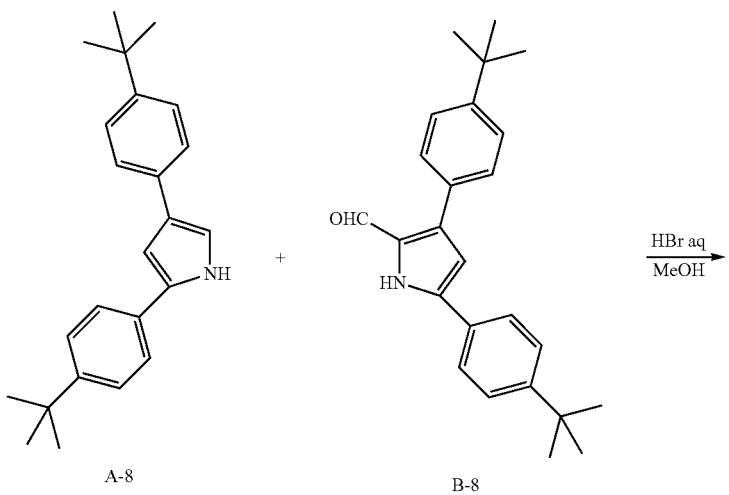

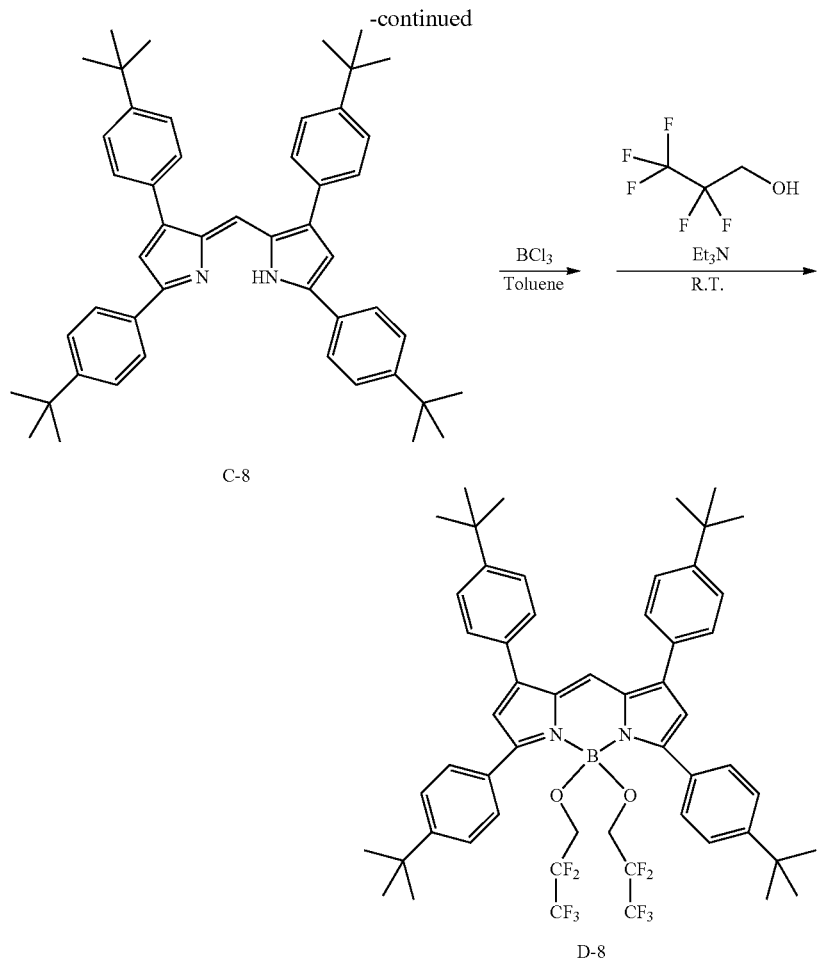

C-8

D-8

Synthesis Example 9

Synthesis of Compound D-9

Compound D-9 was synthesized in the same manner as in Synthesis Example 8, except that 2,2,3,3-tetrafluoropropanol (compound C-9) was used instead of 2,2,3,3,3-pentafluoropropanol.

Figure 9:
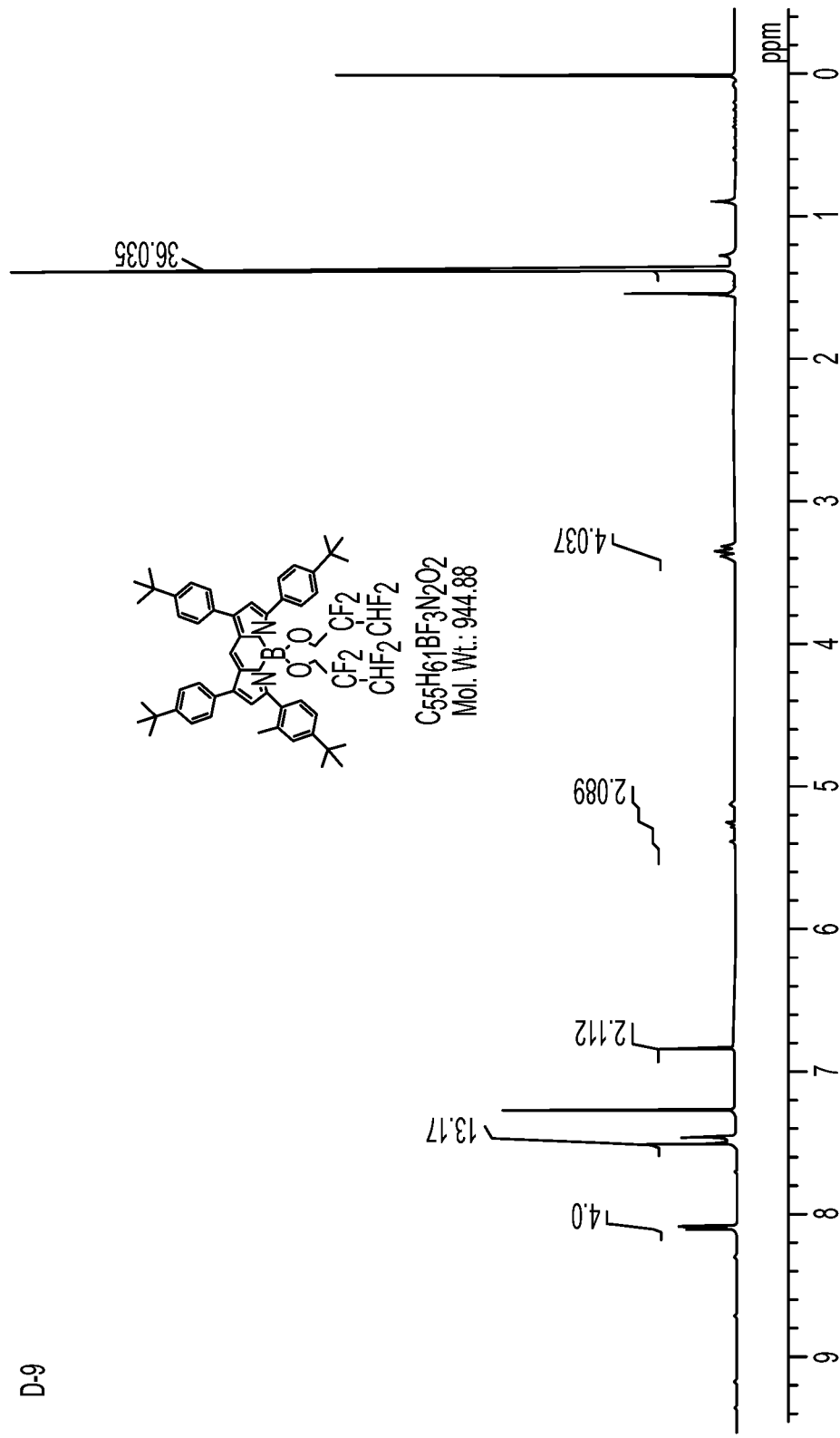
FIG. 9 is an H-NMR spectrum of the compound D-9 synthesized in Synthesis Example 9.

The structure of the compound D-9 obtained was confirmed by the H-NMR spectrum (FIG. 9) and the FD-MS spectrum (molecular ion m/Z=944).

Synthesis Example 10

Synthesis of Compound D-10

3.88 g (12.8 mmol) of 2-(2,4-dimethylphenyl)-4-(4-tert-butylphenyl) pyrrole (A-10) and 4.24 g (12.8 mmol) of 2-formyl-3-(2,4-dimethylphenyl)-5-(4-tert-butylphenyl)pyrrole (B-10) were dissolved in 130 mL of dichloroethane. To the resulting solution, 1.44 mL (15.4 mmol) of phosphorus oxychloride was slowly added dropwise. The mixture was refluxed with heating for 3 hours.

200 mL of a 10 wt % aqueous sodium acetate solution was added to the reaction liquid, and an organic phase was separated by extraction by using methylene chloride. After drying with anhydrous magnesium sulfate, the organic phase was concentrated under reduced pressure by means of an evaporator, whereby reddish violet powder was obtained.

The resulting solids were dissolved in 200 mL of anhydrous toluene. At room temperature, 8.3 mL (60 mmol) of triethylamine and 5 mL (18 mmol) of a boron trifluoride/diethyl ether complex were added in sequence. Then, the resulting mixture was heated to 80° C., and stirred for 2 hours. After cooling the reaction liquid to room temperature, a saturated aqueous sodium hydrogen carbonate solution was added thereto, whereby an organic phase was separated. The organic phase was concentrated by means of an evaporator, and the residue was purified by means of silica-gel chromatography (elution solvent: hexane/methylene chloride=3/1) to obtain 7.54 g of reddish violet powder of the pyrromethene-difluoroboron complex C-10.

In an argon atmosphere, anhydrous 1,2-dimethoxyethane (DME) (150 mL) was added to 0.75 g (30 mmol) of a 30 wt % lithium dispersion, followed by stirring. To the resulting mixture, 9 g (60 mmol) of 2,2,3,3,3-pentafluoropropanol was slowly added. At this time, the temperature inside the reaction system was elevated to around 50° C. After further stirring for 30 minutes, 1.99 g (3.0 mmol) of powder of the pyrromethene-difluoroboron complex C-10 was added in small quantities, followed by reflux with heating for 3 hours.

After cooling to room temperature, the reaction solution was passed through a flash column (elution solvent: methylene chloride).

The resulting solution was concentrated to dryness by means of an evaporator and the resulting residue was purified by means of silica-gel chromatography (elution solvent: hexane→hexane/methylene chloride=10/1 to 7/1) to obtain 2.53 g of reddish violet powder.

Figure 10:
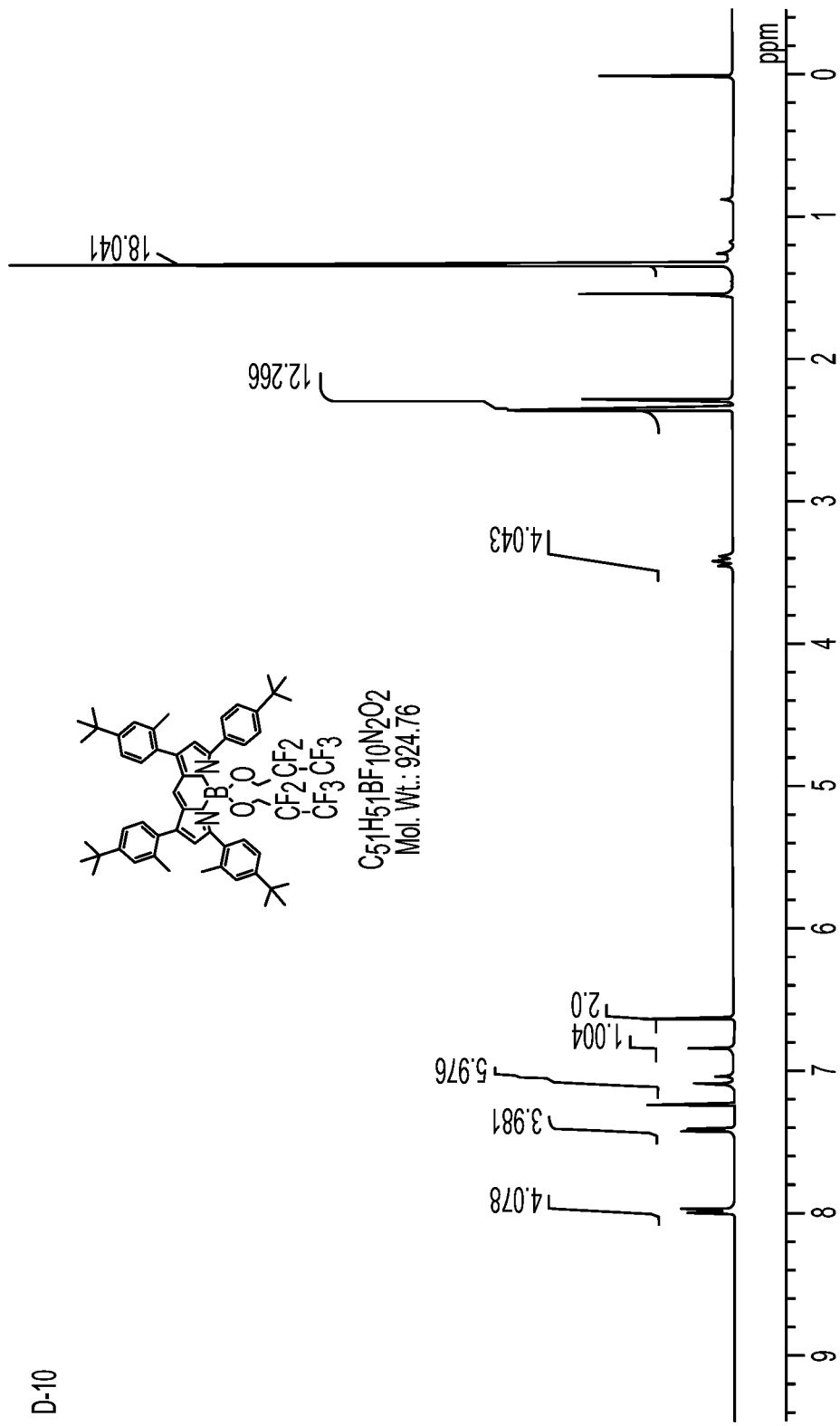
FIG. 10 is an H-NMR spectrum of the compound D-10 synthesized in Synthesis Example 10.

By the H-NMR spectrum (FIG. 10) and the FD-MS spectrum (molecular ion m/Z=924), the reddish violet powder obtained was confirmed to be compound D-10.

Figure 11:
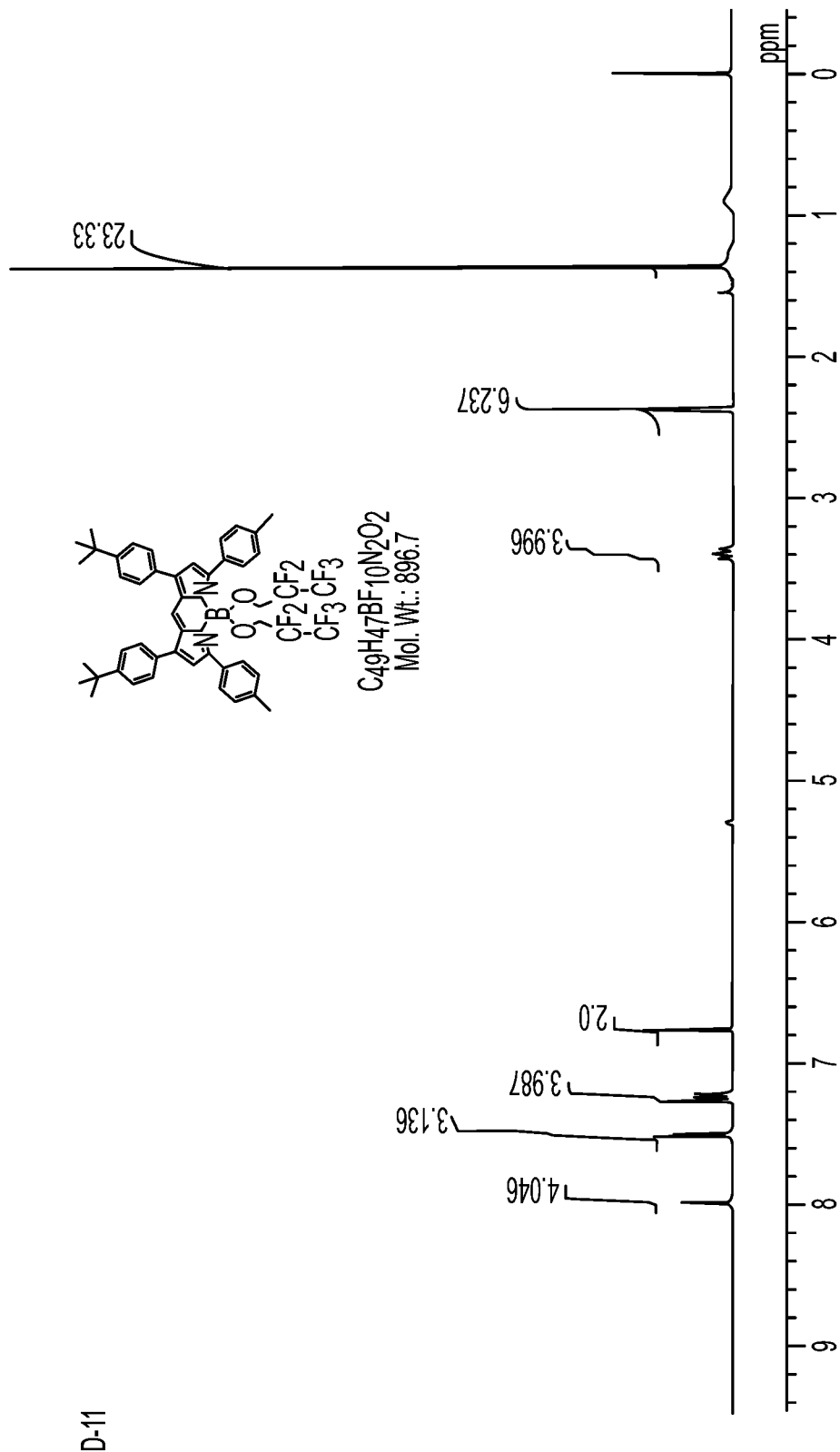
FIG. 11 is an H-NMR spectrum of the compound D-11 synthesized in Synthesis Example 11.

The structure of the compound D-11 obtained was confirmed by the H-NMR spectrum (FIG. 11) and the FD-MS spectrum (molecular ion m/Z=896).

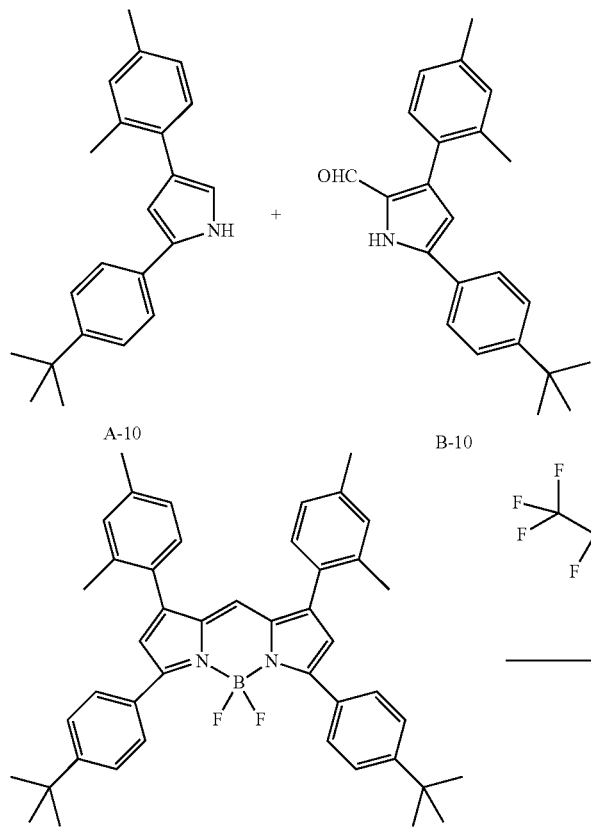

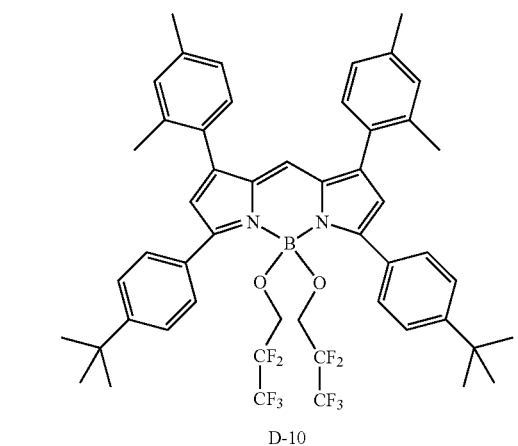

Synthesis Example 11

Synthesis of Compound D-11

Compound D-11 was synthesized in the same manner as in Synthesis Example 10, except that 2-(4-methylphenyl)-4-(4-tert-butylphenyl)pyrrole and 2-formyl-3-(4-tert-butylphenyl)-5-(4-methylphenyl)pyrrole (Compound C-11) were used as starting raw materials.

Synthesis Example 12

Synthesis of Compound D-12

Compound D-12 was synthesized in the same manner as in Synthesis Example 10, except that 2-(4-cyclohexylphenyl)-4-(2,4-dimethylphenyl)pyrrole and 2-formyl-3-(2,4-dimethylphenyl)-5-(4-cyclohexylphenyl)pyrrole (Compound C-12) were used as starting raw materials.

Figure 12:
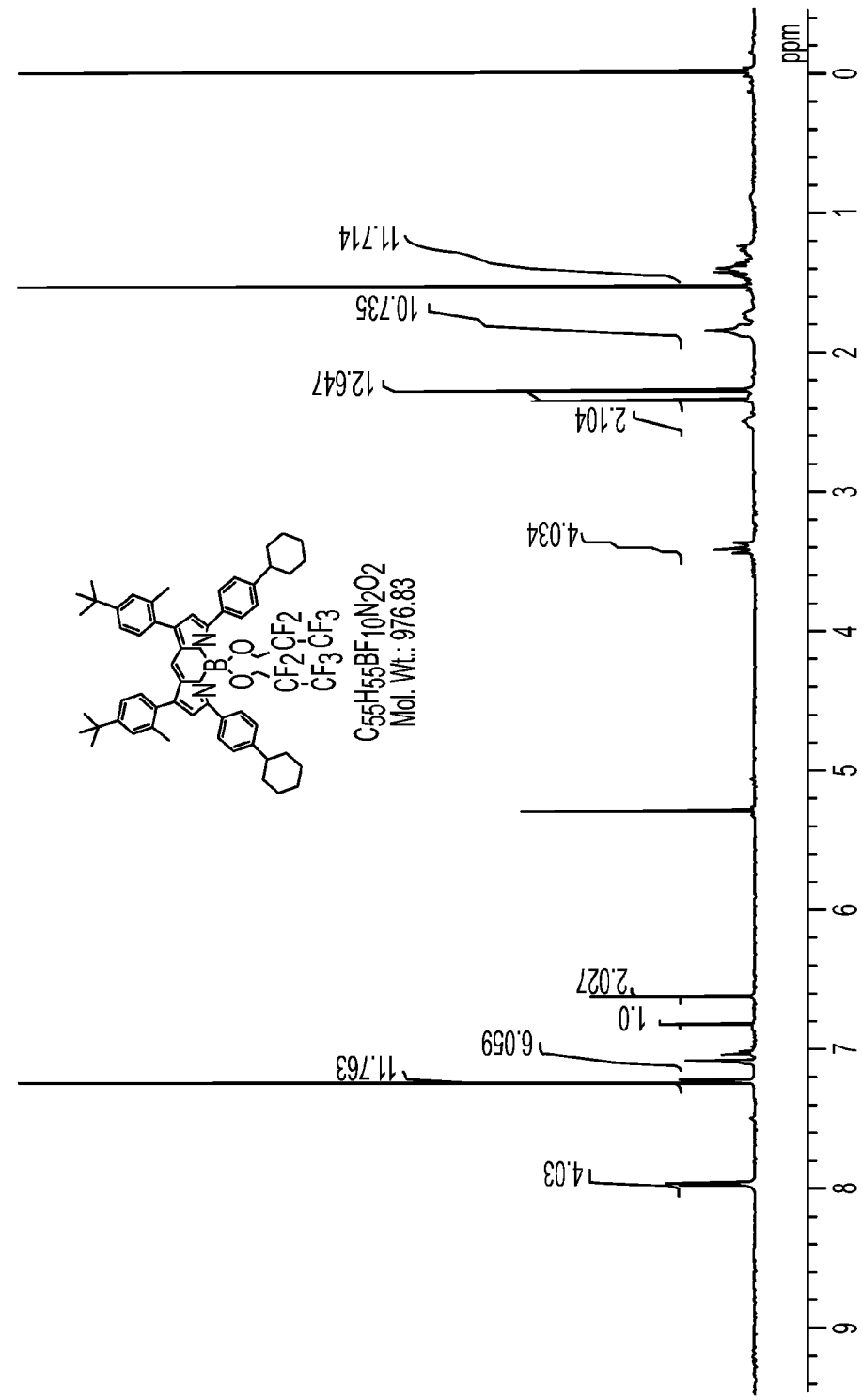
FIG. 12 is an H-NMR spectrum of the compound D-12 synthesized in Synthesis Example 12.

The structure of the compound D-12 obtained was confirmed by the H-NMR spectrum (FIG. 12) and the FD-MS spectrum (molecular ion m/Z=976).

Synthesis Example 13

Synthesis of Compound D-13

Compound D-13 was synthesized in the same manner as in Synthesis Example 10, except that 2-(4-methylphenyl)-4-(2,4,5-trimethylphenyl)pyrrole and 2-formyl-3-(2,4,5-trimethylphenyl)-5-(4-methylphenyl)pyrrole (Compound C-13) were used as starting raw materials.

Figure 13:
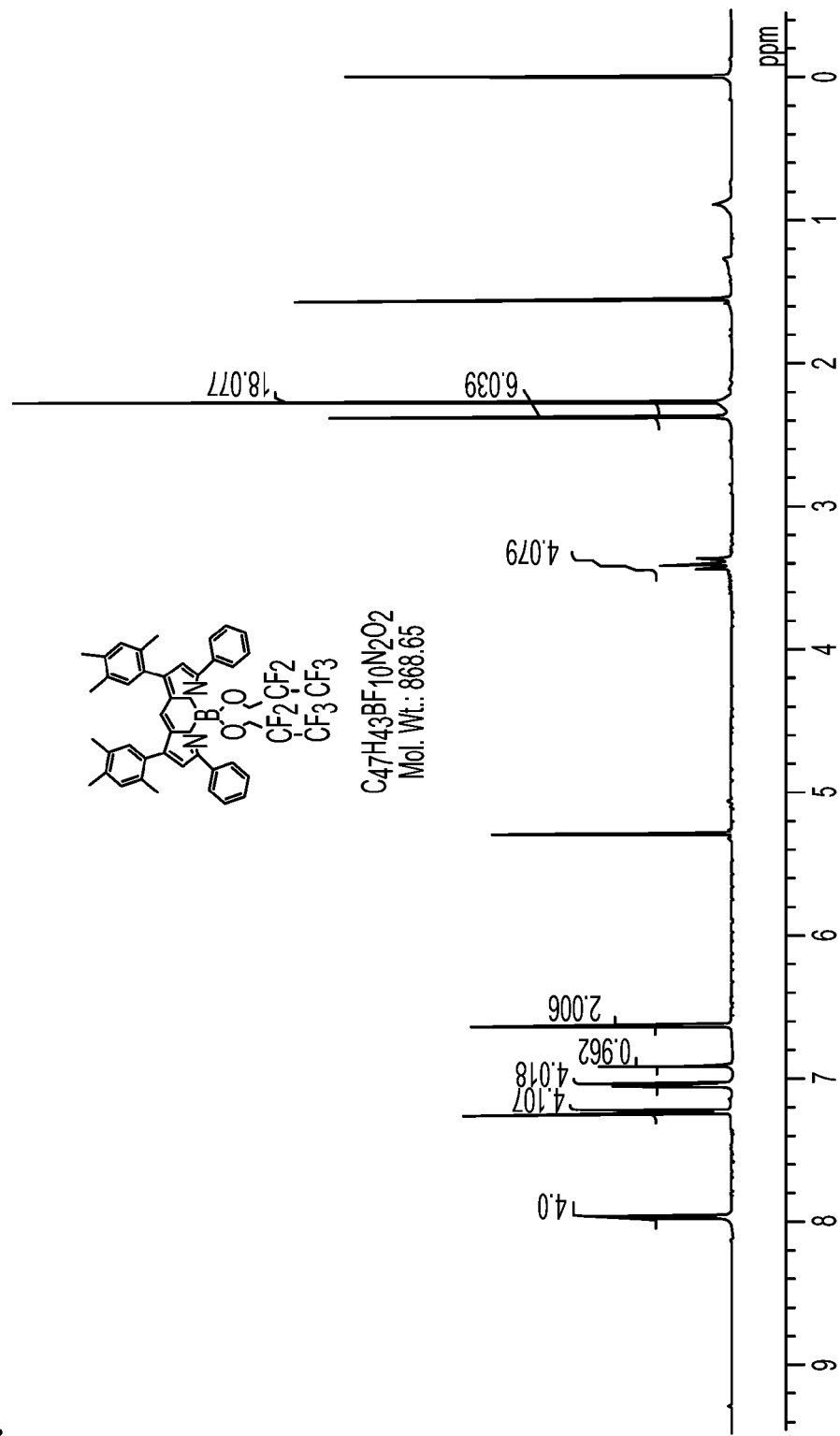
FIG. 13 is an H-NMR spectrum of the compound D-13 synthesized in Synthesis Example 13.

The structure of the compound D-13 obtained was confirmed by the H-NMR spectrum (FIG. 13) and the FD-MS spectrum (molecular ion m/Z=868).

Synthesis Example 14

Synthesis of Compound D-14

Compound D-14 was synthesized in the same manner as in Synthesis Example 10, except that 2-(4-methoxyphenyl)-4-(2,4-dimethylphenyl)pyrrole and 2-formyl-3-(2,4-dimethylphenyl)-5-(4-methylphenyl)pyrrole (Compound C-14) were used as starting raw materials.

Figure 14:
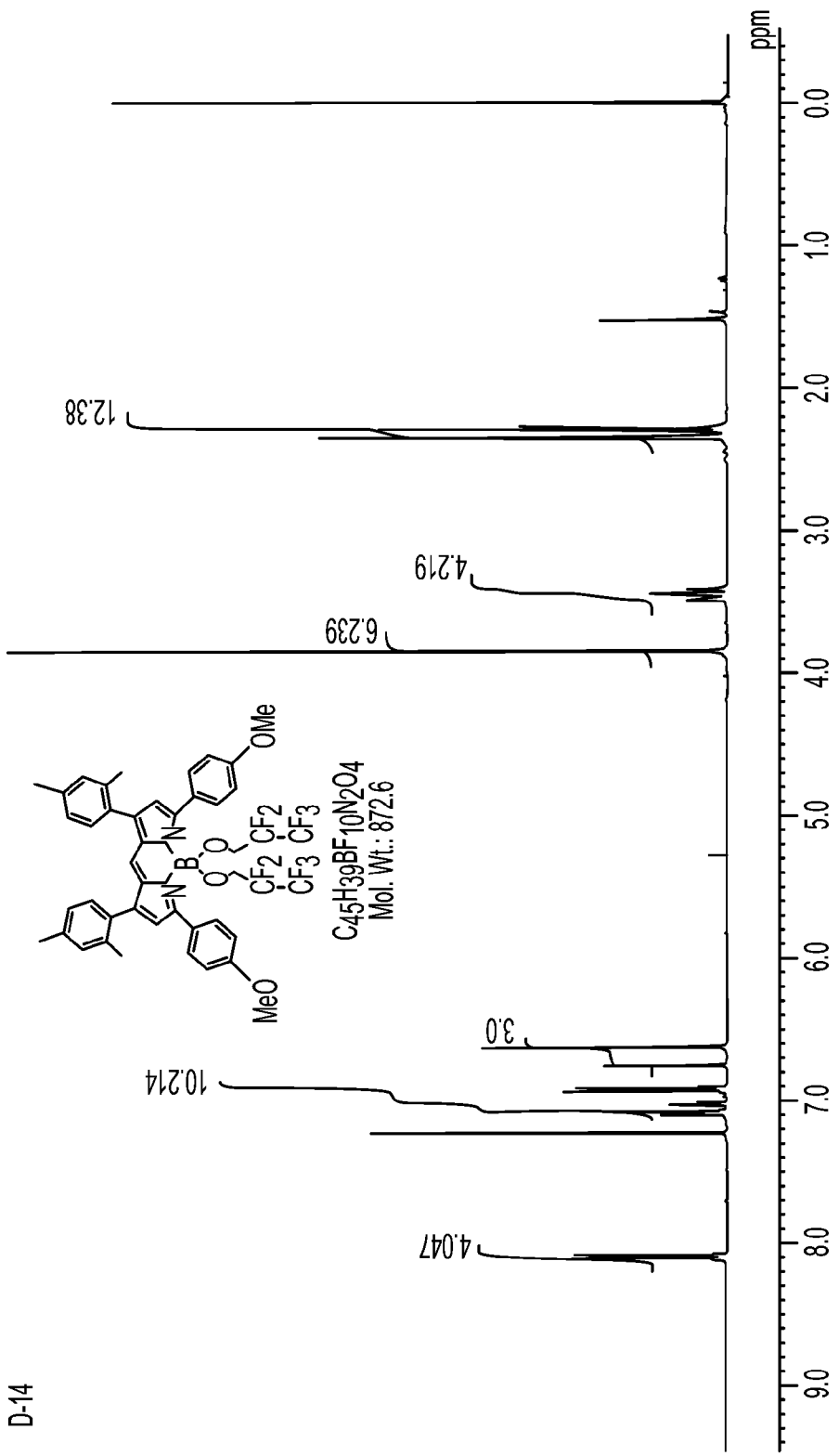
FIG. 14 is an H-NMR spectrum of the compound D-14 synthesized in Synthesis Example 14.

The structure of the compound D-14 obtained was confirmed by the H-NMR spectrum (FIG. 14) and the FD-MS spectrum (molecular ion m/Z=872).

Synthesis Example 15

Synthesis of Compound D-15

Compound D-15 was synthesized in the same manner as in Synthesis Example 10, except that 2,4-bis(4-tert-butylphenyl)pyrrole and 2-formyl-3,5-diphenylpyrrole (Compound C-15) were used as starting raw materials.

Figure 15:
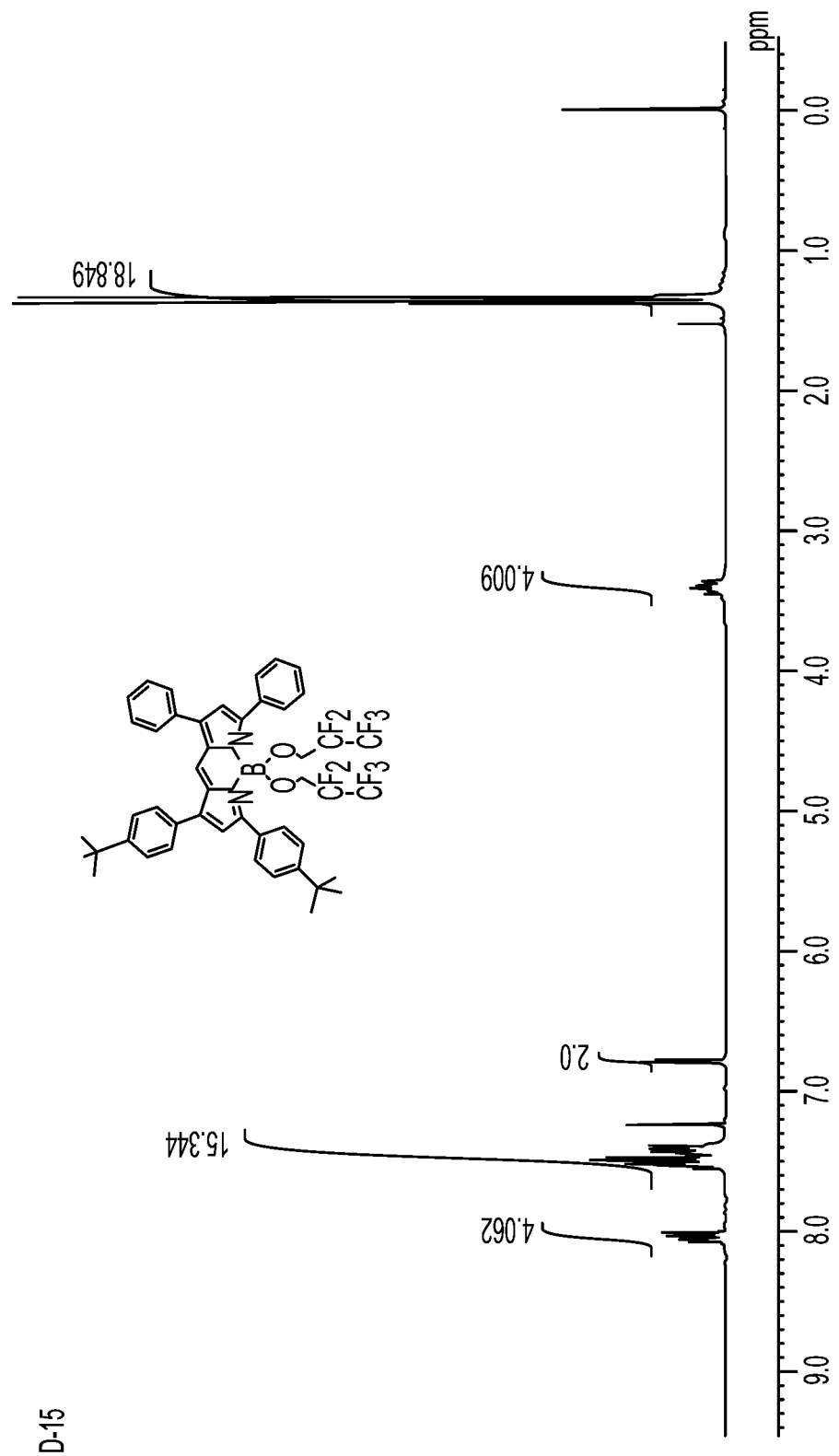
FIG. 15 is an H-NMR spectrum of the compound D-15 synthesized in Synthesis Example 15.

The structure of the compound D-15 obtained was confirmed by the H-NMR spectrum (FIG. 15) and the FD-MS spectrum (molecular ion m/Z=868).

[Evaluation of Pyrromethene-Boron Complex Compound]

The sublimation temperature, thermal decomposition properties and deposition temperature of the compounds D-1 to D-15 synthesized above are evaluated by the following methods. The results are shown in Table 1.

(1) Sublimation Temperature

The synthesized compounds were put in a heating furnace. Under a vacuum degree of $1\times10^{-3}$ Pa or less, the temperature of the heating furnace was elevated from 150° C. in such a manner that the temperature was increased by 10° C. at a time. The compound started to sublimate. From a temperature when the compound started to sublimate to have a lower temperature, the temperature of the heating furnace was further elevated by about 20° C. to allow the compound to fix. The temperature at this time was taken as the sublimation temperature of the compound.

(2) Thermal Decomposition Properties

The HPLC purity of the compound after purification by sublimation (after the measurement of the sublimation temperature) was measured. When the purity was lowered by 1% or more as compared with the purity before the purification by sublimation, it was evaluated that thermal decomposition occurred.

(3) Decomposition Temperature

The synthesized compound was filled in a molybdenum-made boat (capacity: 0.2 mL). A pair of thermocouple was inserted into a gap to measure the temperature inside the boat. At a vacuum degree of $1\times10^{-4}$ Pa or less, a temperature at which the deposition rate of a deposition film was 0.03 Å/S was taken as the deposition temperature of the compound.

TABLE 1

| Compound | Sublimation temperature [° C.] | Thermal decomposition (Lowering of purity) | Deposition temperature [° C.] |
|---|---|---|---|
| D-1 | 210 | None | 206 |
| D-2 | 230 | None | 214 |
| D-3 | 230 | None | 225 |
| D-4 | 230 | None | 199 |
| D-5 | 270 | None | 233 |
| D-6 | 270 | None | 258 |
| D-7 | 270 | None | 249 |
| D-8 | 280 | None | 270 |
| D-9 | 280 | None | 260 |
| D-10 | 270 | None | 215 |
| D-11 | 250 | None | 260 |
| D-12 | 260 | None | 255 |
| D-13 | 250 | None | 190 |
| D-14 | 260 | None | 250 |
| D-15 | 250 | None | 235 |
| C-1 | 240 | None | 255 |
| C-2 | 260 | None | 298 |
| C-3 | 280 | None | 215 |
| C 4 | 270 | Occurred | — |
| C-5 | 320 | None | 308 |
| C 8 | 340 | None | 330 |
| C-10 | 290 | None | 255 |
| C-11 | 280 | None | 270 |
| C-12 | 290 | None | 270 |
| C-13 | 270 | None | 220 |
| C-14 | 290 | None | 280 |
| C-15 | 270 | None | 255 |

Example 1

On a glass substrate of 25×75×1.1 mm, a 130 nm-thick transparent electrode formed of indium tin oxide was provided. This transparent electrode functions as an anode. Subsequently, this glass substrate was cleaned by irradiating UV rays and ozone. Then, the glass substrate was mounted in a vacuum vapor deposition apparatus.

First, a 60 nm-thick film formed of compound HI was deposited as a hole-injecting layer. Then, a 10 nm-thick film formed of compound HT was deposited thereon as a hole-transporting layer. Subsequently, compound H-1 as the host material and compound D-1 as the dopant were co-deposited such that the content of the dopant in the emitting layer became 1 wt %, thereby to form a 40 nm-thick emitting layer.

Next, as an electron-transporting layer, compound ET was deposited on this emitting layer in a thickness of 30 nm.

Subsequently, a 1 nm-thick film formed of lithium fluoride was deposited, and a 150 nm-thick film formed of aluminum was deposited, whereby an organic EL device was fabricated. The aluminum/lithium fluoride layer functions as a cathode.

For the resulting organic EL device, the device performance at the driving with a current density J of 10 mA/cm² (luminance L, CIE chromaticity coordinates, luminous efficiency L/J, external quantum efficiency $\phi_{ex}$, emission maximum wavelength $\lambda_p$ and full width at half maximum FWHM) was evaluated. The results are shown in Table 2.

Examples 2 to 11 and Comparative Examples 1 to 7

Organic EL devices were fabricated and evaluated in the same manner as in Example 1, except that the host materials and the dopants shown in Table 2 were used instead of compound H-1 and compound D-1. The results are shown in Table 2.

TABLE 2

| | Host | Dopant | L [cd/m²] | CIEx | CIEy | L/J [cd/A] | $\phi_{ex}$ [%] | $\lambda_p$ [nm] | FWHM [nm] |
|---|---|---|---|---|---|---|---|---|---|
| Example 1 | H-1 | D-1 | 462 | 0.70 | 0.30 | 4.6 | 8.4 | 645 | 42 |
| Com. Ex. 1 | H-1 | C-1 | 284 | 0.70 | 0.30 | 2.8 | 5.3 | 643 | 49 |
| Example 2 | H-1 | D-2 | 1058 | 0.66 | 0.34 | 10.6 | 8.4 | 624 | 55 |
| Com. Ex. 2 | H-1 | C-2 | 573 | 0.68 | 0.32 | 5.7 | 5.7 | 624 | 48 |
| Example 3 | H-1 | D-3 | 719 | 0.69 | 0.31 | 7.2 | 8.8 | 636 | 47 |
| Com. Ex. 3 | H-1 | C-3 | 480 | 0.69 | 0.31 | 4.8 | 6.4 | 634 | 59 |
| Example 4 | H-2 | D-3 | 548 | 0.69 | 0.31 | 5.5 | 6.5 | 635 | 46 |
| Com. Ex. 4 | H-2 | C-3 | 369 | 0.69 | 0.31 | 3.7 | 5.9 | 636 | 77 |
| Example 5 | H-3 | D-3 | 712 | 0.69 | 0.31 | 7.1 | 8.3 | 635 | 47 |
| Com. Ex. 5 | H-3 | C-3 | 412 | 0.69 | 0.31 | 4.1 | 7.2 | 661 | 76 |
| Example 6 | H-4 | D-3 | 681 | 0.69 | 0.31 | 6.8 | 8.4 | 636 | 46 |
| Com. Ex. 6 | H-4 | C-3 | 501 | 0.69 | 0.31 | 5.0 | 7.4 | 635 | 74 |
| Example 7 | H-5 | D-3 | 692 | 0.69 | 0.31 | 6.9 | 8.4 | 635 | 46 |
| Com. Ex. 7 | H-5 | C-3 | 445 | 0.69 | 0.31 | 4.4 | 6.7 | 636 | 75 |
| Example 8 | H-1 | D-4 | 843 | 0.68 | 0.32 | 8.4 | 8.5 | 633 | 53 |
| Example 9 | H-1 | D-5 | 1127 | 0.67 | 0.33 | 11.3 | 9.5 | 623 | 42 |
| Example 10 | H-1 | D-6 | 1117 | 0.67 | 0.33 | 11.2 | 9.1 | 623 | 44 |
| Example 11 | H-1 | D-7 | 1082 | 0.67 | 0.33 | 10.8 | 9.0 | 623 | 43 |

Examples 12 to 14

An organic EL device was fabricated in the same manner as in Example 3, except that the emitting layer was formed such that the content of the dopant (doping concentration) in the emitting layer became 0.5 wt % (Example 12). Further, organic EL devices with a doping concentration of 2 wt % and 3 wt %, respectively, were fabricated (Example 13 and Example 14).

For the organic EL devices fabricated in Example 3 and Examples 12 to 14, the device performance at the driving with a current density J of 10 mA/cm² (driving voltage V, luminance L, CIE chromaticity coordinates, luminous efficiency L/J, efficiency of power conversion η, external quantum efficiency $\phi_{ex}$, emission maximum wavelength $\lambda_p$ and full width at half maximum FWHM) was evaluated. The results are shown in Table 3.

Figure 16:
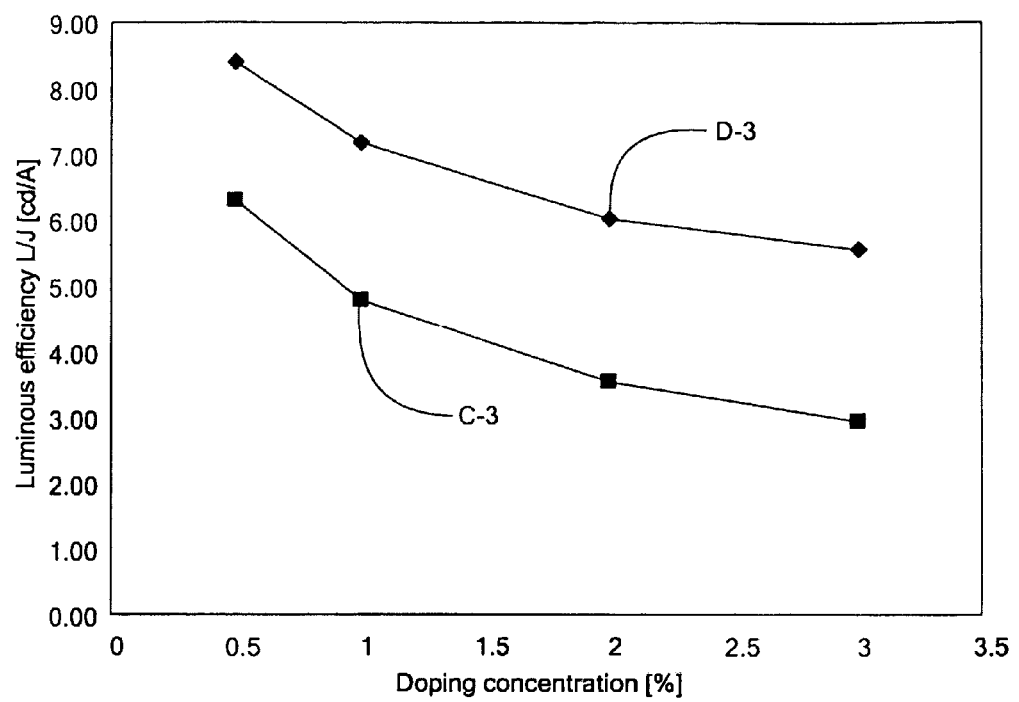
FIG. 16 is a view showing the relationship between the doping concentration and the luminous efficiency (doping concentration dependency) of the compound D-3 used in Example 3 and Examples 12 to 14 and the compound C-3 used in Comparative Example 3 and Comparative Examples 8 to 10.

Further, the relationship between the doping concentration and the luminous efficiency of compound D-3 used in Example 3 and Examples 12 to 14 (doping concentration dependency) is shown in FIG. 16.

Comparative Examples 8 to 10

Organic EL devices were fabricated in the same manner as in Comparative Example 3, except that the emitting layer was formed such that the content of the dopant (doping concentration) in the emitting layer became 0.5 wt % (Comparative Example 8). Further, organic EL devices with a doping concentration of 2 wt % and 3 wt %, respectively, were fabricated (Comparative Example 9 and Comparative Example 10).

For the organic EL device fabricated in Comparative Example 3 and Comparative Examples 8 to 10, the device performance at the driving with a current density J of 10 mA/cm² (driving voltage V, luminance L, CIE chromaticity coordinates, luminous efficiency L/J, efficiency of power conversion η, external quantum efficiency $\phi_{ex}$, emission maximum wavelength $\lambda_p$ and full width at half maximum FWHM) was evaluated. The results are shown in Table 3.

Further, the relationship between the doping concentration and the luminous efficiency of compound C-3 used in Comparative Example 3 and Comparative Examples 8 to 10 (doping concentration dependency) is shown in FIG. 16.

TABLE 3

| | Doping concentration [wt %] | V [V] | L [cd/m2] | CIEx | CIEy | L/J [cd/A] | η [lm/W] | $\phi$ex [%] | $\lambda$p [nm] | FWHM [nm] |
|---|---|---|---|---|---|---|---|---|---|---|
| Example 12 | 0.5 | 4.30 | 840 | 0.680 | 0.319 | 8.40 | 6.14 | 9.16 | 634 | 46 |
| Example 3 | 1 | 4.49 | 719 | 0.689 | 0.311 | 7.19 | 5.04 | 8.78 | 636 | 47 |
| Example 13 | 2 | 4.60 | 603 | 0.693 | 0.306 | 6.03 | 4.12 | 7.82 | 637 | 45 |
| Example 14 | 3 | 4.82 | 558 | 0.695 | 0.305 | 5.58 | 3.63 | 7.45 | 637 | 45 |
| Com. Ex. 8 | 0.5 | 4.32 | 631 | 0.685 | 0.314 | 6.31 | 4.59 | 7.22 | 632 | 51 |
| Com. Ex. 3 | 1 | 4.40 | 480 | 0.691 | 0.309 | 4.80 | 3.42 | 6.36 | 634 | 59 |
| Com. Ex. 9 | 2 | 4.46 | 355 | 0.695 | 0.305 | 3.55 | 2.50 | 5.64 | 637 | 71 |
| Com. Ex. 10 | 3 | 4.44 | 294 | 0.697 | 0.303 | 2.94 | 2.08 | 5.27 | 639 | 77 |

Figure 17:
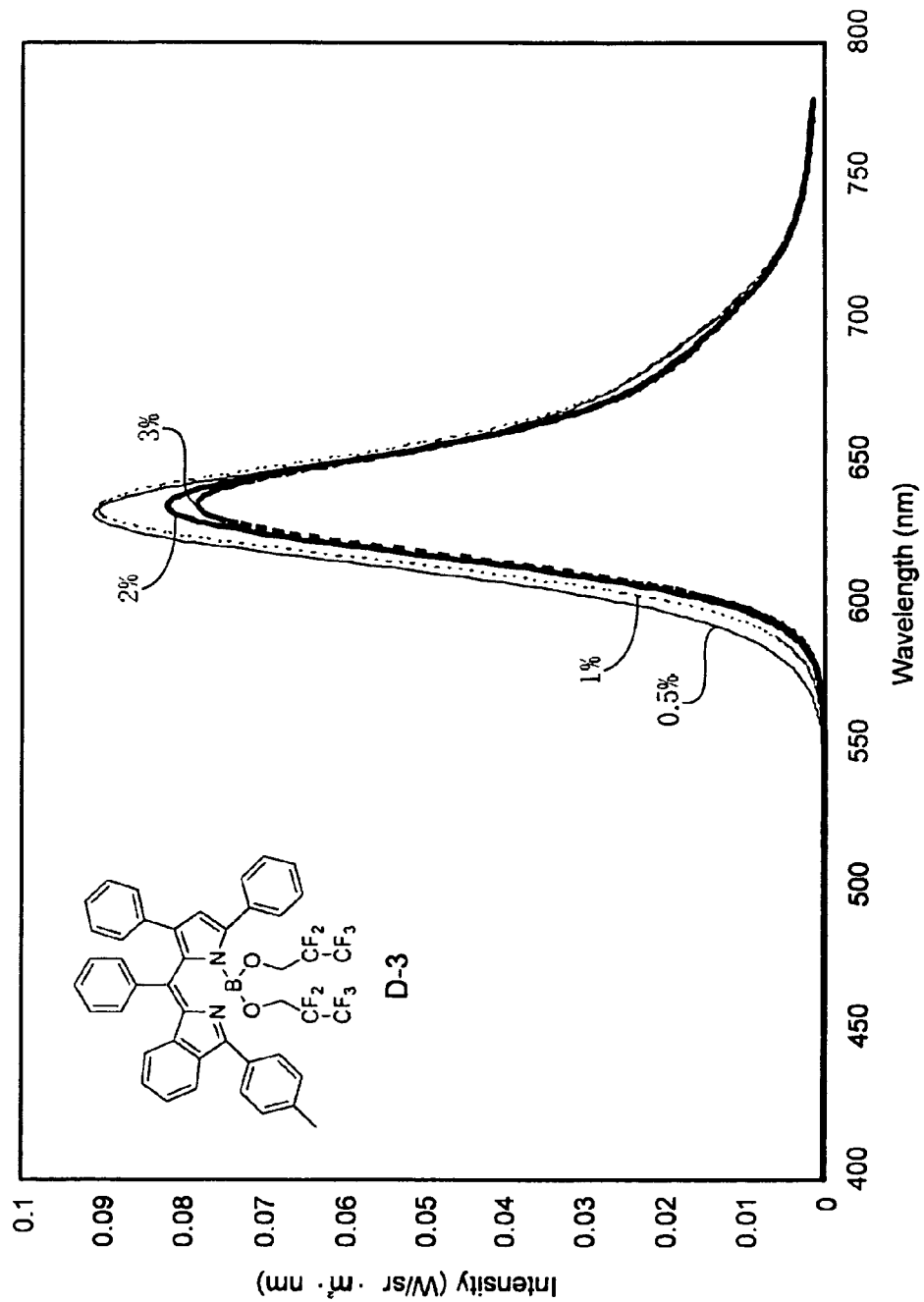
FIG. 17 is a view showing the relationship between the luminous intensity and the emission wavelength Of the organic EL devices of Examples 3 and Examples 12 to 14.

The relationship between the luminous intensity and emission wavelength of the organic EL devices of Example 3 and Examples 12 to 14 is shown in FIG. 17. Similarly, the relationship between the luminous intensity and emission wavelength of the organic EL devices of Comparative Example 3 and Comparative Examples 8 to 10 is shown in FIG. 18.

Figure 18:
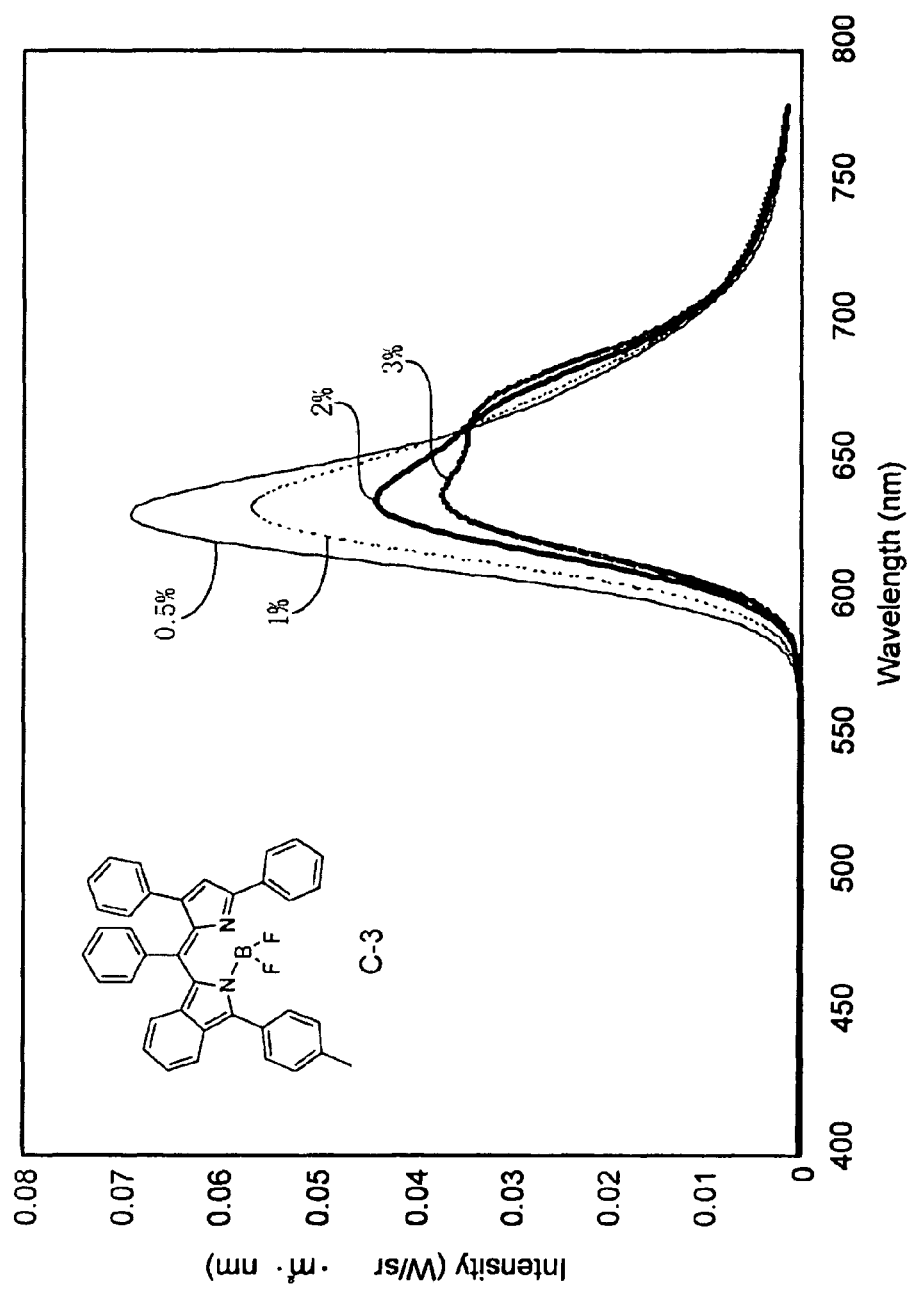
FIG. 18 is a view showing the relationship between the luminous intensity and the emission wavelength of the organic EL devices of Comparative Example 3 and Comparative Examples 8 to 10.

From FIG. 17 and FIG. 18, it can be understood that the pyrromethene-boron complex compound of the invention hardly caused concentration quenching.

Examples 15 to 22 and Comparative Examples 11 to 17

Organic EL devices were fabricated and evaluated in the same manner as in Example 1, except that the emitting layer was formed by using the dopants shown in Table 4 instead of compound D-1. The results are shown in Table 4.

TABLE 4

| | Host | Dopant | L [cd/m²] | CIEx | CIEy | L/J [cd/A] | φ$_{ex}$ [%] | λ$_p$ [nm] | FWHM [nm] |
|---|---|---|---|---|---|---|---|---|---|
| Example 15 | H-1 | D-8 | 820 | 0.69 | 0.31 | 8.3 | 8.4 | 628 | 37 |
| Example 16 | H-1 | D-9 | 700 | 0.69 | 0.31 | 7.0 | 7.0 | 627 | 37 |
| Com. Ex. 11 | H-1 | C-8 | 460 | 0.68 | 0.32 | 4.6 | 5.5 | 628 | 46 |
| Example 17 | H-1 | D-10 | 1077 | 0.68 | 0.32 | 10.8 | 8.7 | 622 | 35 |
| Com. Ex. 12 | H-1 | C-10 | 870 | 0.67 | 0.33 | 8.7 | 7.0 | 620 | 37 |
| Example 18 | H-1 | D-11 | 679 | 0.69 | 0.31 | 6.8 | 7.3 | 630 | 37 |
| Com. Ex. 13 | H-1 | C-11 | 448 | 0.68 | 0.32 | 4.5 | 5.3 | 629 | 46 |
| Example 19 | H-1 | D-12 | 1128 | 0.68 | 0.32 | 11.3 | 9.4 | 624 | 35 |
| Com. Ex. 14 | H-1 | C-12 | 883 | 0.67 | 0.33 | 8.8 | 7.3 | 621 | 37 |
| Example 20 | H-1 | D-13 | 1004 | 0.68 | 0.32 | 10.0 | 8.2 | 622 | 35 |
| Com. Ex. 15 | H-1 | C-13 | 808 | 0.67 | 0.33 | 8.1 | 6.4 | 619 | 38 |
| Example 21 | H-1 | D-14 | 611 | 0.70 | 0.30 | 6.1 | 8.8 | 640 | 36 |
| Com. Ex. 16 | H-1 | C-14 | 509 | 0.70 | 0.30 | 5.1 | 7.3 | 640 | 38 |
| Example 22 | H-1 | D-15 | 568 | 0.68 | 0.32 | 5.7 | 4.2 | 624 | 39 |
| Com. Ex. 17 | H-1 | C-15 | 423 | 0.67 | 0.33 | 4.2 | 3.3 | 623 | 48 |

From the results shown in Table 4, as compared the devices of Examples in which the compounds having a fluoroalkoxy group as the substituent on boron were used with the devices of Comparative Examples in which corresponding intermediate compounds having a fluorine atom as the substituent on boron were used, it can be understood that the devices of Examples have a higher luminous efficiency, improved color purity and a high external quantum efficiency as compared with the devices of Comparative Examples.

INDUSTRIAL APPLICABILITY

The organic EL device of the invention can be used as a planar emitting body such as a flat panel display of a wall-hanging television, backlight of a copier, a printer or a liquid crystal display, light sources for instruments, a display panel, navigation light, and the like.

The pyrromethene-boron complex compound of the invention can be used not only in an organic EL device but also in other fields such as an electrophotographic photoreceptor, a photoelectric conversion element, a solar cell and an image sensor.

Although only some exemplary embodiments and/or examples of this invention have been described in detail above, those skilled in the art will readily appreciated that many modifications are possible in the exemplary embodiments and/or examples without materially departing from the novel teachings and advantages of this invention. Accordingly, all such modifications are intended to be included within the scope of this invention.

The contents of the above-described documents are herein incorporated by reference in its entirety.

The invention claimed is:

1. A pyrromethene-boron complex compound represented by the following formula (1):

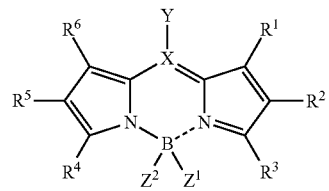

(1)

wherein $R^1$ to $R^6$ and Y are independently a hydrogen atom, a substituted or unsubstituted alkyl group, a substituted or unsubstituted cycloalkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, a substituted or unsubstituted heterocyclic group, a halogen atom, a haloalkyl group, a carboxyl group, an ester group, a carbamoyl group, an amino group, a nitro group, a cyano group, a silyl group or a siloxanyl group, adjacent substituents of $R^1$ to $R^6$ may form a substituted or unsubstituted fused aromatic ring or a substituted or unsubstituted aliphatic ring, X is a carbon atom or a nitrogen atom, and when X is a nitrogen atom, Y is not present, $Z^1$ and $Z^2$ are independently a hydrogen atom, a substituted or unsubstituted aryl group, a substituted or unsubstituted alkoxy group or a substituted or unsubstituted aryloxy group, at least one of $Z^1$ and $Z^2$ is an alkoxy group substituted with a fluorine atom or an aryloxy group substituted with a fluorine atom or a fluoroalkyl group, and $Z^1$ and $Z^2$ may form a ring structure.

2. The pyrromethene-boron complex compound according to claim 1, which is represented by the following formula (2):

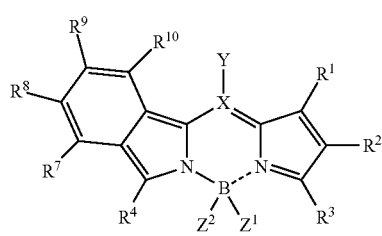

(2)

wherein $R^1$ to $R^4$, X Y and $Z^1$ and $Z^2$ are the same as those in the formula (1), $R^7$ to $R^{10}$ are independently a hydrogen atom, a substituted or unsubstituted alkyl group, a substituted or unsubstituted cycloalkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, a substituted or unsubstituted heterocyclic group, a halogen atom, a haloalkyl group, a carboxyl group, an ester group, a carbamoyl group, an amino group, a nitro group, a cyano group, a silyl group or a siloxanyl group, and adjacent substituents of $R^1$ to $R^4$ and $R^7$ to $R^{10}$ may form a substituted or unsubstituted fused aromatic ring or a substituted or unsubstituted aliphatic ring.

3. The pyrromethene-boron complex compound according to claim 1, wherein in the formula (1), X is a carbon atom, and Y is a hydrogen atom.

4. The pyrromethene-boron complex compound according to claim 3, wherein $R^1$, $R^3$, $R^4$ and $R^6$ in the formula (1) are independently a substituted or unsubstituted aryl group.

5. The pyrromethene-boron complex compound according to claim 1, wherein in the formula (1), at least one of $Z^1$ and $Z^2$ is an alkoxy group substituted with a fluorine atom.

6. The pyrromethene-boron complex compound according to claim 1, which is a dopant for an organic electroluminescence device.

7. An organic electroluminescence device comprising:
an anode, a cathode, and
one or a plurality of organic thin film layers between the anode and the cathode, the organic thin film layers comprising at least an emitting layer,
wherein at least one of the organic thin film layers comprises the pyrromethene-boron complex compound according to claim 1.

8. The organic electroluminescence device according to claim 7, wherein the emitting layer comprises the pyrromethene-boron complex compound.

9. The organic electroluminescence device according to claim 8, wherein the emitting layer further comprises a naphthacene derivative represented by the following formula (3):

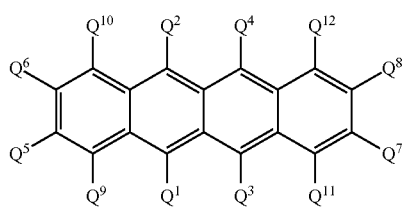

wherein $Q^1$ to $Q^{12}$ are independently a hydrogen atom, a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms.

10. The organic electroluminescence device according to claim 9, wherein at least one of $Q^1$, $Q^2$, $Q^3$ and $Q^4$ of the naphthacene derivative represented by the formula (3) is an aryl group.

11. The organic electroluminescence device according to claim 9, wherein the naphthacene derivative represented by the formula (3) is a naphthacene derivative represented by the following formula (4):

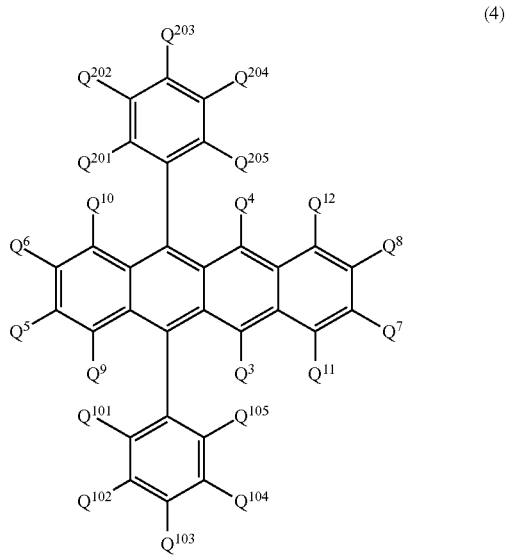

wherein $Q^3$ to $Q^{12}$ are the same as those in the formula (3), $Q^{101}$ to $Q^{105}$ and $Q^{201}$ to $Q^{205}$ are independently a hydrogen atom, a substituted or unsubstituted alkyl group having 1 to 20 carbon atoms, a substituted or unsubstituted aryl group having 6 to 20 ring carbon atoms, an amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms, and adjacent substituents of $Q^{101}$ to $Q^{105}$ and $Q^{201}$ to $Q^{205}$ may form a ring.

12. The organic electroluminescence device according to claim 11, wherein at least one of $Q^{101}$, $Q^{105}$, $Q^{201}$ and $Q^{205}$ of the naphthacene derivative represented by the formula (4) is a substituted or unsubstituted alkyl group having 1 to 20 carbon atoms, a substituted or unsubstituted aryl group having 6 to 20 ring carbon atoms, a an amino group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 20 ring carbon atoms, a substituted or unsubstituted alkenyl group having 2 to 20 carbon atoms, a substituted or unsubstituted aralkyl group having 7 to 20 ring carbon atoms or a substituted or unsubstituted heterocyclic group having 5 to 20 ring atoms.

13. The pyrromethene-boron complex compound according to claim 2, wherein in the formula (2), X is a carbon atom, and Y is a hydrogen atom.

14. The pyrromethene-boron complex compound according to claim 13, wherein $R^1$, $R^3$ and $R^4$ in the formula (2) are independently a substituted or unsubstituted aryl group.

15. The pyrromethene-boron complex compound according to claim 2, wherein in the formula (2), at least one of $Z^1$ and $Z^2$ is an alkoxy group substituted with a fluorine atom.

* * * * *